(12) United States Patent
Sagawa et al.

(10) Patent No.: US 6,770,481 B1
(45) Date of Patent: Aug. 3, 2004

(54) GENE ISOLATION METHOD

(75) Inventors: Hiroaki Sagawa, Kusatsu (JP); Harumi Ueno, Kusatsu (JP); Atsushi Oshima, Otsu (JP); Ikunoshin Kato, Uji (JP)

(73) Assignee: Takara Shuzo Co., Ltd., Kyoto (JP)

( * ) Notice: Subject to any disclaimer, the term of this patent is extended or adjusted under 35 U.S.C. 154(b) by 0 days.

(21) Appl. No.: 09/690,885

(22) Filed: Oct. 18, 2000

Related U.S. Application Data

(62) Division of application No. 08/952,089, filed as application No. PCT/JP97/00748 on Mar. 10, 1997, now Pat. No. 6,165,749.

(30) Foreign Application Priority Data

Mar. 13, 1996 (JP) ............................................. 8-85801
Jul. 18, 1996 (JP) ............................................ 8-208897

(51) Int. Cl.$^7$ ...................... C12N 15/63; C12N 15/64; C12N 15/52
(52) U.S. Cl. .............................. 435/478; 435/5; 435/6; 435/69.1; 435/471; 435/476; 435/243; 435/252.3
(58) Field of Search .............................. 435/5, 6, 69.1, 435/471, 476, 478, 243, 252.3

(56) References Cited

U.S. PATENT DOCUMENTS

| | | |
|---|---|---|
| 5,015,573 A | 5/1991 | Yarranton et al. |
| 5,137,823 A | 8/1992 | Brooks |
| 5,196,318 A | 3/1993 | Baldwin et al. |
| 5,320,957 A | 6/1994 | Brooks et al. |
| 5,354,680 A | 10/1994 | Brooks et al. |
| 5,843,703 A | 12/1998 | Campbell et al. |

FOREIGN PATENT DOCUMENTS

| | | |
|---|---|---|
| JP | A-3007584 | 1/1991 |
| WO | WO 85/04419 | 10/1985 |
| WO | WO 96/40947 | 12/1996 |

OTHER PUBLICATIONS

Fomenkov et al., Nucleic Acids Research, vol. 22, No. 12 (1994) pp. 2399–2403.
Studier et al., J. Mol. Biol., (1986) pp. 113–130.
Rosenberg et al., Gene, vol. 56 (1987) pp. 125–135.
Studier, J. Mol. Biol., vol. 219 (1991) pp. 37–44.
Dubendorff et al., J. Mol. Biol., vol. 219 (1991) pp. 45–59.
Dubendorff et al., J. Mol. Biol., vol. 219 (1991) pp. 61–68.
Kotani et al., Nucleic Acids Research, vol. 15 (1987) pp. 2653–2664.
Kita et al., Nucleic Acids Research, vol. 13 pp. 8685–8694.
Sagawa et al., Gene, vol. 168 (1996) pp. 37–41.
Nordström et al., Bio/Technology, vol. 10 (1992) pp. 661–666.
Wright et al., Gene, vol. 49 (1996) pp. 311–321.
Chew et al., Biotechnol., vol. 13 (1990) pp. 47–60.
Miller et al., J. Mol. Biol., vol. 194, (1987) pp. 397–410.
Webster's II New Roverside University Dictionary, (1994) pp. 358, 565, 687, and 1222. Houghton Mifflin, Boston, MA.
Lebedeva et al., Gene, vol. 142 (1994) pp. 61–66.
"Genetic Engineering for Engineering", pp. 166–170.
Donald O. Nwankwo, Gene, vol. 157, (1995), pp. 31–35.
XP–002201137, H.B. Kim et al., Korean J. of Microbiology (1989) pp. 317–322 (English Abstract).
Metcalf et al., Plasmid, vol. 35 (1996) pp. 1–13.
Togna et al., Biotechnol. Prog., vol. 9 (1993) pp. 31–39.

*Primary Examiner*—David Guzo
(74) *Attorney, Agent, or Firm*—Birch, Stewart, Kolasch & Birch, LLP.

(57) ABSTRACT

A plasmid vector characterized by comprising a promoter sequence that can be recognized by an RNA polymerase which is not inherent in a host and that controls the expression of desired genes and a replication origin that increases the number of copies under the induction by exogenous factors; methods for expression and isolation of target genes by using the vector; a polypeptide having the activity of an AccIII restriction endonuclease; and a DNA encoding the polypeptide. The invention provides for the first time a plasmid vector which can introduce an exogenous desired gene encoding proteins which are lethal or harmful to hosts into the hosts, a method for efficiently expressing the proteins by using the vector, and also a method for permitting a restriction endonuclease-gene constituting a restriction-modification system to be isolated even in the absence of a modification enzyme gene, which has been difficult in the prior arts.

5 Claims, 26 Drawing Sheets

SEQUENCE LISTING (1) GENERAL INFORMATION:

(iii) NUMBER OF SEQUENCES: 33

(2) INFORMATION FOR SEQ ID NO: 1:

(i) SEQUENCE CHARACTERISTICS:
      (A) LENGTH: 295 amino acids
      (B) TYPE: amino acid
      (C) STRANDEDNESS: single
      (D) TOPOLOGY: linear (ii) MOLECULE TYPE: protein (ix) FEATURE:
      (A) NAME/KEY: Modified-site (B) LOCATION: 2
(D) OTHER INFORMATION: /note= "2=Val or Leu"

(xi) SEQUENCE DESCRIPTION: SEQ ID NO: 1:

```
Met Xaa Pro Leu Asp Lys Asp Leu Gln Lys Ala Lys Ile Ser Ile Thr
1               5                   10                  15

Asp Phe Phe Glu Ile Thr Asn Arg Val Leu Asp Tyr Phe Pro Asn Val
            20                  25                  30

Ile Asn Asn Thr Val Glu Lys Gly Asp Tyr Leu Ile Ser Ser Ser Asn
        35                  40                  45

Ile Ala Gly Thr Ile Lys Phe Leu Arg Pro Ile Asn Arg Lys Leu Phe
50                  55                  60

Ile Gln Glu Lys Lys Val Phe Asn Asp Tyr Phe Gln Lys Leu Ile Ile
65                  70                  75                  80

Val Phe Glu Asn Ile Arg Asn Lys Lys Thr Val Thr Glu Glu Asp Lys
                85                  90                  95

Ile Ile Ile Asp Arg Val Ile Tyr Thr Ile Gln Gln Ser Ile Gly Ile
                100                 105                 110

Gly Leu Asp Leu Met Val Asn Gln Asn Ser Ala Arg Lys His Val Gly
            115                 120                 125

Asn Arg Phe Glu Glu Leu Ile Arg Val Ile Phe Thr Glu Ile Ser Val
130                 135                 140

Ser Asn Lys Arg Thr Val Leu Gln Ile Pro Tyr Glu Thr Asp Glu Gly
145                 150                 155                 160

Gln Lys Ile Tyr Lys Cys Glu Asn Asp Leu Ile Ile Ser Pro Phe Glu
                165                 170                 175

Asn Val Glu Ser Thr Asn Lys His Leu Asp Glu Asn Glu Ile Val Val
            180                 185                 190

Ser Ile Lys Thr Thr Ser Lys Asp Arg Met Gly Lys Met Phe Ile Asp
        195                 200                 205

Lys Ile Leu Leu Glu Arg Phe Val Lys His Pro Gln Lys Val Ile Gly
            210                 215                 220

Ile Phe Leu Asn Asp Val Gln Arg Lys Glu Asp Asn Asn Ile Ser Phe
225                 230                 235                 240

Thr Leu Val Ser Gly Leu Phe Met Val Tyr Thr Lys Phe Leu Thr Thr
                245                 250                 255

Leu Glu Gly Ile Tyr Tyr Leu Asp Pro Pro Asn Ala Leu Lys Leu
            260                 265                 270

Pro Tyr Ser Asn His Met Lys Arg Phe Ser Asp Leu Ile Thr Glu Asp
            275                 280                 285

Leu Glu Lys Leu Phe Ser Ser
290                 295
```

(2) INFORMATION FOR SEQ ID NO: 2:

(i) SEQUENCE CHARACTERISTICS:
(A) LENGTH: 885 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO: 2:

```
ATGSTACCAC TGGATAAAGA TTTACAAAAA GCAAAGATTT CAATTACTGA TTTTTTTGAA      60

ATTACAAATA GAGTTTTAGA TTATTTCCCC AATGTAATCA ATAATACAGT TGAAAAAGGA     120
```

```
GATTATTTAA TATCCTCATC AAATATTGCT GGAACAATAA AATTCCTAAG ACCAATCAAT      180

AGAAAGTTAT TTATTCAGGA AAAAAAGTT TTCAATGATT ATTTTCAAAA ACTGATTATA       240

GTTTTTGAAA ATATAAGGAA CAAAAAAACT GTAACAGAGG AAGATAAAAT TATTATTGAT      300

AGGGTAATTT ACACAATACA GCAATCTATT GGAATTGGTT TAGATTTAAT GGTTAATCAA      360

AATAGTGCTA GAAAGCACGT TGGTAACCGA TTTGAAGAAT TAATTAGAGT CATTTTTACA      420

GAAATATCAG TATCGAATAA AAGAACTGTA TTACAAATTC CATATGAAAC TGATGAAGGA      480

CAGAAAATTT ACAAATGCGA GAATGACCTC ATTATTTCTC CTTTTGAAAA TGTAGAATCT     540

ACAAACAAAC ATCTAGATGA AAATGAGATT GTTGTTTCAA TAAAGACAAC ATCAAAAGAT     600

AGGATGGGAA AAATGTTTAT AGATAAAATT TTACTTGAAA GGTTTGTTAA ACACCCTCAA     660

AAAGTTATAG GATTTTCCT CAATGATGTA CAAAGAAAAG AAGACAACAA TATCAGCTTT      720

ACACTTGTTT CAGGATTATT TATGGTGTAT ACTAAATTCT TAACTACTCT TGAAGGGATC    780

TATTATTTAG ATCCACCACC TAATGCATTG AAACTACCAT ATTCTAATCA TATGAAAAGA    840

TTTTCAGATT TAATTACAGA AGACCTTGAA AAATTATTCT CCTCT                    885

(2) INFORMATION FOR SEQ ID NO: 3:

(i) SEQUENCE CHARACTERISTICS:
        (A) LENGTH: 215 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO: 3:

TATGGATATG TTCATAAACA CGCATGTAGG CAGATAGATC TTTGGTTGTG AATCGCAACC      60

AGTGGCCTTA TGGCAGGAGC CGCGGATCAC CTACCATCCC TAATGACCTG CAGGCATGCA    120

AGCTTGCATG CCTGCAGGTC ATTAGGTACG GCAGGTGTGC TCGAGGCGAA GGAGTGCCTG    180

CATGCGTTTC TCCTTGGCTT TTTTCCTCTG GGACA                              215

(2) INFORMATION FOR SEQ ID NO: 4:

(i) SEQUENCE CHARACTERISTICS:
        (A) LENGTH: 215 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO: 4:

TATGTCCCAG AGGAAAAAAG CCAAGGAGAA ACGCATGCAG GCACTCCTTC GCCTCGAGCA      60

CACCTGCCGT ACCTAATGAC CTGCAGGCAT GCAAGCTTGC ATGCCTGCAG GTCATTAGGG    120

ATGGTAGGTG ATCCGCGGCT CCTGCCATAA GGCCACTGGT TGCGATTCAC AACCAAAGAT    180

CTATCTGCCT ACATGCGTGT TTATGAACAT ATCCA                              215

(2) INFORMATION FOR SEQ ID NO: 5:

(i) SEQUENCE CHARACTERISTICS:
        (A) LENGTH: 28 base pairs
        (B) TYPE: nucleic acid
        (C) STRANDEDNESS: single
        (D) TOPOLOGY: linear
```

-continued (ii) MOLECULE TYPE: other nucleic acid
             (A) DESCRIPTION: /desc = "synthetic DNA"

(xi) SEQUENCE DESCRIPTION: SEQ ID NO: 5:

AGATCTAGAG CAAACAAAAA AACCACCG                                                    28

(2) INFORMATION FOR SEQ ID NO: 6:

(i) SEQUENCE CHARACTERISTICS:
             (A) LENGTH: 24 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "synthetic DNA"

(xi) SEQUENCE DESCRIPTION: SEQ ID NO: 6:

GGTCTAGATC CCAGAGGAAA AAAG                                                        24

(2) INFORMATION FOR SEQ ID NO: 7:

(i) SEQUENCE CHARACTERISTICS:
             (A) LENGTH: 100 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "synthetic DNA"

(xi) SEQUENCE DESCRIPTION: SEQ ID NO: 7:

CTCGAGATTT AGGTGACACT ATAGAATACG GAATTGTGAG CGGATAACAA TTCCAAGCTT                 60

CACAGGAAAC AGACCATGGC TTAAGTAACT AGTGAATTCG                                      100

(2) INFORMATION FOR SEQ ID NO: 8:

(i) SEQUENCE CHARACTERISTICS:
             (A) LENGTH: 100 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "synthetic DNA"

(xi) SEQUENCE DESCRIPTION: SEQ ID NO: 8:

CGAATTCACT AGTTACTTAA GCCATGGTCT GTTTCCTGTG AAGCTTGGAA TTGTTATCCG                 60

CTCACAATTC CGTATTCTAT AGTGTCACCT AAATCTCGAG                                      100

(2) INFORMATION FOR SEQ ID NO: 9:

(i) SEQUENCE CHARACTERISTICS:
             (A) LENGTH: 27 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "synthetic DNA"

(xi) SEQUENCE DESCRIPTION: SEQ ID NO: 9:

AATCCCATGG AACGCTACGA ATCTCTG                                                     27

(2) INFORMATION FOR SEQ ID NO: 10:

(i) SEQUENCE CHARACTERISTICS:

(A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO: 10:

CCGGCCATGG TTATTTTTGA CACCAGACC                                              29

(2) INFORMATION FOR SEQ ID NO: 11:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO: 11:

TAACTTGAAT CCATGGGTTC TCACCG                                                 26

(2) INFORMATION FOR SEQ ID NO: 12:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO: 12:

TACTCAGTAG CCATGGCTCT CATAGACCG                                              29

(2) INFORMATION FOR SEQ ID NO: 13:

(i) SEQUENCE CHARACTERISTICS:
        (A) LENGTH: 308 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 13:

Met Asn Glu Ile Ala Phe Asp Asn Tyr Ser Tyr Ile Pro Lys Leu Lys
1               5                   10                  15

Leu Tyr Ser Glu Ile Glu Leu Lys Pro Phe Phe Ile Ser Lys Asn Gly
            20                  25                  30

Ser Leu Phe Asn Val Asp Ala Ile Asp Phe Leu Arg Lys Leu Glu Ser
        35                  40                  45

Asn Ser Val Asp Leu Ile Phe Ala Asp Pro Pro Tyr Asn Ile Lys Lys
    50                  55                  60

Ala Glu Trp Asp Ile Phe Ser Ser Gln Asn Glu Tyr Leu Glu Trp Ser
65                  70                  75                  80

Lys Glu Trp Ile Met Glu Ala His Arg Val Leu Lys Asp Asn Gly Ser
                85                  90                  95

Leu Tyr Val Cys Gly Phe Ser Glu Ile Leu Ala Asp Ile Lys Phe Ile
            100                 105                 110

Thr Ser Lys Tyr Phe His Ser Cys Lys Trp Leu Ile Trp Phe Tyr Arg

```
                115                 120                 125
Asn Lys Ala Asn Leu Gly Lys Asp Trp Gly Arg Ser His Glu Ser Ile
    130                 135                 140

Leu Leu Leu Arg Lys Ser Lys Asn Phe Ile Phe Asn Ile Asp Glu Ala
145                 150                 155                 160

Arg Ile Pro Tyr Asn Glu His Thr Val Lys Tyr Pro Gln Arg Thr Gln
                165                 170                 175

Ala Glu Ser Ser Gln Tyr Ser Asn Ser Lys Lys Gln Tyr Ile Trp Glu
            180                 185                 190

Pro Asn Pro Leu Gly Ala Lys Pro Lys Asp Val Leu Glu Ile Pro Thr
        195                 200                 205

Ile Ser Asn Gly Ser Trp Glu Arg Ser Ile His Pro Thr Gln Lys Pro
    210                 215                 220

Val Glu Leu Leu Lys Lys Ile Ile Leu Ser Ser Ser Asn Lys Asp Ser
225                 230                 235                 240

Leu Ile Leu Asp Pro Phe Gly Gly Ser Gly Thr Thr Tyr Ala Val Ala
                245                 250                 255

Glu Ala Phe Gly Arg Lys Trp Ile Gly Thr Glu Leu Asp Lys Asn Tyr
            260                 265                 270

Cys Leu Glu Ile Gln Lys Arg Leu Lys Asp Glu Ser Met Ile Asn Arg
        275                 280                 285

Ile Phe Ser Gly Asp Asp Asp Ser Asn Ser Gln Asn Arg Arg Lys Lys
    290                 295                 300

Leu Arg Gly Glu
305

(2) INFORMATION FOR SEQ ID NO: 14:

(i) SEQUENCE CHARACTERISTICS:
        (A) LENGTH: 924 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 14:

GTGAATGAAA TAGCGTTTGA TAATTACAGT TATATACCAA AATTAAAACT TTATTCGGAA      60

ATCGAGCTTA AACCATTTTT TATTTCAAAA AACGGTTCAC TTTTCAATGT TGATGCTATT     120

GATTTTTTAA GAAAATTAGA GAGTAATTCT GTGGATTTAA TTTTTGCAGA TCCACCTTAT     180

AACATTAAAA AGGCAGAGTG GGATATTTTT TCTTCTCAAA ATGAATATCT CGAATGGAGT     240

AAAGAATGGA TAATGGAAGC TCATAGAGTT TTAAAAGATA ATGGCAGTTT ATATGTTTGT     300

GGCTTTTCAG AAATTCTGGC AGACATAAAA TTTATCACTT CAAAATATTT TCACAGTTGT     360

AAATGGTTGA TTTGGTTCTA TAGAAACAAG GCAAATTTAG GTAAAGATTG GGACGTTCA      420

CACGAAAGTA TACTGTTATT AAGAAAATCT AAAAATTTTA TTTTTAATAT TGATGAGGCA     480

CGAATCCCGT ATAATGAGCA TACAGTTAAA TATCCACAAA GAACCCAGGC CGAATCTTCG     540

CAATATTCGA ACTCAAAAAA GCAATATATT TGGGAGCCAA ACCCATTAGG AGCTAAGCCA     600

AAAGATGTTT TGGAGATTCC CACAATTTCA AATGGTTCTT GGGAAAGAAG TATTCACCCT     660

ACGCAAAAGC CAGTAGAATT GCTTAAAAAA ATAATTTTAT CTTCATCTAA TAAAGATAGT     720

TTAATTCTTG ATCCATTTGG TGGTTCGGGA ACTACATATG CTGTTGCGGA AGCTTTTGGC     780

AGAAAATGGA TTGGAACAGA GTTAGATAAA AATTATTGTC TGGAAATTCA AAAGCGATTG     840
```

AAAGACGAAA GTATGATCAA CAGGATTTTT TCAGGCGATG ATGATTCAAA TTCTCAAAAT        900

AGAAGAAAAA AATTAAGAGG AGAA        924

(2) INFORMATION FOR SEQ ID NO: 15:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO: 15:

TCGAGATTTA GGTGACACTA TAGAATACA        29

(2) INFORMATION FOR SEQ ID NO: 16:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO: 16:

AGCTTGTATT CTATAGTGTC ACCTAAATC        29

(2) INFORMATION FOR SEQ ID NO: 17:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO: 17:

TCGAGATTTA GGTGACACTA TAGAATACGG AATTGTGAGC GGATAACAAT TCCA        54

(2) INFORMATION FOR SEQ ID NO: 18:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO: 18:

AGCTTGGAAT TGTTATCCGC TCACAATTCC GTATTCTATA GTGTCACCTA AATC        54

(2) INFORMATION FOR SEQ ID NO: 19:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 19:

Met Leu Pro Leu Asp Lys Asp Leu Gln Lys Ala Lys Ile Ser Ile Thr
1               5                   10                  15

Asp Phe Phe Glu
            20

(2) INFORMATION FOR SEQ ID NO: 20:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(ix) FEATURE:
        (A) NAME/KEY: primer_bind
        (B) LOCATION: 1..23
        (D) OTHER INFORMATION: /note= "6, 9, 12 = inosine"

(xi) SEQUENCE DESCRIPTION: SEQ ID NO: 20:

ATGTTNCCNY TNGAYAARGA YYT                                           23

(2) INFORMATION FOR SEQ ID NO: 21:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(ix) FEATURE:
        (A) NAME/KEY: primer_bind
        (B) LOCATION: 1..23
        (D) OTHER INFORMATION: /note= "9 = inosine"

(xi) SEQUENCE DESCRIPTION: SEQ ID NO: 21:

AAGGATTTNC ARAARGCNAA RAT                                           23

(2) INFORMATION FOR SEQ ID NO: 22:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO: 22:

TAAATCTAAA CCAATTCCAA TAGATTGCTG                                    30

(2) INFORMATION FOR SEQ ID NO: 23:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO: 23:

```
TAAATCTAAA CCAATTCCAA TAGATTGCTG                             30

(2) INFORMATION FOR SEQ ID NO: 24:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO: 24:

GAACTGTATT ACAAATTCCA TATGAAACTG                             30

(2) INFORMATION FOR SEQ ID NO: 25:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO: 25:

GACAGAAAAT TTACAAATGC GAGAATGACC                             30

(2) INFORMATION FOR SEQ ID NO: 26:

(i) SEQUENCE CHARACTERISTICS:
        (A) LENGTH: 1588 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 26:

CCATGGCACA CGTTTCAAAA AAGAAATCCT CGAAGTCAAA TATGATGAGA AAAACATCTC     60

AGACATCCTG CATATGACGG TGGATGAAGC ATTGGAATTT TTCTCGGAAA ATCACGAAGA    120

AAAAATTGTA ACCAAACTAA AACCTTTGCA GGACGTTGGT TTGGGTTATC TTCAGTTAGG    180

CCAGTCCTCC TCTACTCTTT CCGGCGGTGA AGCCCAAAGA GTGAAGCTCG CCTCTTTCCT    240

TGTGAAAGGT GTAACGACGG AAAAAACGTT ATTTGTTTTT GATGAACCAT CAACAGGATT    300

ACATTTCCAC GACATTCAAA AATTACTGAA ATCACTTCAG GCACTGATAG AATTAGGGCA    360

TTCGGTTGTA GTGATTGAGC ATCAGCCGGA TATTATCAAA TGCGCCGATT ACATCATCGA    420

TGTCGGACCC AATGCCGGAA AATACGGTGG CGAAATTGTT TTCACAGGAA CTCCGGAAGA    480

TTTGGTAAAA GAGAAAAAGT CGTTTACAGG GAAGTATATT AAGGAGAAGT TAAAGTAATT    540

TATTTATATT TGAAGTTATG CTACCACTGG ATAAAGATTT ACAAAAAGCA AAGATTTCAA    600

TTACTGATTT TTTTGAAATT ACAAATAGAG TTTTAGATTA TTTCCCCAAT GTAATCAATA    660

ATACAGTTGA AAAGGAGAT TATTTAATAT CCTCATCAAA TATTGCTGGA ACAATAAAAT    720

TCCTAAGACC AATCAATAGA AAGTTATTTA TTCAGGAAAA AAAGTTTTC AATGATTATT    780

TTCAAAAACT GATTATAGTT TTTGAAAATA TAAGGAACAA AAAAACTGTA ACAGAGGAAG    840

ATAAAATTAT TATTGATAGG GTAATTTACA CAATACAGCA ATCTATTGGA ATTGGTTTAG    900

ATTTAATGGT TAATCAAAAT AGTGCTAGAA AGCACGTTGG TAACCGATTT GAAGAATTAA    960
```

```
TTAGAGTCAT TTTTACAGAA ATATCAGTAT CGAATAAAAG AACTGTATTA CAAATTCCAT      1020

ATGAAACTGA TGAAGGACAG AAAATTTACA AATGCGAGAA TGACCTCATT ATTTCTCCTT      1080

TTGAAAATGT AGAATCTACA AACAAACATC TAGATGAAAA TGAGATTGTT GTTTCAATAA      1140

AGACAACATC AAAAGATAGG ATGGGAAAAA TGTTTATAGA TAAAATTTTA CTTGAAAGGT      1200

TTGTTAAACA CCCTCAAAAA GTTATAGGGA TTTTCCTCAA TGATGTACAA AGAAAAGAAG      1260

ACAACAATAT CAGCTTTACA CTTGTTTCAG GATTATTTAT GGTGTATACT AAATTCTTAA      1320

CTACTCTTGA AGGGATCTAT TATTTAGATC CACCACCTAA TGCATTGAAA CTACCATATT      1380

CTAATCATAT GAAAAGATTT TCAGATTTAA TTACAGAAGA CCTTGAAAAA TTATTCTCCT      1440

CTTAATTTTT TTCTTCTATT TTGAGAATTT GAATCATCAT CGCCTGAAAA AATCCTGTTG      1500

ATCATACTTT CGTCTTTCAA TCGCTTTTGA ATTTCCAGAC AATAATTTTT ATCTAACTCT      1560

GTTCCAATCC ATTTTCTGCC AAAAGCTT                                        1588

(2) INFORMATION FOR SEQ ID NO: 27:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO: 27:

ATATTTGAAG CCATGGTACC ACTGG                                             25

(2) INFORMATION FOR SEQ ID NO: 28:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO: 28:

GATGATTCAA ATTCTCACCA TGGAAG                                            26

(2) INFORMATION FOR SEQ ID NO: 29:

(i) SEQUENCE CHARACTERISTICS:
        (A) LENGTH: 4146 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 29:

AGATCTGGTC ATCCCAAACA AAAATCTTTC GGTTTACGAA GATGCAGTCG CTTCCTGGAA        60

AGGCGAAAGT ATGAGCGAAT GGAAAAAGGA ATTCATCAAA AAGCCAAAG ATTTCCCAAT       120

TCACAAGCCT TATCATCAAC TCACAAAAGA GCAGAAACAG TTCCTTTGGA AAGGCGATAA      180

AACCAGAAGT TTCCCAAGTA TTGATAATTT TTTCAAAATG CTTGAAGAGA ATCTTTACAA      240

GATCCAATAC CGCGTAATGC TTTCGCGCTA TCGTGGGAAA ACACTTTGCC CCGATTGCGA      300

AGGATTACGA TTGCGGGAAG AAACAAGCTG GGTGAAGATT GACGGACACA ACATTCAGTC      360
```

```
TTTGATTGAA TTACCTTTGG ATGAACTCCT GCCATTGATC AAAAGCTTAA AACTGAACGT    420

CCACGACAGA GAAATTGCCA AACGCCTGAC TTACGAAATC GAAACGAGAT TAGAATTCCT    480

GACGAAAGTC GGCCTTGGAT ATCTGACTTT GAACCGAACA TCCAACACGC TTTCCGGAGG    540

AGAAAGCCAG AGAATCAATC TGGCGACAGC TTGGGAAGTT CGCTGGTTGG TTCTATTTAT    600

ATTTTGGATG AGCCGAGCAT TGGTCTGCAT TCCCGCGATA CAGAAAATCT GATTGGTGTC    660

CTCAAACAAC TCCGCGATTT GGGAANTACC GTGATTGTTG TAGAACACGA CGAAGATGTG    720

ATGCTTGCGG CAGNTTACAT TATAGATATT GGCCCNGNAG CGGGCTACCT TGGTGGCGAT    780

CTTGTTTTCA GCGNGGATTA TAAAGAGATG CTGAAGTNTN ATACTTTAAC CGCAAAATAC    840

CTGAATGGCG AACTGAAAAT AGAAGTTCCT GAAAAACGAA GAAAACCGAA GGAATTCATC    900

GCAATAAAAG GTGCCCGCCA GAATAATTTA AAAAATATTG ACGTTGATGT TCCGTTAGAA    960

TGTCTGACAG TTATCACAGG CGTTTCTGGA AGCGGGAAAT CCACTTTGAT GAAGGAAGTG   1020

ATGACCAATG CCATCCAGAT CCAACTGGGA ATGGGCGGCA AAAAGCCGA TTACGATTCG    1080

GTGGAATTCC CGAAAAAGCT GATCCAGAAT ATCGAACTGA TTGACCAGAA CCCAATCGGG   1140

AAATCGTCCC GCTCCAACCC CGTGACTTAT CTGAAAGCTT ACGACGATAT CCGGGATCTT   1200

TTTGCGAAAC AAAAATCCGC AAAAATCCAG GGTTACAAAC CGAAGCATTT CTCCTTCAAT   1260

GTGGATGGCG AAGATGTGA CGAGTGCAAA GGCGAAGGTA TCATTACCGT ATCAATGCAG    1320

TTTATGGCGG ACATCGAGCT GGAGTGTGAG CATTGCCATG GCACACGTTT CAAAAAGAA    1380

ATCCTCGAAG TCAAATATGA TGAGAAAAAC ATCTCAGACA TCCTGCATAT GACGGTGGAT   1440

GAAGCATTGG AATTTTTCTC GGAAAATCAC GAAGAAAAA TTGTAACCAA ACTAAAACCT    1500

TTGCAGGACG TTGGTTTGGG TTATCTTCAG TTAGGCCAGT CCTCCTCTAC TCTTTCCGGC   1560

GGTGAAGCCC AAAGAGTGAA GCTCGCCTCT TTCCTTGTGA AGGTGTAAC GACGGAAAAA    1620

ACGTTATTTG TTTTTGATGA ACCATCAACA GGATTACATT TCCACGACAT TCAAAAATTA   1680

CTGAAATCAC TTCAGGCACT GATAGAATTA GGGCATTCGG TTGTAGTGAT TGAGCATCAG   1740

CCGGATATTA TCAAATGCGC CGATTACATC ATCGATGTCG ACCCAATGC CGGAAAATAC    1800

GGTGGCGAAA TTGTTTTCAC AGGAACTCCG GAAGATTTGG TAAAAGAGAA AAAGTCGTTT   1860

ACAGGGAAGT ATATTAAGGA GAAGTTAAAG TAATTTATTT ATATTTGAAG TTATGCTACC   1920

ACTGGATAAA GATTTACAAA AAGCAAAGAT TTCAATTACT GATTTTTTTG AAATTACAAA   1980

TAGAGTTTTA GATTATTTCC CCAATGTAAT CAATAATACA GTTGAAAAAG GAGATTATTT   2040

AATATCCTCA TCAAATATTG CTGGAACAAT AAAAATTCCTA AGACCAATCA ATAGAAAGTT   2100

ATTTATTCAG GAAAAAAAAG TTTTCAATGA TTATTTTCAA AAACTGATTA TAGTTTTTGA   2160

AAATATAAGG AACAAAAAAA CTGTAACAGA GGAAGATAAA ATTATTATTG ATAGGGTAAT   2220

TTACACAATA CAGCAATCTA TTGGAATTGG TTTAGATTTA ATGGTTAATC AAAATAGTGC   2280

TAGAAAGCAC GTTGGTAACC GATTTGAAGA ATTAATTAGA GTCATTTTTA CAGAAATATC   2340

AGTATCGAAT AAAAGAACTG TATTACAAAT TCCATATGAA ACTGATGAAG GACAGAAAAT   2400

TTACAAATGC GAGAATGACC TCATTATTTC TCCTTTTGAA AATGTAGAAT CTACAAACAA   2460

ACATCTAGAT GAAAATGAGA TTGTTGTTTC AATAAAGACA ACATCAAAAG ATAGGATGGG   2520

AAAAATGTTT ATAGATAAAA TTTTACTTGA AAGGTTTGTT AAACACCCTC AAAAAGTTAT   2580

AGGGATTTTC CTCAATGATG TACAAAGAAA AGAAGCACAAC AATATCAGCT TTACACTTGT   2640

TTCAGGATTA TTTATGGTGT ATACTAAATT CTTAACTACT CTTGAAGGGA TCTATTATTT   2700
```

```
AGATCCACCA CCTAATGCAT TGAAACTACC ATATTCTAAT CATATGAAAA GATTTTCAGA      2760

TTTAATTACA GAAGACCTTG AAAAATTATT CTCCTCTTAA TTTTTTTCTT CTATTTTGAG      2820

AATTTGAATC ATCATCGCCT GAAAAAATCC TGTTGATCAT ACTTTCGTCT TTCAATCGCT      2880

TTTGAATTTC CAGACAATAA TTTTTATCTA ACTCTGTTCC AATCCATTTT CTGCCAAAAG      2940

CTTCCGCAAC AGCATATGTA GTTCCCGAAC CACCAAATGG ATCAAGAATT AAACTATCTT      3000

TATTAGATGA AGATAAAATT ATTTTTTTAA GCAATTCTAC TGGCTTTTGC GTAGGGTGAA      3060

TACTTCTTTC CCAAGAACCA TTTGAAATTG TGGGAATCTC CAAAACATCT TTTGGCTTAG      3120

CTCCTAATGG GTTTGGCTCC CAAATATATT GCTTTTTTGA GTTCGAATAT TGCGAAGATT      3180

CGGCCTGGGT TCTTTGTGGA TATTTAACTG TATGCTCATT ATACGGGATT CGTGCCTCAT      3240

CAATATTAAA AATAAAATTT TTAGATTTTC TTAATAACAG TATACTTTCG TGTGAACGTC      3300

CCCAATCTTT ACCTAAATTT GCCTTGTTTC TATAGAACCA AATCAACCAT TTACAACTGT      3360

GAAAATATTT TGAAGTGATA AATTTTATGT CTGCCAGAAT TTCTGAAAAG CCACAAACAT      3420

ATAAACTGCC ATTATCTTTT AAAACTCTAT GAGCTTCCAT TATCCATTCT TTACTCCATT      3480

CGAGATATTC ATTTTGAGAA GAAAAAATAT CCCACTCTGC CTTTTTAATG TTATAAGGTG      3540

GATCTGCAAA AATTAAATCC ACAGAATTAC TCTCTAATTT TCTTAAAAAA TCAATAGCAT      3600

CAACATTGAA AAGTGAACCG TTTTTTGAAA TAAAAAATGG TTTAAGCTCG ATTTCCGAAT      3660

AAAGTTTTAA TTTTGGTATA TAACTGTAAT TATCAAACGC TATTTCATTC ACAAATGAAT      3720

CAATCTGCTG TTGTGTATAA ACCCTGTAAT TATTAATAGG ATGTCTTAAA CTTTTGAATT      3780

TTCCAGAATT ATCCCATCTT CCTTAATGTC TCAGAGTTAA CATCTAATAA TTTCGCCGCT      3840

TCTTTTATTG ATAAATAATC ATCCATATCT TACACAACAT TACACAAGTT TATACAGCAA      3900

ATATAAATAT TTTTTATACA TTGTAAAAAT TTTATTTACT TTTATTTTGT TCAATTGTCT      3960

CAATAAATAG TTAATCGAAA TACATTTTGA ATATGATAAA ATTGACTCCA ACAAATCTAA      4020

CACAATGACA TTAAAACCAA TAAAAACGGA AGAAGATTAC AATCAGGTTT TAGAAAGACT      4080

TTCACAAATT TTCGACGCTA AACCAAATAC CAAAGATGGA GATGAATTGG GAAATCTTGG      4140

GAATTC                                                                4146

(2) INFORMATION FOR SEQ ID NO: 30:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 30:

ATTTAGGTGA CACTATAGAA TAC                                              23

(2) INFORMATION FOR SEQ ID NO: 31:

(i) SEQUENCE CHARACTERISTICS:
        (A) LENGTH: 49 base pairs
        (B) TYPE: nucleic acid
        (C) STRANDEDNESS: double
        (D) TOPOLOGY: linear (ii) MOLECULE TYPE: other nucleic acid (xi) SEQUENCE DESCRIPTION: SEQ ID NO: 31:

AAGCTCGAGT CTGATGACGA AGCTTGACTG ACTGAGATCA GCTTGCAAC                  49
```

```
(2) INFORMATION FOR SEQ ID NO: 32:

(i) SEQUENCE CHARACTERISTICS:
        (A) LENGTH: 35 base pairs
        (B) TYPE: nucleic acid
        (C) STRANDEDNESS: double
        (D) TOPOLOGY: linear (ii) MOLECULE TYPE: other nucleic acid (xi) SEQUENCE DESCRIPTION: SEQ ID NO: 32:

CTCGAGATTT AGGTGACACT ATAGAATACA AGCTT                              35

(2) INFORMATION FOR SEQ ID NO: 33:

(i) SEQUENCE CHARACTERISTICS:
        (A) LENGTH: 60 base pairs
        (B) TYPE: nucleic acid
        (C) STRANDEDNESS: double
        (D) TOPOLOGY: linear (ii) MOLECULE TYPE: other nucleic acid (xi) SEQUENCE DESCRIPTION: SEQ ID NO: 33:

CTCGAGATTT AGGTGACACT ATAGAATACG GAATTGTGAG CGGATAACAA TTCCAAGCTT   60
```

GENE ISOLATION METHOD

This application is a divisional of co-pending application Ser. No. 08/952,089, filed on Nov. 10, 1997, now U.S. Pat. No. 6,165,749, which is the national stage of PCT International Application No. PCT/JP97/00748 filed on Mar. 10, 1997 under 35 U.S.C. 371. The entire contents of each of the above-identified applications are hereby incorporated by reference.

TECHNICAL FIELD

The present invention relates to a plasmid vector usable in genetic recombinant technology and to a method for expressing a gene by using the plasmid vector. The present invention also relates to a method for isolating a desired gene by using such a plasmid vector. In addition, the present invention relates to a restriction enzyme and a gene thereof available as a genetic engineering reagent, in more detail to the AccIII restriction endonuclease and a DNA coding therefor.

BACKGROUND ART

In constructing an expression system for a desired gene by genetic recombinant technology, expression of the gene is controlled by bringing it under control of a promoter recognized by the RNA polymerase of the host used. In the case of a gene encoding a protein harmful to the host, however, plasmid construction itself is sometimes hampered by expression of the product of the gene due to the inability to stringently control the expression of the promoter used.

As an expression system resolving that problem, the pET system (produced by Novagen) has been developed, which uses the RNA polymerase of the bacteriophage T7, which infects *Escherichia coli*, with *Escherichia coli* as a host [journal of Molecular Biology, Vol. 189, pp. 113–130 (1986); Gene, Vol. 56, pp. 125–135 (1987)]. The pET system is a system that allows T7 RNA polymerase, which has high promoter recognition specificity and high transcription activity, to be expressed in *Escherichia coli*, which T7 RNA polymerase transcribes a desired gene placed downstream of the T7 promoter on an expression vector and causes high expression of the gene. Because transcription of the desired gene occurs in the presence of T7 RNA polymerase, plasmid construction in the host is possible without expressing the desired gene, provided that the host does not produce the polymerase; plasmid construction itself is never hampered, as in cases where the expression system is constructed, while the desired gene is kept under control of a promoter recognized by the RNA polymerase of the host.

However, because the T7 RNA polymerase gene has been cloned onto the λ-phage vector and lysogenized into the expression host, there is no freedom of host choice; painstaking procedures are needed if the host is changed. In addition, because the expression of T7 RNA polymerase in the host is not stringently controlled, T7 RNA polymerase is expressed even when the host is in a non-inductive condition, resulting in expression of the desired gene placed downstream of the T7 promoter on the expression vector even in a non-inductive condition. To suppress such expression of the desired gene in a non-inductive condition, T7 RNA polymerase activity is inhibited using T7 lysozyme, a T7 RNA polymerase inhibitor [Journal of Molecular Biology, Vol. 219, pp. 37–44 (1991)], or T7 RNA polymerase is prevented from getting access to the T7 promoter by placing a lactose operator downstream of the T7 promoter [Journal of Molecular Biology, Vol. 219, pp. 45–59 (1991)].

However, even these countermeasures are unsatisfactory in terms of effect against T7 RNA polymerase of high transcription activity so that the activity of T7 RNA polymerase in a non-inductive condition cannot be completely inhibited. For this reason, if the desired gene product is lethal to the host, it is impossible in some cases to prepare a transformant for expression of the gene, even when plasmid construction is possible. In other words, the pET system involves two problems to be resolved: one of the inability to freely change the host, and the other of inaccurate control of T7 RNA polymerase expression.

On the other hand, there is a bacteriophage having characteristics similar to those of the bacteriophage T7, known as the bacteriophage SP6 [Science, Vol. 133, pp. 2069–2070 (1961)], which infects *Salmonella typhimurium*. The RNA polymerase produced by the bacteriophage SP6, a single peptide having a molecular weight of about 100,000, is commonly used for in vitro RNA synthesis since it possesses high promoter recognition specificity and high transcription activity [Journal of Biological Chemistry, Vol. 257, pp. 5772–5778 (1982); Journal of Biological Chemistry, Vol. 257, pp. 5779–5788 (1982)]. In addition, the SP6 RNA polymerase gene has already been cloned and expressed in large amounts in *Escherichia coli* [Nucleic Acids Research, Vol. 15, pp. 2653–2664 (1987)].

Genes whose expression product acts lethally on hosts are exemplified by restriction endonuclease genes. Essentially, restriction endonucleases are utilized for self-defense by cleaving phages and other exogenous DNA entering the cells of microorganisms that produce the restriction endonucleases. On the other hand, microorganisms that produce restriction endonucleases mostly produce modification enzymes that recognize the same base sequences as those of the restriction endonucleases, to protect their own DNA against cleavage by the restriction endonucleases. Specifically, a modification enzyme modifies DNA by adding a methyl group to one or more bases in the base sequence recognized thereby, to make it impossible for the restriction endonuclease that recognizes the same sequence as that of the modification enzyme to bind thereto or to cleave the DNA. This mechanism is called restriction modification system, and the pair of genes of the restriction endonuclease and modification enzyme that constitute the restriction modification system called restriction modification system gene. Therefore, when the restriction endonuclease gene is expressed in a microorganism lacking a modification enzyme gene from the restriction modification system gene, the microorganism's DNA is cleaved, resulting in cell death. In fact, there are two modification enzyme genes in the MboI restriction modification system gene; it has been reported that cloning of restriction endonuclease genes is impossible due to incomplete modification of the host DNA in the case of incomplete methylation in the co-presence of either modification enzyme gene alone [Nucleic Acids Research, Vol. 21, pp. 2309–2313 (1993)].

Also, it has been demonstrated that if a restriction modification system gene is lost from a cell retaining the restriction modification system gene, a lack of modification activity in the cell results in incomplete methylation of genomic DNA, which in turn causes lethal cleavage of its own genomic DNA by a very small amount of restriction endonuclease remaining therein [Science, Vol. 267, pp. 897–899 (1995)]. In summary, in the absence of modification enzymes that constitute a restriction modification system, restriction endonucleases behave as proteins very harmful to cells; separate cloning and expression of their genes have been impossible by prior art technologies.

Concerning restriction endonucleases, restriction endonucleases can be classified by their enzymatic properties into three types: I, II and III. Type II restriction endonucleases, in particular, each of which recognizes a particular DNA base sequence and cleaves it at a particular site in or near the sequence, are extensively used in the field of genetic engineering, and restriction endonucleases of this type with various specificities have been isolated from a variety of microorganisms [Nucleic Acids Research, Vol. 24, pp. 223–235 (1996)]. In the present specification, a type II restriction endonuclease is hereinafter referred to as "restriction endonuclease". It should be noted, however, that some microorganisms produce only small amounts of restriction endonuclease, and others produce a plurality of restriction endonucleases. For example, the restriction endonuclease AccIII is produced by *Acinetobacter calcoaceticus* (hereinafter referred to as Acc bacterium), which has been deposited under accession number FERM BP-935 at the National Institute of Bioscience and Human-Technology, Agency of Industrial Science and Technology, Ministry of International Trade and Industry [address: 1–3, Higashi 1-chome, Yatabemachi, Tsukuba-gun, Ibaraki, 305, Japan] since Nov. 9, 1985 (date of original deposition), but the amount of the enzyme produced is small and this microorganism also produces the restriction endonucleases AccI and AccII simultaneously. Therefore, advanced production technology is needed to provide the restriction endonuclease AccIII as a reagent of high purity and low cost using this microorganism. In providing a restriction endonuclease as a reagent of high purity and low cost, it is effective to isolate the desired restriction endonuclease gene and selectively produce the desired restriction endonuclease in large amounts by genetic engineering technology. To accomplish this purpose, some methods of isolating restriction endonuclease genes have been reported.

First, there may be mentioned the "shotgun" method, wherein the genomic DNA of a microorganism that produces a restriction endonuclease is cleaved using the appropriate restriction endonuclease, the resulting fragment is inserted into an appropriate plasmid vector, and a clone expressing the restriction endonuclease gene is selected. Screening methods for desired clones are exemplified by a method wherein a restriction modification system gene is isolated with resistance to phage infection as an index, on the basis of the self-defence function acquired by the host upon introduction of the restriction modification system gene thereinto [PstI: Proceedings of the National Academy of Science of the USA, Vol. 78, pp. 1503–1507 (1981)]. This method, however, necessitates that the size of the restriction modification system gene falls within a range allowing its isolation, and that the expression of the restriction modification system gene isolated exhibits sufficient phage resistance to allow the selective survival of the host. On the other hand, as a general feature of restriction modification system genes, there may be mentioned the close location on the genome of restriction endonuclease genes and modification enzyme genes; in fact, this has been confirmed in many restriction modification system genes that have so far been obtained [Nucleic Acids Research, Vol. 19, pp. 2539–2566 (1991)]. Accordingly, there is a method wherein a restriction modification system gene is screened for with the expression of a modification enzyme gene as an index on the basis of the above-described feature [Japanese Patent Laid-Open No. 63-87982; Nucleic Acids Research, Vol. 19, pp. 1831–1835 (1991)]. When the restriction endonuclease gene is not close to the modification enzyme gene, however, this method fails to yield the restriction endonuclease gene.

Furthermore, the above-described "shotgun" method poses a fundamental problem associated with a difference in transcription-translation mechanism between the genomic DNA source organism and the host. For example, in the case of insufficient gene expression due to the failure of the promoter and ribosome binding site accompanying the restriction modification system gene to function well in the host, much labor is needed to select transformants containing the desired gene, even if obtained. To avoid this drawback, there is a method wherein the amino acid sequence of the restriction endonuclease protein is analyzed, the restriction endonuclease gene is obtained from the genomic DNA of a microorganism that produces the restriction endonuclease by PCR-based DNA amplification on the basis of the sequence data obtained, and wherein a known protein expression system is utilized [Japanese Patent Laid-Open No. 6-277070]. Because the presence of a restriction endonuclease is lethal to the host in conventional protein expression systems, there is a need to protect the host by, for example, allowing a modification enzyme that constitutes a restriction modification system together with the enzyme to be co-present.

Although all the above-described methods of the isolation of restriction endonuclease genes necessitate the simultaneous isolation of the restriction endonuclease gene and a modification enzyme gene that constitutes a restriction modification system gene together with the gene, another method of isolating the restriction endonuclease gene alone has been reported [Nucleic Acids Research, Vol. 22, pp. 2399–2403 (1994)]. In that method, however, it is intended to isolate a gene encoding a restriction endonuclease for which optimal temperature for enzyme activity is around 70° C.; the co-presence of a modification enzyme gene is necessary when the gene to be isolated encodes a restriction endonuclease showing high specific activity near host culturing temperature.

Exceptionally, there are restriction endonucleases that do not show cleavage activity unless a particular nucleic acid base in their DNA recognition sequence has not been modified by methylation, like the restriction endonuclease DpnI. Genes for restriction endonucleases possessing this property are thought to be exceptional in that they can be isolated even in the absence of another particular gene by selecting the appropriate host organism. In fact, the mrr gene has been isolated, which encodes the Mrr protein, which is not a type II restriction endonuclease but which recognizes a particular DNA base sequence containing a methylated nucleic acid base and exhibits DNA cleavage activity [Journal of Bacteriology, Vol. 173, pp. 5207–5219 (1991)].

As stated above, isolation of a restriction endohuclease gene by the prior art necessitates the simultaneous expression of the gene and a modification enzyme gene that constitutes a restriction modification system gene together with the gene, except for special cases.

DISCLOSURE OF THE INVENTION

Therefore, a first object of the present invention provides a plasmid vector capable of isolating such a gene that an isolation thereof or a construction of an expression system thereof has been difficult in the prior arts because the gene product is lethal or harmful to a host, and capable of introducing into a host to express the protein efficiently. A second object of the present invention provides a method for expressing a desired gene by using this plasmid vector. A third object of the present invention provides a method for isolating a desired gene by using this plasmid vector, especially for isolating a restriction endonuclease gene without co-existence of a modification enzyme gene constituting a restriction modification system. A fourth object of the present invention provides a polypeptide possessing an activity of an AccIII restriction endonuclease. In addition, a fifth object of the present invention provides a DNA which encodes a polypeptide possessing an activity of an AccIII restriction endonuclease.

First, to resolve the problems in the pET system, the present inventors have constructed an expression system using SP6 RNA polymerase as a new accurate expression control expression system, and assessed the system.

Because the expression system is constructed using a system plasmid inserted the SP6 RNA polymerase gene into the miniF plasmid, expression systems for the desired gene can be constructed in various strains of Escherichia coli by simultaneously introducing an expression vector harboring the desired gene cloned downstream of the SP6 promoter and this system plasmid into the host. In addition, using the lac promoter and antisense technology, the present inventors made it possible to exactly control the expression of the SP6 RNA polynerase gene on the system plasmid. Assessing this expression system using the β-galactosidase gene as a reporter gene demonstrated that the expression of the SP6 RNA polymerase gene is accurately controlled in this system, that there is almost no expression of SP6 RNA polymerase in a non-inductive condition, and that induction is followed by the expression of a sufficient amount of SP6 RNA polymerase to efficiently express the desired gene and subsequent expression of the desired gene at a high level.

It was also shown, however, that when the host used is Escherichia coli, the desired gene downstream of the SP6 promoter is expressed in very small amounts even in a non-inductive condition because the SP6 promoter is very weakly but actually recognized by Escherichia coli RNA polymerase. It was thus proven that when the gene product acts very harmfully and lethally to Escherichia coli, expression system construction is impossible so that the object of the present invention cannot be accomplished well.

With these findings in mind, the present inventors have made further extensive investigation and unexpectedly found that (i) expression of the desired gene in a non-inductive condition can be suppressed to undetectable levels, and that (ii) expression induction increases the copy number of the plasmid containing the desired gene and causes RNA polymerase expression, resulting in the transcription and translation of the desired gene placed downstream of a promoter recognized by the RNA polymerase, by using a new system for controlling the expression of the desired gene by means of a combination of two control methods, i.e., control of the copy number of the gene, and transcription control via the promoter. In other words, the plasmid vector of the present invention is a plasmid vector having unique features to resolve the above problems in the field of genetic engineering. The present inventors made further investigation based on this finding, and developed a method for expressing the desired gene using the vector.

The present inventors also have developed a method for isolating a gene whose expression product acts lethally on the host, using the above-described plasmid vector, more specifically a method of isolating a restriction endonuclease gene without the drawbacks of the prior art.

The present inventors also found it possible to isolate DNA encoding the AccIII restriction endonuclease, which had not been obtained so far, without the co-presence of an AccIII modification enzyme, and express the AccIII restriction endonuclease in large amounts, using the above-described method.

(1) The gist of the present invention is concerned with:
A plasmid vector characterized by comprising a promoter sequence to control an expression of a desired gene, the promoter sequence being recognized by an RNA polymerase not inherent to a host, and a replication origin for increasing a copy number by induction with an exogenous factor;

(2) The plasmid vector described in item (1) above, wherein the promoter sequence is recognized by RNA polymerases derived from bacteriophages;

(3) The plasmid vector described in item (2) above, wherein the promoter sequence is recognized by an RNA polymerase derived from SP6 phage;

(4) The plasmid vector described in item (3) above, wherein the promoter sequence contains the base sequence of SEQ ID NO:30 in the Sequence Listing;

(5) The plasmid vector described in any one of items (1) to (4) above, wherein the replication origin is under control of a promoter;

(6) The plasmid vector described in any one of items (1) to (5) above, wherein the replication origin is under control of the lac promoter;

(7) The plasmid vector described in any one of items (1) to (6) above, comprising a drug resistance gene as a selection marker;

(8) The plasmid vector described in item (7) above, which is selected from pACE601, pACE611, pACE701 and pACE702;

(9) A plasmid vector in which a desired gene to be expressed is incorporated into the plasmid vector described in any one of items (1) to (8) above;

(10) A method for expressing a desired gene, characterized by introducing into a host a plasmid vector in which the desired gene is incorporated into the plasmid vector described in any one of items (1) to (8) above, and an RNA polymerase gene which recognizes a promoter sequence in the plasmid vector, and inducing an increase in a copy number of the plasmid vector and an expression of the RNA polymerase by using an exogenous factor to transcribe and translate the desired gene;

(11) The method for expressing a desired gene described in item (10) above, characterized in that the increase in the copy number of the plasmid vector and the expression of the RNA polymerase are induced by respective exogenous factors;

(12) The method for expressing a desired gene described in item (10) above, characterized in that the increase in the copy number of the plasmid vector and the expression of the RNA polymerase are induced by a same exogenous factor;

(13) The method for expressing a desired gene described in any one of items (10) to (12) above, wherein the exogenous factor which induces the increase in the copy number of the plasmid vector, is one or more selected from the group consisting of an addition of isopropyl-β-D-thiogalactoside (IPTG), an addition of lactose, an addition of galactose, an addition of arabinose, a reduction of a tryptophane concentration and an adjustment of a transformant cultivation temperature;

(14) The method for expressing the desired gene described in any one of items (10) to (12) above, wherein the exogenous factor which induces the expression of the RNA polymerase, is one or more selected from the group consisting of an addition of isopropyl-β-D-thiogalactoside (IPTG), an addition of lactose, an addition of galactose, an addition of arabinose, a reduction of a tryptophane concentration and an adjustment of a transformant cultivation temperature;

(15) The method for expressing a desired gene described in item (10) above, characterized in that the RNA polymerase gene is introduced into the host by the other plasmid vector or a phage vector;

(16) The method for expressing a desired gene described in item (10) above, characterized in that the RNA polymerase gene is incorporated into a chromosome of the host;

(17) The method for expressing a desired gene described in item (15) or item (16) above, characterized in that the RNA polymerase gene is derived from SP6 phage;

(18) The method for expressing a desired gene described in any one of items (10) to (17) above, wherein the desired gene encodes a protein lethal or harmful to the host;

(19) The method for expressing a desired gene described in any one of items (10) to (18) above, characterized in that *Escherichia coli* is used as the host;

(20) A method for isolating a desired gene, characterized in that the plasmid vector described in any one of items (1) to (8) above is employed in the method for isolating the desired gene;

(21) The method for isolating a desired gene described in item (20) above, wherein the desired gene encodes a protein lethal or harmful to a host;

(22) The method for isolating a desired gene described in item (21) above, wherein the gene encoding a protein lethal or harmful to the host is a restriction endonuclease gene;

(23) A polypeptide containing the entire or a portion of the amino acid sequence shown by SEQ ID NO:1 in the Sequence Listing, and possessing an activity of AccIII restriction endonuclease;

(24) A polypeptide having an amino acid sequence resulting from at least one of deletion, addition, insertion or substitution of one or more amino acid residues in the amino acid sequence of SEQ ID NO:1 in the Sequence Listing or a portion thereof, and possessing an activity of AccIII restriction endonuclease;

(25) A DNA encoding a polypeptide which contains the entire or a portion of the amino acid sequence shown by SEQ ID NO:1 in the Sequence Listing, and possesses an activity of AccIII restriction endonuclease;

(26) A DNA containing the entire or a portion of the DNA shown by SEQ ID NO:2 in the Sequence Listing wherein an expression product of the DNA possesses an activity of AccIII restriction endonuclease;

(27) A DNA encoding a polypeptide resulting from at least one of deletion, addition, insertion or substitution of one or more amino acid residues in the amino acid sequence of SEQ ID NO:1 in the Sequence Listing or a portion thereof, and possessing an activity of AccIII restriction endonuclease; and

(28) A DNA capable of hybridizing to the DNA described in any one of items (25) to (27) above, and encoding a polypeptide possessing an activity of AccIII restriction endonuclease.

BEST MODE FOR CARRYING OUT THE INVENTION

Figure 1:
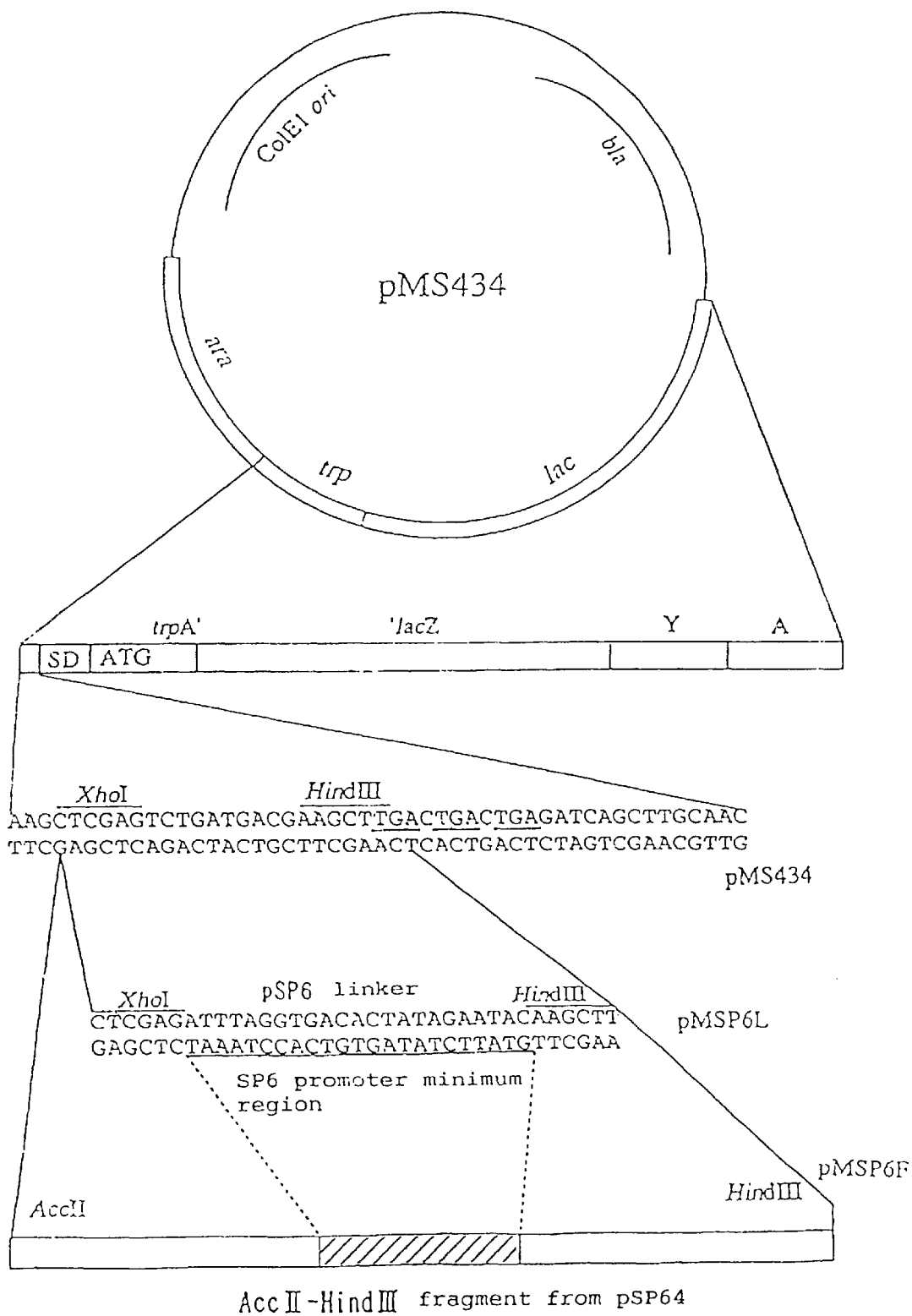
FIG. 1 shows the constitution of the model expression plasmids pMSP6L and pMSP6F. MS434 contains in part DNA having the DNA sequence identified as SEQ ID NO:31. pMS6L contains in part DNA having the DNA sequence identified as SEQ ID NO:32.

The first aspect of the present invention relates to a plasmid vector. More specifically, it relates to a plasmid vector characterized in that the plasmid vector comprises a promoter sequence, which is recognized by an RNA polymerase not inherent to the host, to control the expression of the desired gene, and a replication origin for increasing the copy number by induction with an exogenous factor. The promoter sequence contained in the plasmid vector, which sequence controls the expression of the desired gene, may be any promoter sequence; promoter sequences recognized by particular RNA polymerases, e.g., those recognized by RNA polymerases derived from the T7, T3, SP6 and other bacteriophages, can be used, with preference given to those recognized by the RNA polymerase derived from the SP6 phage. The base sequence of the minimum region of the promoter recognized by the RNA polymerase derived from the SP6 phage, i.e., the SP6 promoter, is shown by SEQ ID NO:30 in the Sequence Listing. Furthermore, the plasmid vector may have a drug resistance gene used as a selection marker.

Exogenous factors that control the copy number of the plasmid vector of the present invention, i.e., the function of the replication origin of the plasmid vector, include, but are not limited to, for example, the addition of various chemicals, such as lactose or structurally related substances like isopropyl-β-D-thiogalactoside (IPTG), galactose or structurally related substances, and arabinose or structurally related substances; reduction of tryptophane concentration; and adjustment of transformant cultivation temperature. By bringing the replication origin under control of a promoter that can be controlled by these factors, copy number control becomes possible. Promoters usable for this purpose include, but are not limited to, the lac, trp, tac, gal, ara and $P_L$ promoters etc. when the host used is *Escherichia coli*, as long as the above-described purpose is accomplished. These promoters can also be used to induce the expression of an RNA polymerase gene.

Examples of the replication origin of the plasmid vector of the present invention include, but are not limited to, plasmid vectors that serve as replication origins of runaway plasmids under control of the lac promoter. In this case, copy number control is achieved by the addition of lactose and structurally related substances, most preferably by the addition of isopropyl-β-D-thiogalactoside (IPTG).

The second aspect of the present invention relates to a method for expressing a desired gene to be expressed, characterized by introducing a plasmid vector prepared by incorporating the desired gene into the plasmid vector of the present invention, and an RNA polymerase gene that recognizes the promoter sequence on the plasmid vector, into a host, and inducing an increase in the copy number of the plasmid vector and the expression of the RNA polymerase with an exogenous factor to transcribe and translate the desired gene. RNA polymerase genes that recognize the promoter sequence on the plasmid vector include, but are not limited to, for example, the RNA polymerase genes derived from the above-mentioned bacteriophages, with preference given to the RNA polymerase gene derived from the SP6 phage. Exogenous factors that induce the expression of such RNA polymerase or an increase in the copy number of the plasmid vector include, but are not limited to, for example, the addition of various chemicals, such as lactose or structurally related substances like isopropyl-β-D-thiogalactoside (IPTG), galactose or structurally related substances, and arabinose or structurally related substances; the reduction of tryptophane concentration; and the adjustment of transformant cultivation temperature.

Induction of an increase in the copy number of plasmid vector and that of expression of RNA polymerase may be achieved by the action of respective exogenous factors or a same exogenous factor. Also, in this case, the gene encoding RNA polymerase may be incorporated onto a chromosome of the host, or introduced into the host by a plasmid vector other than the plasmid vector of the present invention or a phage vector. In the latter case, the host can readily be changed according to the purpose. In that case, introduction of the vector having an RNA polymerase gene into the host may precede or follow the introduction of the plasmid vector of the present invention.

Although the desired gene in the present invention is not subject to limitation, it is meaningful when it encodes a protein lethal or harmful to the host. Such proteins include, for example, the above-mentioned restriction endonucleases, other nucleases, nucleic acid-binding proteins, and proteases.

The present invention provides a system that controls the expression of a desired gene by a combination of two control methods, i.e., control of the copy number of the gene, and control of transcription via a promoter, as described above. Control of the expression of the desired gene cloned onto a plasmid in the present invention, unlike conventional control, is very stringent so that its expression can be suppressed to an undetectable level in a non-inductive condition. When the copy number of the plasmid, i.e., the copy number of the desired gene, is increased, with concurrent expression of RNA polymerase, by expression induction, the desired gene is transcribed and translated under control of the promoter by the action of the RNA polymerase.

It is therefore possible to use the plasmid vector of the present invention to prepare a transformant containing a gene harmful or lethal to the host and express the gene, a task difficult to achieve by the prior art.

For example, when cloning of a gene encoding the Nsp7524 III restriction endonuclease was attempted using the plasmid vector of the present invention, the gene was successfully retained in *Escherichia coli* without co-presence of the corresponding modification enzyme gene. It was also possible to express the Nsp7524 III restriction endonuclease in the cells of the resulting transformant by introducing a system plasmid containing an RNA polymerase gene into the transformant to induce the expression of the Nsp7524 III restriction endonuclease.

Also, using the plasmid vector of the present invention as a cloning vector for preparation of a gene library, it is possible to isolate a gene that cannot be isolated by a conventional method, and confirm the activity of its expression product in a single host. The use of the plasmid vector of the present invention is of course not limited to the cloning of a gene encoding a product harmful to the host, and can be used as a general-purpose plasmid vector.

An RNA polymerase gene relating to the present invention can be introduced into a host using, for example, the plasmid pFSP6 and the phage M13sp6. Details of construction of the plasmid pFSP6 are shown in Reference Example (2). *Escherichia coli* HB101 as transformed with the plasmid, designated *Escherichia coli* HB101/pFSP6, has been deposited under accession number FERM BP-5742 at the National Institute of Bioscience and Human-Technology, Agency of Industrial Science and Technology, Ministry of International Trade and Industry [address: 1–3, Higashi 1 chome, Tsukuba-shi, Ibaraki-ken, 305, Japan] since Dec. 22, 1995 (date of original deposition). A method for the construction of the phage M13sp6 is described in Example 2 (6).

The present invention is hereinafter described in more detail with reference to a case using the plasmid pFSP6.

First described are the results of an experiment conducted using the constructed multicopy model expression plasmids pMSP6L, pMSP6F (FIG. 1) and pMSP6O (FIG. 2), all having a promoter sequence recognized by SP6 RNA polymerase and the β-galactosidase gene as a reporter gene, and all allowing the expression of the desired gene using the above-described system plasmid pFSP6.

Details of construction of these model expression plasmids are shown in Reference Example (3). These plasmids incorporate the minimum region of the SP6 promoter (pMSP6L), a inherent SP6 promoter region (pMSP6F), or both the minimum region of the SP6 promoter and the lac operator region (pMSP6O), respectively, as an SP6 plasmid sequence.

When the plasmid pMSP6L or pMSP6F alone was introduced into the *Escherichia coli* strains shown in Table 1, β-galactosidase activity was noted, despite the fact that the host *Escherichia coli* did not express SP6 RNA polymerase, the amounts being higher than that obtained with the plasmid pMS434, which does not have the SP6 promotor, as shown in Table 2. In short, it can be conjectured that the SP6 promoter is recognized by the RNA polymerase derived from *Escherichia coli*, and that the β-galactosidase gene downstream thereof is transcribed and translated. Also, when *Escherichia coli* MRi80, a strain that has a mutation in the pcnB gene and wherein the copy number of a plasmid having a replication origin derived from ColE1, like the above-described model of expression plasmids, is reduced by 1/6 to 1/13 of that of the parent strain MRi7, was used as a host, the β-galactosidase activity was also decreased to 1/7 to 1/14 of that of MRi7. This suggests a correlation between the β-galactosidase gene expression level and the copy number of the plasmid introduced.

TABLE 1

| Strain | Genotype | Origin/Reference |
|---|---|---|
| MC4100 | F-, araD139, Δ(argF-lac)U169, thiA, rpsL150, relA1, flbB5301, deoC1, ptsF25, rbsR | Casadaban et al. J. Mol. Biol. 104(1976) 541–555. |
| MRi7 | MC4100Δrbs-7 | Lopilato et al. J. Bacteriol. 158(1984) 665–673 |
| MRi80 | MRi7 pcnB80 | Lopilato et al. Mol. Gen. Genet. 205(1986) 285–290. |

TABLE 2

| | β - Galactosidase Activity Plasmid | | |
|---|---|---|---|
| Strain | pMSP6F | pMSP6L | pMS434 |
| MC4100 | 202 | 242 | 30 |
| MRi7 | 234 | 287 | 23 |
| MRi80 | 17 | 27 | 4 |

Next, when the same model of expression plasmids were introduced into *Escherichia coli* together with the above-described system plasmid pFSP6 and β-galactosidase activity was determined under conditions such that the expression of the SP6 RNA polymerase gene was not induced, the β-galactosidase activity was at most as high as that obtained with *Escherichia coli* not containing the system plasmid, as shown in Table 3. This demonstrates that the expression of the SP6 RNA polymerase gene on the plasmid pFSP6 is almost completely suppressed in a non-inductive condition.

On the other hand, when the expression of the SP6 RNA polymerase gene was induced by the addition of isopropyl-β-D-thiogalactoside (IPTG), β-galactosidase activity was increased by 18 to 32 times, demonstrating that the β-galactosidase gene can be expressed via the SP6 promoter. When the host used was *Escherichia coli* MRi80, in particular, β-galactosidase activity was increased to a level 25 to 32 times that obtained in a non-inductive condition, 4 hours after induction, though the activity in a non-inductive condition remained at a very low level.

TABLE 3

| | β - Galactosidase Activity (Non-Induction/Induction) | | | | | |
|---|---|---|---|---|---|---|
| | pMSP6F | | pMSP6L | | pMS434 | |
| Strain | Non-Induction | Induction | Non-Induction | Induction | Non-Induction | Induction |
| MC4100 (pFSP6) | 221 | 4875 | 234 | 5256 | 25 | 19 |
| MRi7 (pFSP6) | 220 | 3958 | 242 | 4243 | 25 | 21 |
| MRi80 (pFSP6) | 17 | 425 | 30 | 970 | 3 | ND |

In the plasmid pMSP6O, which carries the lac operator sequence downstream of the SP6 promoter, the β-galactosidase activity under non-inductive conditions is lower than that in other model expression plasmids; however, its expression cannot be suppressed completely. These results suggest that the expression of the desired gene is difficult to completely suppress in an expression system using a multicopy plasmid, and that controlling the copy number of the plasmid containing the desired gene is more effective in resolving this problem than controlling the expression of the RNA polymerase gene on the system plasmid.

The present inventors thus made further investigation based on these results to explore a new expression vector, and developed the plasmid vector of the present invention.

Specifically, the present inventors constructed a runaway plasmid vector capable of reducing the expression level in a non-inductive condition to ensure sufficient expression after induction. First, in consideration of the fact that SP6 RNA polymerase expression in a system plasmid is induced by IPTG, a plasmid having a runaway replication origin allowing an increase in copy number by IPTC induction was constructed in accordance with the procedures shown in FIG. 3. First, the plasmid pUC106AdPO is constructed by removing the PvuII fragment containing the lac promoter and the operator region from the plasmid pUC106A, which is obtained by introducing the 106 NdeI DNA fragment prepared from the two DNA strands whose base sequences are shown by SEQ ID NO:3 and SEQ ID NO:4 in the Sequence Listing into the NdeI site of the plasmid vector pUC19 (produced by Takara Shuzo).

Figure 4:
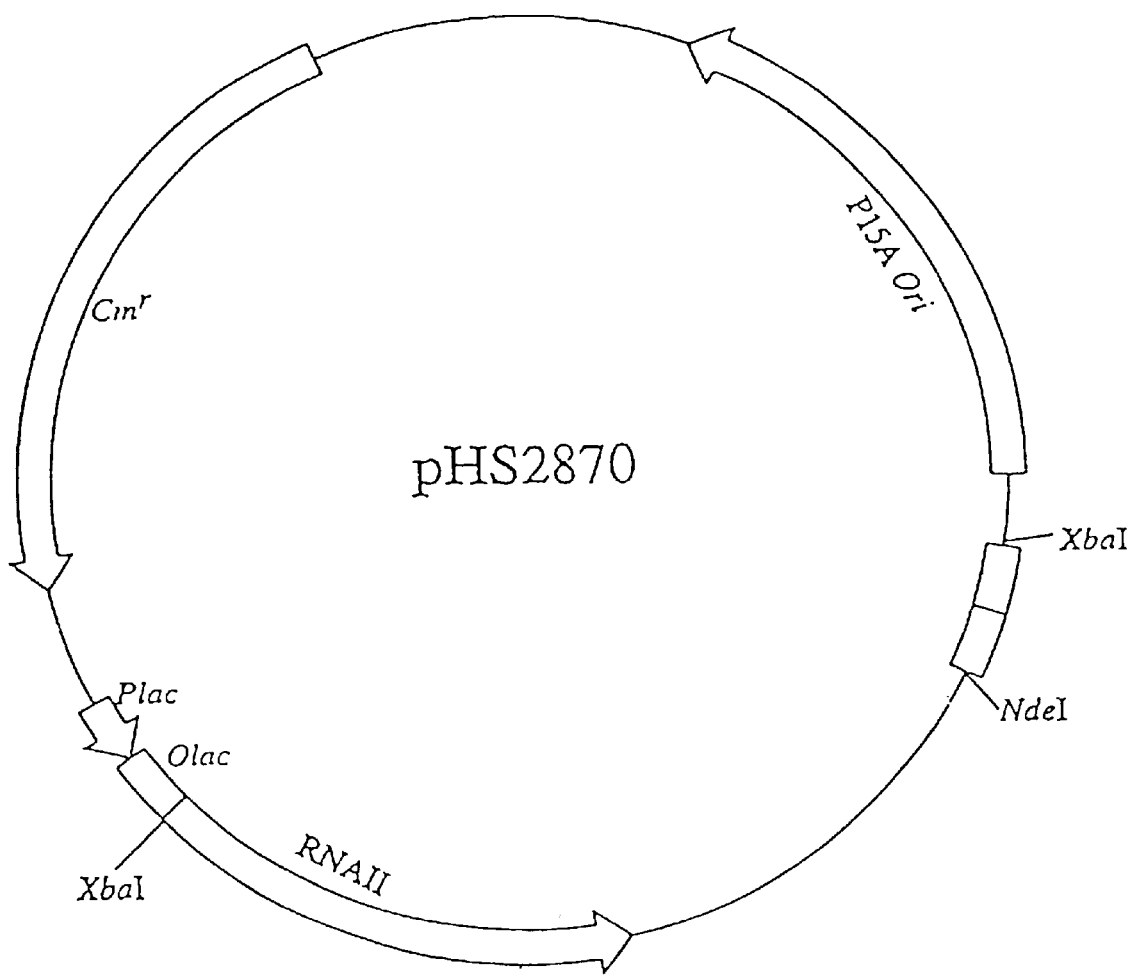
FIG. 4 shows the constitution of the runaway plasmid pHS2870.

Next, the plasmid pHS2870 can be obtained by inserting the RNA1870 fragment obtained by PCR using the RNAIIA primer (base sequence shown by SEQ ID NO:5 in the Sequence Listing) arranged near the RNAII region (replication origin of the plasmid) and the 1870 primer (base sequence shown by SEQ ID NO:6 in the Sequence Listing) arranged at a terminus of the 106 NdeI sequence with the plasmid as a template, into the XbaI site of the plasmid pSTV28 (produced by Takara Shuzo). The plasmid pHS2870 thus constructed is shown in FIG. 4. Generally, the plasmid is present at a copy number of about 30 copies per *Escherichia coli* cell; however, this copy number is increased to several hundreds by the addition of IPTG.

Figure 5:
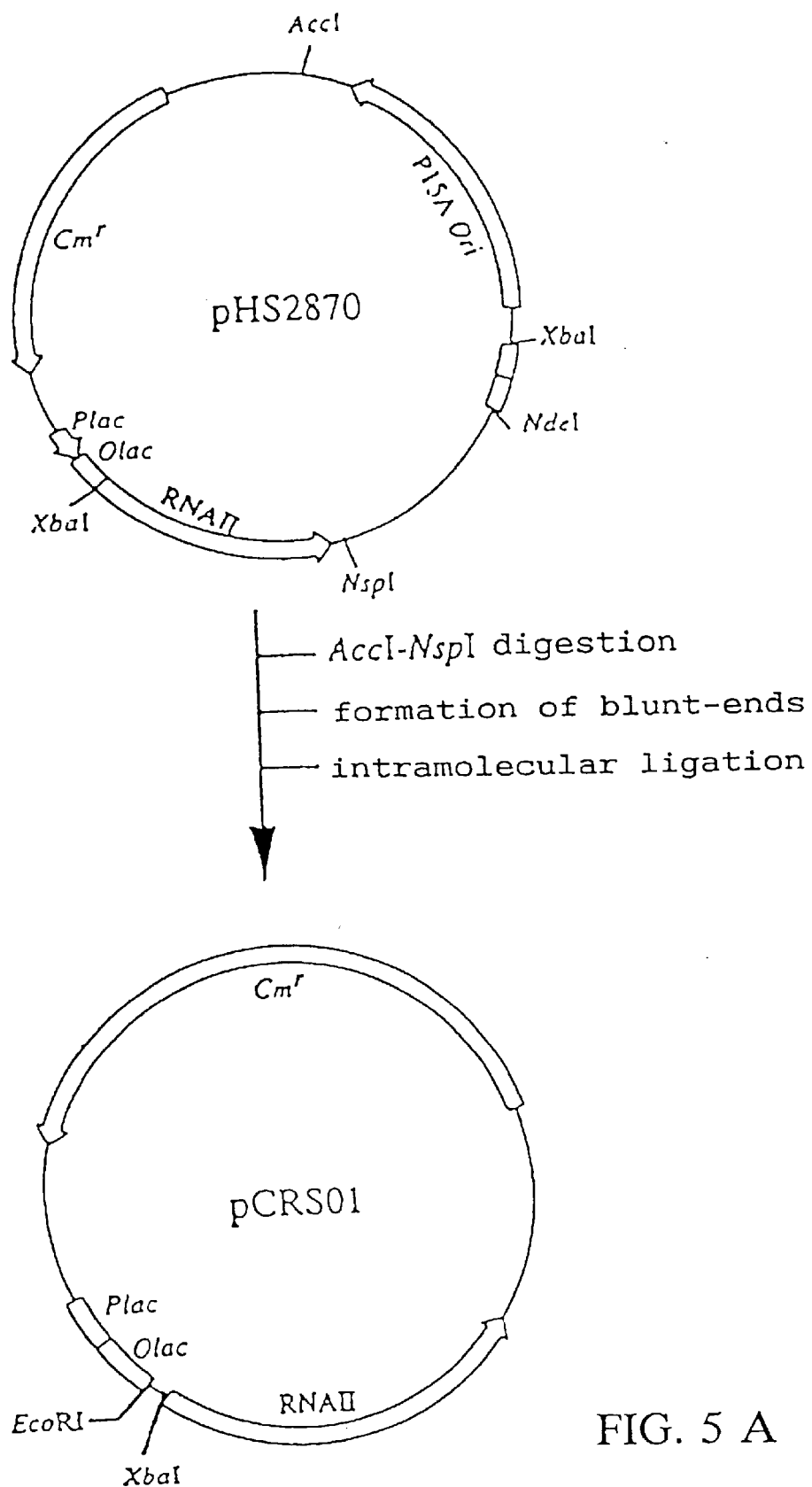
FIGS. 5(A), (B) show the procedure of the construction of the plasmid pCRSO4.
Figure 5:
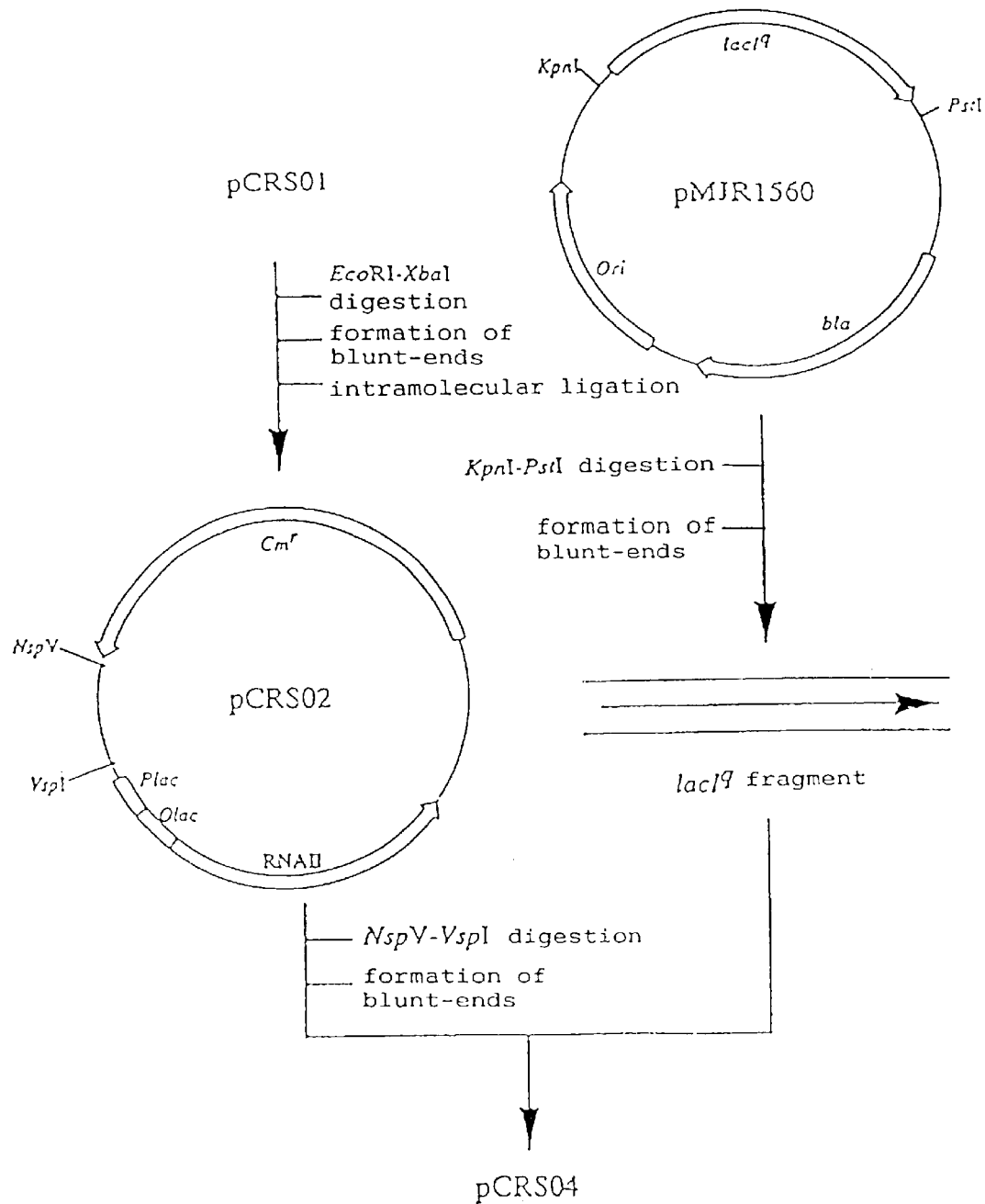
Figure 6:
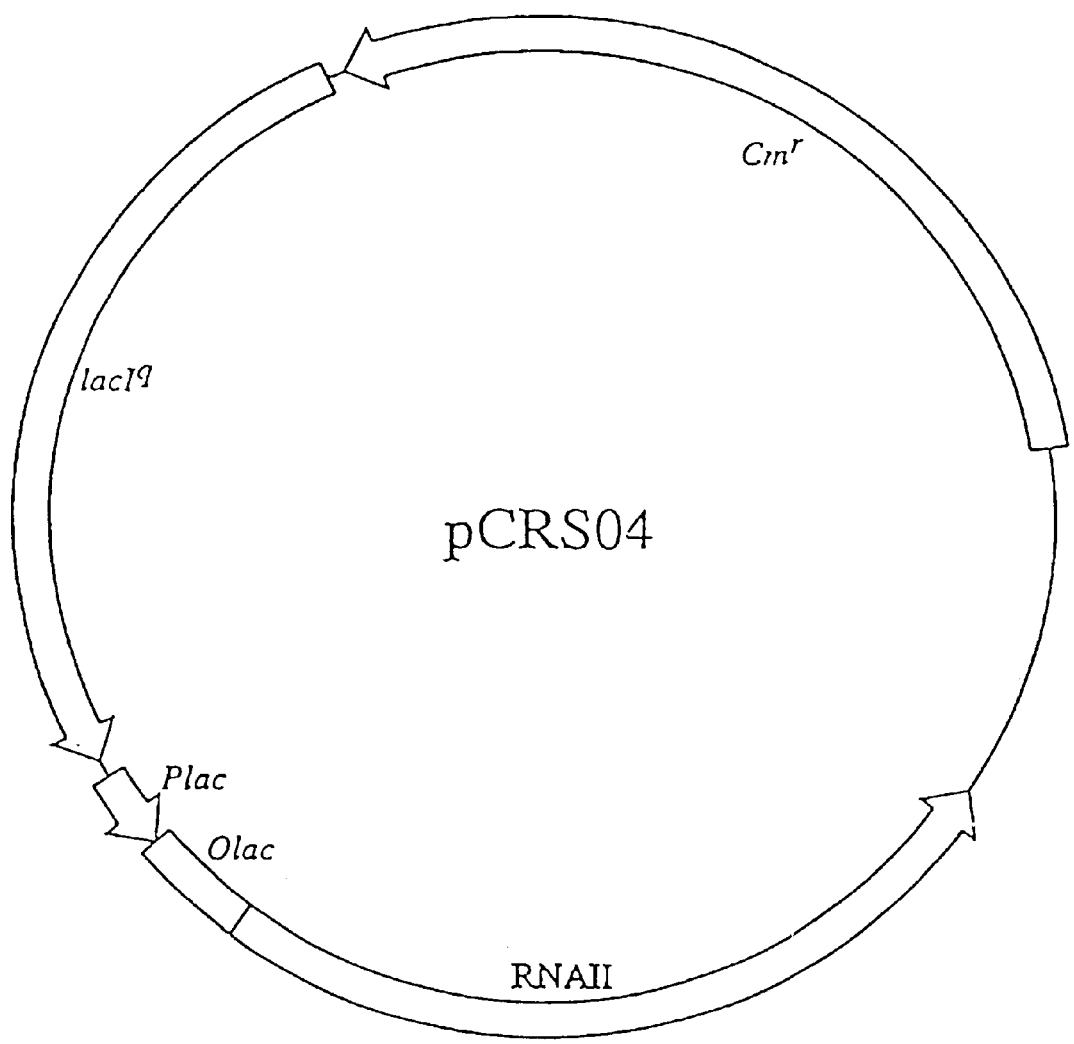
FIG. 6 shows the constitution of the plasmid pCRS04.

The AccI-NspI fragment containing the P15A replication origin derived from the plasmid pSTV28 is then removed from the plasmid (plasmid pCRS01), followed by further removal of the EcoRI-XbaI fragment containing an unnecessary restriction endonuclease site (plasmid pCRS02), after which a DNA fragment containing the lactose repressor (lacIq) gene derived from the plasmid pMJR1560 [Gene, Vol. 51, pp. 225–267 (1987)] is introduced to yield the plasmid pCRS04. A flow diagram of the construction of the plasmid pCRS04 from the plasmid pHS2870 is shown in FIG. 5. The plasmid pCRS04 thus constructed is shown in FIG. 6. The plasmid is a runaway plasmid induced by IPTG; generally, the plasmid is present at a copy number of 1 to 2 copies per *Escherichia coli* cell; however, this copy number is increased to several hundreds by the addition of IPTG.

To control the expression of the desired gene inserted into the plasmid, the $P_{SP6}$-$O_{lac}$ EX linker, a double-stranded oligonucleotide containing the SP6 promoter sequence and lac operator sequence, may be introduced into the NheI site of the plasmid to construct the plasmid pACE601. The $P_{SP6}$-$O_{lac}$ EX linker is prepared from the two DNA strands whose base sequences are shown by SEQ ID NO:7 and SEQ ID NO:8 in the Sequence Listing. The plasmid pACE601 is a runaway plasmid vector having the chloramphenicol resistance gene as a selection marker.

Also, by introducing the BspHI fragment containing the β-lactamase gene derived from the plasmid vector pUC118 (produced by Takara Shuzo) into the NhcI site of the above-described plasmid pCRS04 (plasmid pCRS70), subsequently removing the NcoI-BsaAI fragment containing the chloramphenicol resistance gene, and replacing it with the above-described $P_{SP6}$-$O_{lac}$ EX linker, the plasmids pACE701 and pACE702 can be constructed, which plasmids have the linker inserted in mutually opposite directions. These plasmids are runaway plasmid vectors having the ampicillin resistance gene as a selection marker.

The potential of the thus-obtained plasmids pACE601, pACE701 and pACE702 used for control of the expression of the desired gene can be determined using the β-galactosidase gene as a reporter gene, as described above. It is possible to construct model expression plasmids by introducing a DNA fragment containing the β-galactosidase gene as amplified by PCR using the primers trpA-N-NcoI and lacZ-C-NcoI with the plasmid pMS434 [Gene, Vol. 57, pp. 89–99 (1987)] as a template, into the NcoI site downstream of the SP6 promoter in each of the above-described three plasmids. The base sequences of the primers trpA-N-NcoI and lacZ-C-NcoI are shown by SEQ ID NO:9 and SEQ ID NO:10 in the Sequence Listing, respectively. The plasmids thus obtained are designated pACE601Z, pACE701Z and pACE702Z, respectively. In *Escherichia coli* transformed with these model expression plasmids, absolutely no β-galactosidase activity is detected, demonstrating very exact control of the expression of the β-galactosidase gene.

Using the Nsp7524 III restriction endonuclease gene, it is possible to confirm that a gene whose expression product acts lethally on the host can be isolated and expressed using the plasmid of the present invention. The plasmid pBRN3 contains the Nsp7524 III restriction modification system gene. *Escherichia coli*MC1061 as transformed with the plasmid, designated *Escherichia coli* MC1061/pBRN3, has been deposited under accession number FERM BP-5741 at the National Institute of Bioscience and Human-Technology, Agency of Industrial Science and Technology, Ministry of International Trade and Industry [address: 1–3, Higashi 1 chome, Tsukuba-shi, Ibaraki-ken, 305, Japan] since September 28, 1995 (date of original deposition). By a PCR-based DNA amplification reaction using a pair of the primers L-ORF and NspR-ORF3 with the plasmid pBRN3 prepared from the transformant as a template, a DNA fragment containing the Nsp7524 III restriction endonuclease gene alone can be obtained. The base sequences of the primers L-ORF and NspR-ORF3 are shown by SEQ ID NO:11 and SEQ ID NO:12 in the Sequence Listing, respectively. By introducing into *Escherichia coli* HB101 the plasmid pACE601-NspIII, which is obtained by inserting the resulting DNA fragment into the NcoI site downstream of the SP6 promoter of the above-described plasmid pACE601, the transformant *Escherichia coli* HB101/pACE601-NspIII can be obtained. The transformant allows the host to stably retain the Nsp7524 III restriction endonuclease gene despite the absence of the Nsp7524 III modification enzyme gene.

Furthermore, the transformant *Escherichia coli* HB101/ pFSP6/pACE601-NspIII can be prepared by introducing the above-described system plasmid pFSP6 into the transformant. By culturing the transformant and inducing expression by the addition of IPTG at the appropriate time, the possibility of production of the Nsp7524 III restriction endonuclease in the culture can be confirmed.

The third aspect of the present invention provides a method for isolating a desired gene characterized by using the above-described plasmid vector. The isolation method of the present invention is suitably applied to the isolation of a gene whose expression product is lethal or harmful against the host, especially a restriction endonuclease gene. By using the present method, it is possible to isolate a restriction endonuclease gene that has not been isolated so far, e.g., the AccIII restriction endonuclease gene, even in the absence of the AccIII modification enzyme gene. Isolation of a restriction endonuclease gene can be achieved not only by the "shotgun method", wherein the genomic DNA of a microorganism that produces the desired enzyme is cleaved with the appropriate restriction endonuclease, and the resulting DNA fragment is inserted directly into, for example, the plasmid pACE611, but also by the use of a cassette library of the genomic DNA of a microorganism that produces the restriction endonuclease. By obtaining a gene by DNA amplification with the cassette library as a template, it is possible to express a gene prepared from a microorganism whose transcription mechanism differs from that of the host. The method of isolating a restriction endonuclease gene using a cassette library is hereinafter described with reference to an example involving the AccIII restriction endonuclease.

A cassette library of the genomic DNA of a microorganism that produces the AccIII restriction endonuclease, i.e., an Acc bacterium, can be prepared as follows: Genomic DNA is extracted from the cell culture of an Acc bacterium, and digested with the appropriate restriction endonuclease, after which the resulting DNA fragment is ligated to a cassette having a protruding end complementary to the fragment. Several similar cassette libraries are prepared using different restriction endonucleases for genomic DNA cleavage. These libraries are generically referred to as an Acc genomic cassette library. Next, the desired restriction endonuclease protein is purified from the Acc bacterium, its amino acid sequence is partially determined, and a primer is synthesized on the basis of the sequence. Using this primer and cassette primer, a PCR-based DNA amplification reaction is carried out with each cassette library as a template, to obtain a DNA fragment containing an AccIII restriction endonuclease gene fragment. The base sequence of the DNA fragment obtained is determined by, for example, direct sequencing of the PCR product, to determine the full-length base sequence of the AccIII restriction endonuclease gene.

By designing a primer capable of amplifying the full-length sequence of the AccIII restriction endonuclease gene from the base sequence, and carrying out a PCR-based DNA amplification reaction using this primer with the genomic DNA of the Acc bacterium as a template, a DNA fragment containing the full-length sequence of the AccIII restriction endonuclease gene is obtained. The DNA fragment obtained is inserted downstream of the SP6 promoter of the plasmid pACE611 so that the codon frames are adjusted, and the resulting recombinant plasmid is introduced into, for example, *Escherichia coli* JM109, to yield transformants. Transformants containing the AccIII restriction endonuclease gene in an expressible condition can be selected by culturing each transformant, inducing gene expression by the gene expression method of the present invention, and determining the AccIII restriction endonuclease activity in each culture obtained, as well as by drawing the restriction endonuclease map of the plasmid DNA harbored by each transformant.

Figure 7:
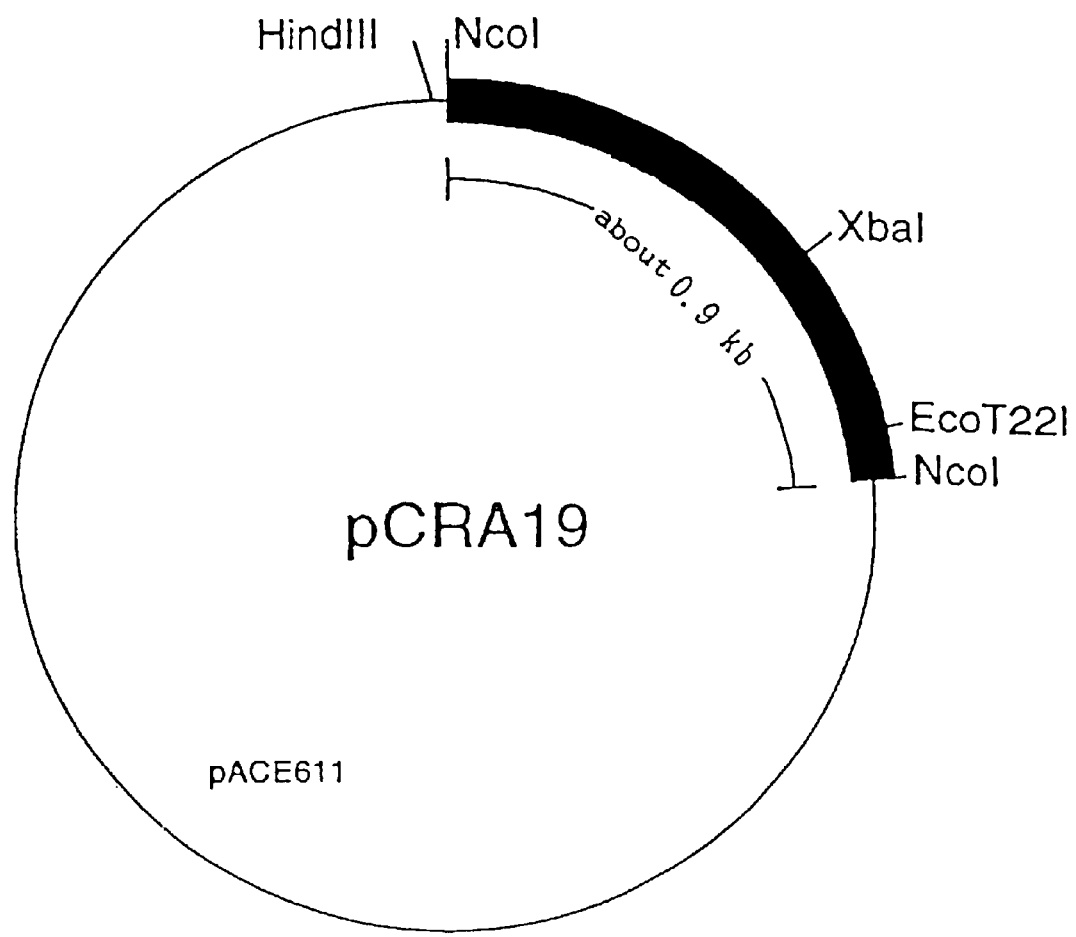
FIG. 7 shows the constitution of the plasmid pCRA19.

The AccIII restriction endonuclease gene thus obtained was actually inserted into the plasmid pACE611, and the resulting plasmid was designated pCRA19. The restriction endonuclease map of this plasmid is shown in FIG. 7, wherein the bold solid line indicates the DNA fragment containing the AccIII restriction endonuclease gene. *Escherichia coli* JM109 as incorporating the plasmid pCRA19, designated *Escherichia coli* JM109/pCRA19, has been deposited under accession number FERM BP-5743 at the National Institute of Bioscience and Human-Technology, Agency of Industrial Science and Technology, Ministry of International Trade and Industry [address: 1–3, Higashi 1 chome, Tsukuba-shi, Ibaraki-ken, 305, Japan] since May 28, 1996 (date of original deposition). The transformant stably retains the restriction endonuclease gene, despite the absence of the AccIII modification enzyme gene therein. By the above-described method, a restriction endonuclease gene can be isolated without the co-presence of a modification enzyme gene that constitutes a restriction modification system gene.

The fourth aspect of the present invention provides a polypeptide possessing an activity of the AccIII restriction endonuclease.

In the present specification, the term "AccIII restriction endonuclease" as a general term of polypeptides possessing an activity of the AccIII restriction endonuclease may be used in some cases. The AccIII restriction endonuclease of the present invention comprises the amino acid sequence described in SEQ ID NO:1 in the Sequence Listing, for example.

The AccIII restriction endonuclease of the present invention also includes, but not limited to the above, the polypeptide containing the entire or a portion of the amino acid sequence described in SEQ ID NO:1 in the Sequence Listing and possessing an activity of the AccIII restriction endonuclease. Furthermore, the polypeptide having an amino acid sequence resulting from at least one of deletion, addition, insertion or substitution of one or more amino acid residues in the amino acid sequence of SEQ ID NO:1 or a portion thereof in the Sequence Listing and possessing an activity of the AccIII restriction endonuclease is included in the scope of the present invention.

Generally, a naturally-occurring protein can undergo deletion, insertion, addition, substitution and other variations of amino acid residues in its amino acid sequence due to modifications, etc. of the protein in vivo or during purification, as well as those due to polymorphism and variation of the gene encoding it. Nevertheless, it is known that there are some such polypeptides which are substantially equivalent to variation-free proteins in terms of physiological and biological activity. Thus, those structurally different from the corresponding protein, but having no significant difference of function or activity from the protein is within the scope of the present invention. It is also the same when artificially introducing the above variations to the amino acid sequence of a protein and in this case, it is possible to produce more diverse variants. For example, the methionine residue at the N-terminus of a protein expressed in *Escherichia coli* is reportedly often removed by the action of methionine aminopeptidase, but the removal is not completely done depending on the kinds of proteins, and some such expressed proteins have the methionine residue and others not. However, the presence or absence of the methionine residue does not affect protein activity in most cases. It is also known that a polypeptide resulting from replacement of a particular cysteine residue with serine in the amino acid sequence of human interleukin 2 (IL-2) retains IL-2 activity [Science, 224, 1431 (1984)].

In addition, in producing a protein by gene engineering, the desired protein is often expressed as a fused protein. For example, the N-terminal peptide chain derived from another protein is added to the N-terminus of the desired protein to enhance the expression of the desired protein, or purification of the desired protein is facilitated by adding an appropriate peptide chain to the N- or C-terminus of the desired protein, expressing the protein, and using a carrier showing affinity for the peptide chain added. Thus, even if the polypeptide has an amino acid sequence partially different from the AccIII restriction endonuclease of the present invention, it is within the scope of the present invention as long as it possesses essentially equivalent activity to the AccIII restriction endonuclease of the present invention.

The AccIII restriction endonuclease can be obtained by, for example, culturing the above-described transformant *Escherichia coli* JM109/pCRA19, which contains the AccIII restriction endonuclease gene, adding the inducing agent IPTG at an appropriate time during its cultivation to increase the copy number of pCRA19, and subsequently infecting with the phage M13sp6.

The AccIII restriction endonuclease can be harvested from the transformant culture by, for example, collecting cells from the culture, subsequently extracting the enzyme by ultrasonic disruption, ultracentrifugation, etc., and then purifying the enzyme by a combination of nucleic acid removal, salting-out, affinity chromatography, gel filtration, ion exchange chromatography, etc. Because the above-described culture, which serves as the starting material for this purification, does not contain other restriction endonucleases, such as AccI and AccII, an enzyme preparation of desired purity can be obtained more easily than by conventional purification methods.

The fifth aspect of the present invention provides a DNA encoding a polypeptide possessing an activity of the AccIII restriction endonuclease.

The DNA of the present invention encoding a polypeptide possessing an activity of the AccIII restriction endonuclease comprises a DNA encoding the amino acid sequence described in SEQ ID NO:1 in the Sequence Listing, and includes but not limited to, a DNA comprising the base sequence described in SEQ ID NO:2 in the Sequence Listing, for example. Specifically, the following DNAs are within the scope of the present invention.

(1) a DNA encoding a polypeptide which contains the entire or a portion of the amino acid sequence described in SEQ ID NO:1 in the Sequence Listing and possesses an activity of the AccIII restriction endonuclease;
(2) a DNA containing the entire or a portion of the DNA shown in SEQ ID NO:2 in the Sequence Listing, wherein the expression product of the DNA possesses an activity of the AccIII restriction endonuclease;
(3) a DNA encoding a polypeptide resulting from at least one of deletion, addition, insertion or substitution of one or more amino acid residues in the amino acid sequence of SEQ ID NO:1 in the Sequence Listing or a portion thereof and possessing an activity of the AccIII restriction endonuclease; and
(4) a DNA capable of hybridizing to the DNA described in above (1) to (3), and encoding a polypeptide possessing an, activity of the AccIII restriction endonuclease, etc.

In addition, if the hybridization is carried out under the stringent condition using the above obtained DNA as a probe, a similar DNA somewhat different from the obtained DNA (SEQ ID NO:2 in the Sequence Listing) but encoding a polypeptide possessing the same enzyme activity, can be obtained. Such a DNA is also included in the scope of the present invention.

Such a stringent condition refers to that the membrane with DNA immobilized thereon is subjected to hybridization with the probe in a solution containing 6×SSC (1×SSC is a solution of 8.76 g of NaCl and 4.41 g of sodium citrate in 1 liter of water), 1% SDS, 100 µg/ml salmon sperm DNA, 0.1% bovine serum albumin, 0.1% polyvinylpyrrolidone and 0.1% Ficoll, incubating at 65° C. for 20 hours, for example.

Methods for obtaining similar DNA encoding the AccIII restriction endonuclease by hybridization include, for example, the following method.

First, DNA obtained from an appropriate gene source is ligated to a plasmid or a phage vector by a conventional method to yield a DNA library. This library is introduced into an appropriate host; the resulting transformants are cultured on plates; colonies or plaques that have grown are transferred onto nitrocellulose or nylon membranes and denatured, after which the DNA is fixed onto the membrane. These membranes are incubated for hybridization in a solution of the above-described composition containing a probe previously labeled with $^{32}$p etc. (probe used may be any polynucleotide encoding the entire or a portion of the amino acid sequence shown by SEQ ID NO:1 in the Sequence Listing, exemplified by a polynucleotide consisting of, or containing, the entire or a portion of the base sequence shown by SEQ ID NO:2 in the Sequence Listing) under the conditions shown above. After completion of the hybridization, the non-specifically adsorbed probe is washed out, followed by autoradiography etc., to identify clones that have hybridized to the probe. This procedure is repeated until the desired hybridizing clone is isolated. The clone thus obtained retains DNA encoding a polypeptide having the desired enzyme activity.

The DNA obtained is determined for base sequence to confirm that it encodes the desired enzyme protein, by, for example, the method described below.

For base sequencing, the transformant is cultured in a test tube etc. when the host is *Escherichia coli*, and a plasmid is prepared by a conventional method, provided that the transformant has been prepared using a plasmid vector. Using the plasmid obtained as a template as is, or after the insert is taken out and subcloned into the M13 phage vector etc., the base sequence is determined by the dideoxy method. In the case of a transformant prepared using a phage vector as well, the base sequence can be determined by basically the same procedures.

These basic experimental processes from cultivation to base sequencing are described in, for example, Molecular Cloning: A Laboratory Manual, 1982, T. Maniatis et al., published by Cold Spring Harbor Laboratory.

Whether or not the DNA obtained is similar DNA encoding the desired AccIII restriction endonuclease can be confirmed by comparing the determined base sequence with the base sequence shown by SEQ ID NO:2 in the Sequence Listing, or by comparing the amino acid sequence deduced from the determined base sequence with the amino acid sequence shown by SEQ ID NO:1 in the Sequence Listing.

When the DNA obtained does not contain the entire portion of the region encoding the desired restriction endonuclease, the entire encoding region can be obtained by synthesizing a primer on the basis of the base sequence of the DNA obtained, and amplifying the lacking region by PCR using the primer, or repeating screening the DNA library using the DNA fragment obtained as a probe.

It is possible to prepare a transformant containing the thus-obtained similar DNA encoding the AccIII restriction endonuclease, to allow the transformant to express the enzyme protein encoded by the DNA, and to purify the enzyme protein expressed. Preparation of the transformant and expression and purification of the enzyme protein can be all achieved using the plasmid of the present invention. The enzyme protein thus obtained retains AccIII restriction endonuclease activity.

Additionally, the AccIII modification enzyme and DNA encoding the enzyme, both of which have not been obtained so far, can also be obtained using the above-described DNA encoding the AccIII restriction endonuclease.

For example, on the basis of the mutually close location of a restriction endonuclease gene and a modification enzyme gene in many cases, this purpose can be accomplished by obtaining a gene region encoding a protein near the restriction endonuclease gene by a DNA amplification reaction with a cassette library as a template, inserting it into an appropriate expression vector to allow the gene to be expressed, and confirming AccIII modification enzyme activity by an appropriate method. AccIII modification enzyme activity can also be confirmed, for example, on the basis of the resistance of the DNA prepared from the transformant to the cleavage activity of the AccIII restriction endonuclease. Provided that the base sequence of the above-described gene region is determined to confirm homology to a conserved region between modification enzyme genes of a known restriction modification system [Journal of Molecular Biology, Vol. 206, pp. 305–321 (1989)], it can be anticipated to some extent before gene expression that the gene is a modification enzyme gene.

By using a cassette library of the genomic DNA of the Acc bacterium as described above, the AccIII modification enzyme and DNA encoding it can be obtained. Its amino acid sequence and base sequence are shown by SEQ ID NO:13 and SEQ ID NO:14 in the Sequence Listing, respectively.

AccIII modification enzyme herein is not limited to the above described. As stated in the description of AccIII restriction endonuclease, it is a polypeptide containing the entire or a portion of the amino acid sequence described in SEQ ID No:13 in the Sequence Listing and possessing the AccIII modification enzyme activity. Furthermore, the polypeptide resulting from at least one of deletion, addition, insertion or substitution of one or more amino acid residues in the amino acid sequence of SEQ ID NO:13 or a portion thereof in the Sequence Listing and possessing the AccIII modification enzyme activity is also included in the scope of the present invention.

A DNA encoding AccIII modification enzyme in the present invention herein comprises a DNA encoding the amino acid sequence described in the SEQ ID NO:13 in the Sequence Listing, and includes, but not limited to, a DNA comprising the base sequence described in the SEQ ID NO:14 in the Sequence Listing, for example. Specifically, the following DNAs are within the scope of the present invention.

(1) a DNA encoding a polypeptide containing the entire or a portion of the amino acid sequence described in SEQ ID NO:13 in the Sequence Listing and possessing the AccIII modification enzyme activity;
(2) a DNA containing the entire or a portion of the DNA shown in SEQ,ID NO:14 in the Sequence Listing, wherein the expression product of the DNA possesses the AccIII modification enzyme activity;
(3) a DNA encoding a polypeptide resulting from at least one of deletion, addition, insertion or substitution of one or more amino acid residues in the amino acid sequence of SEQ ID NO:13 or a portion thereof in the Sequence Listing and possessing the AccIII modification enzyme activity; and
(4) a DNA capable of hybridizing to the DNA described in above (1) to (3), and encoding a polypeptide possessing the AccIII modification enzyme activity, etc.

The present invention is hereinafter described in more detail by means of the following reference example and working examples, which examples are not to be construed as limitative. Of the procedures described herein, basic ones regarding plasmid preparation, restriction endonuclease digestion, etc. were achieved in accordance with the methods described in Molecular Cloning: A Laboratory Manual, 2nd edition, edited by T. Maniatis et al., published by Cold Spring Harbor Laboratory, 1989.

Reference Example (1) Culture medium and conditions

*Escherichia coli* was aerobically cultured at 37° C. using LB medium (1% trypton, 0.5% yeast extract, 0.5% NaCl, pH 7.0). Antibiotics were each added to the medium at various concentrations depending on the plasmid retained by the *Escherichia coli* as follows: 25 μg/ml kanamycin for pFSP6, 20 μg/ml ampicillin for pXX325, 50 μg/ml ampicillin for ampicillin-resistant ColE1 type plasmid, and 100 μg/ml ampicillin for ampicillin-resistant pUC type plasmid. In the expression induction experiment, the culture broth obtained after cultivation until the stationary phase was inoculated to a fresh medium at 1%, then aerobically cultured at 37° C., after which isopropyl-β-D-thiogalactoside (IPTG) was added to a final concentration of 0.2 mM upon reach of an $OD_{600}$ value of 0.6 ($6\times10^8$ cells/ml), followed by further cultivation.

(2) Construction of the system plasmid pFSP6

Figure 8:
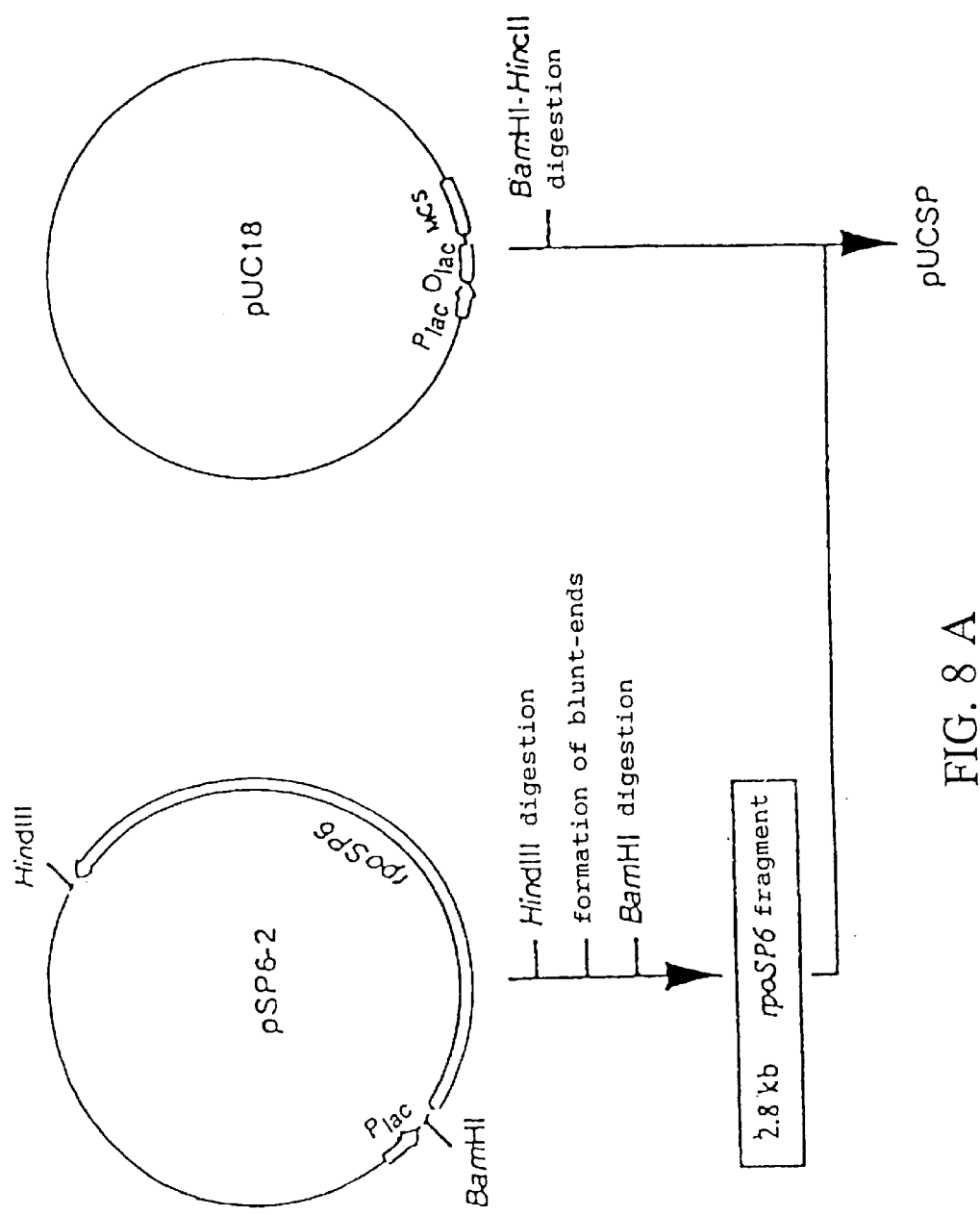
FIGS. 8(A), (B), (C), (D), (E) show the procedure of the construction of the system plasmid pFSP6.
Figure 8:
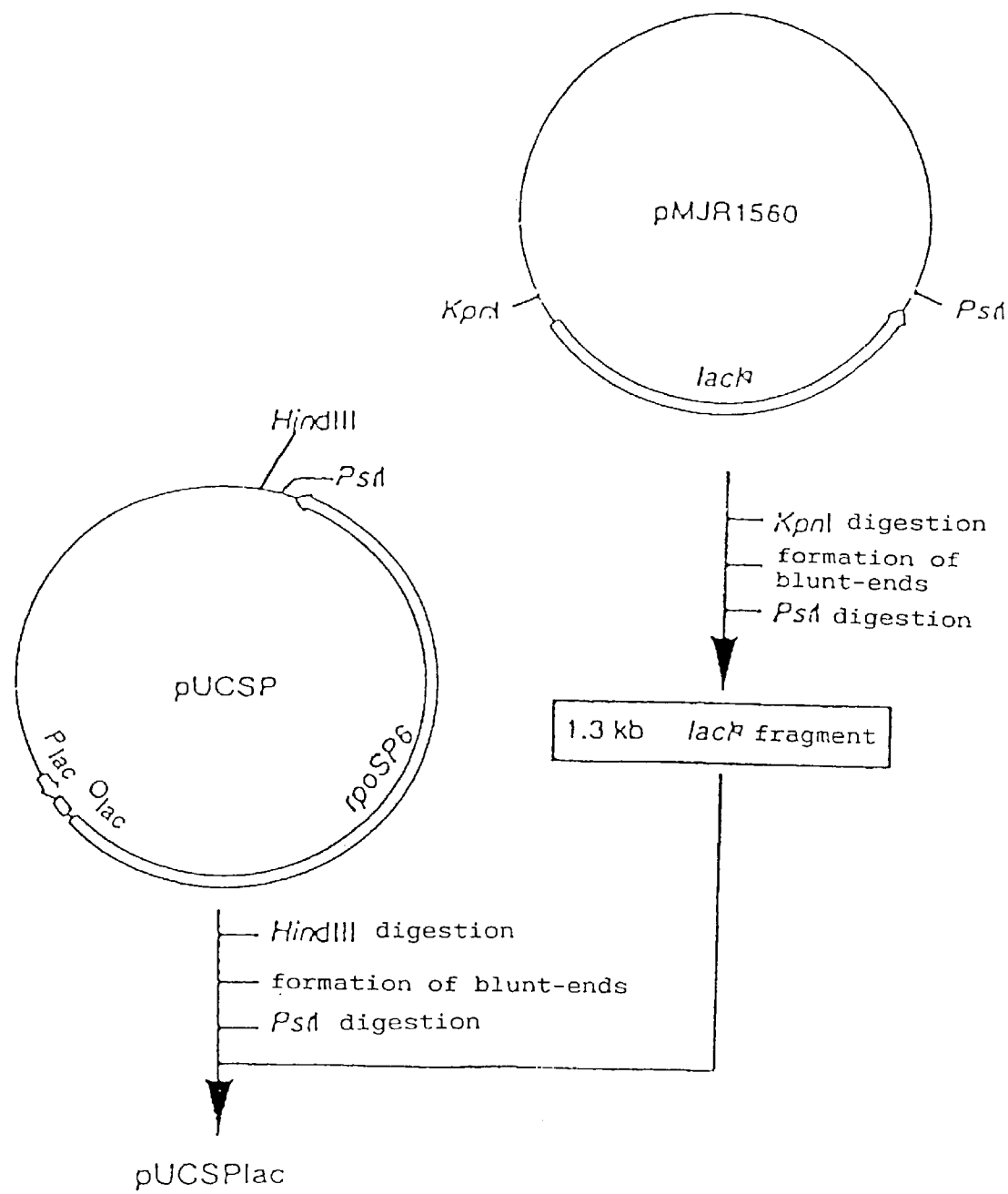
Figure 8:
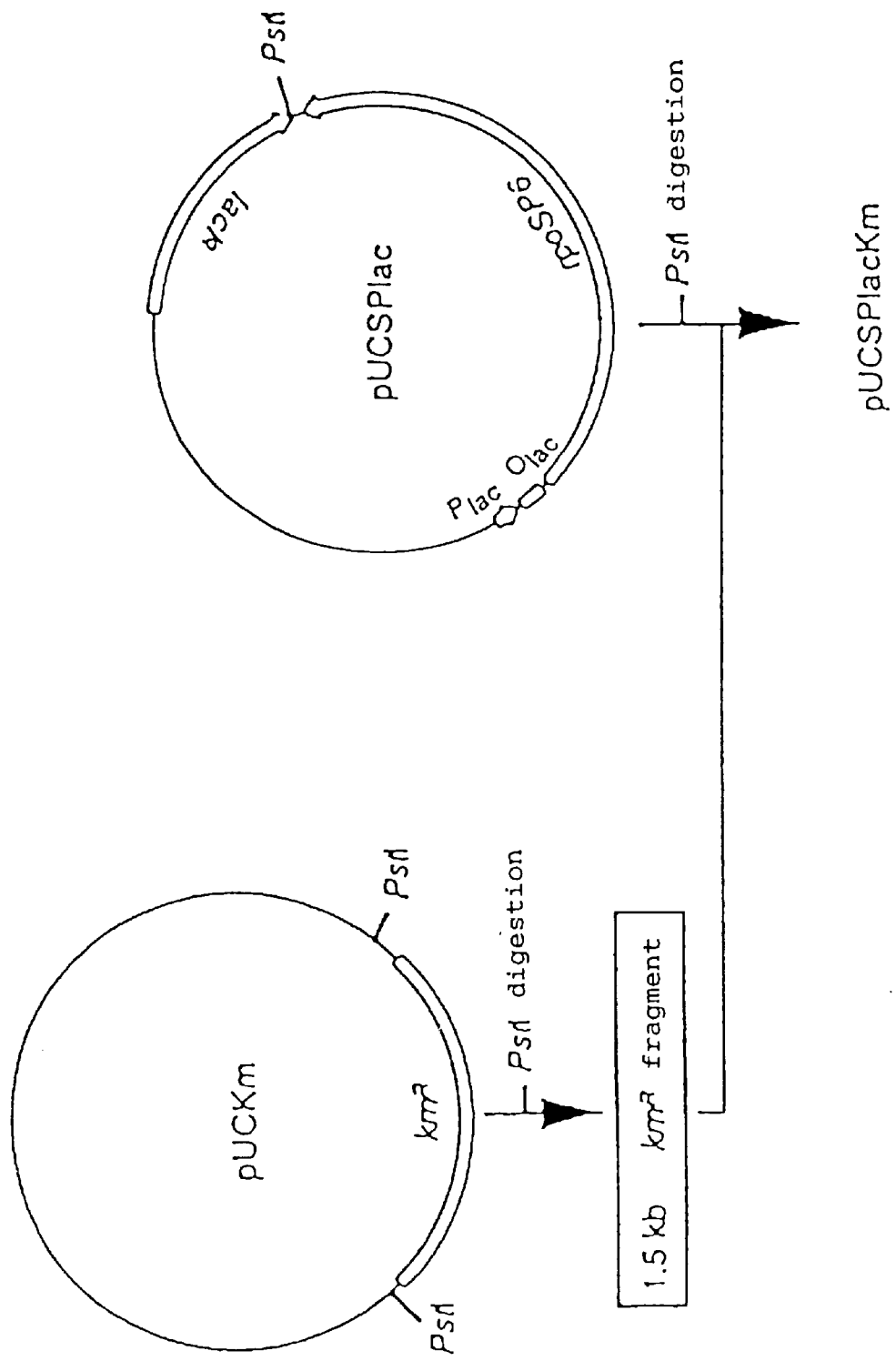
Figure 8:
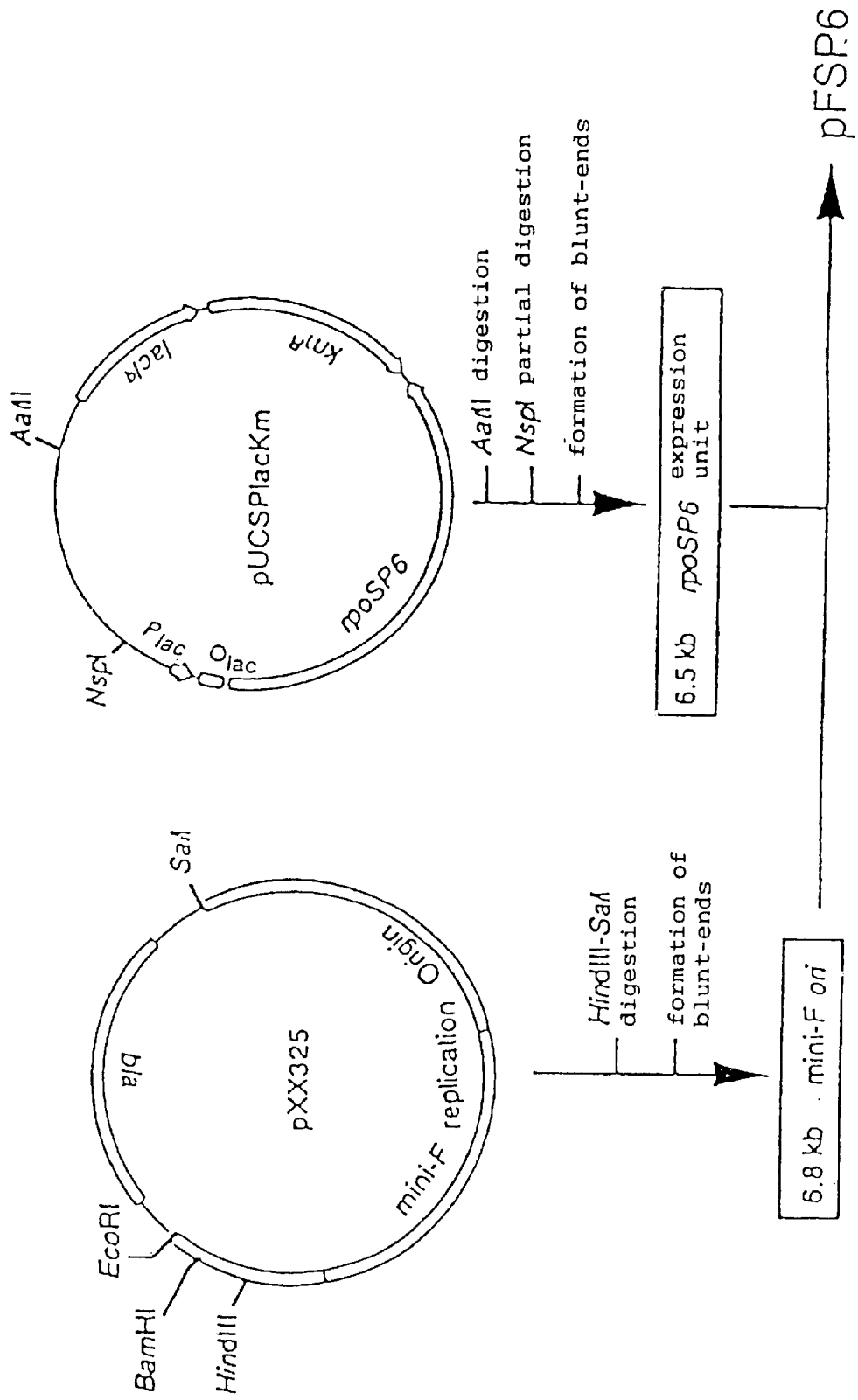
Figure 8:
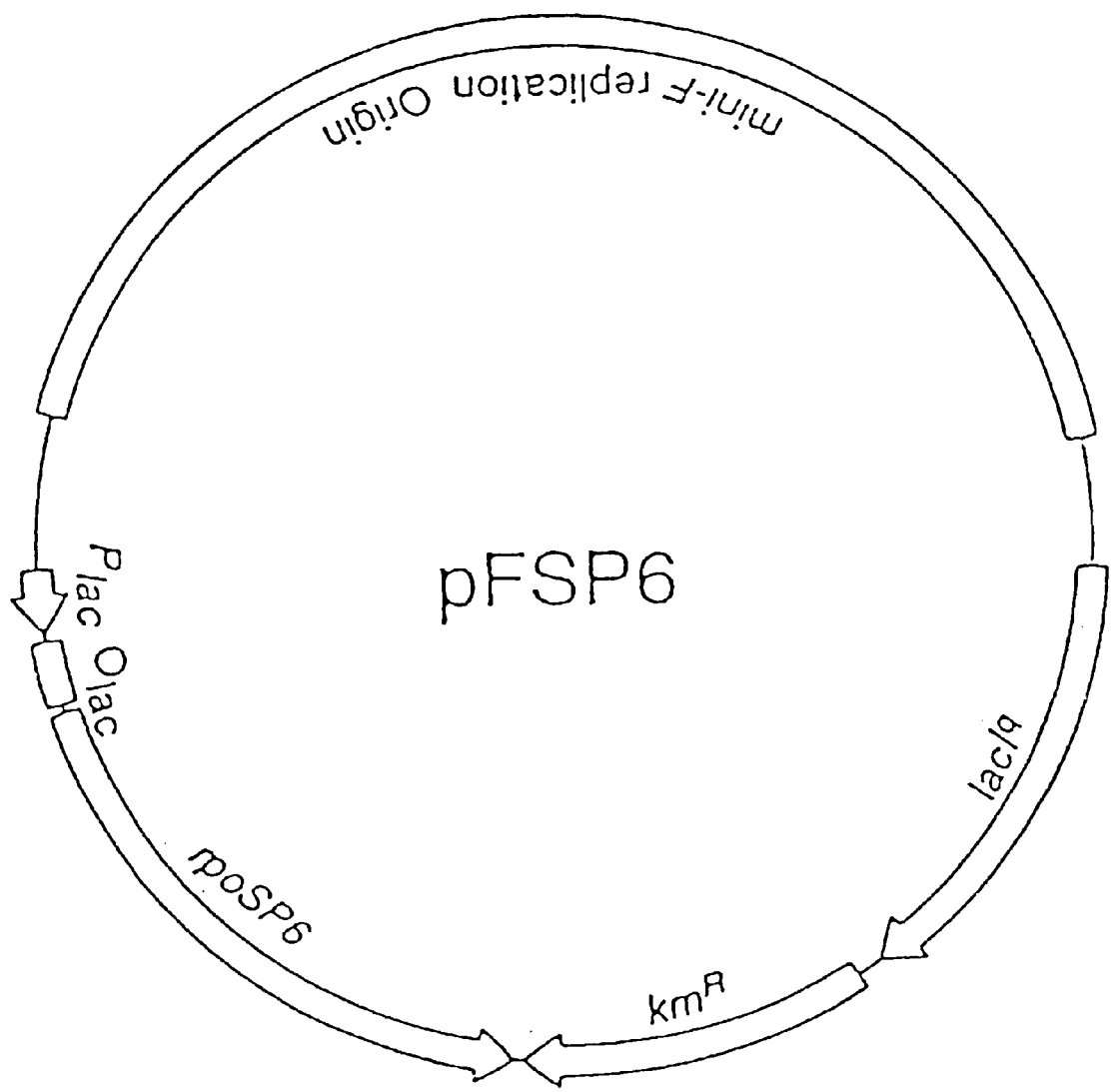

The system plasmid pFSP6 was constructed with *Escherichia coli* JM109 as a host, according to the procedure directed in FIG. 8. The plasmid pSP6-2 [Nucleic Acids Research, Vol. 15, pp. 2653–2664 (1987)] was digested with HindIII (produced by Takara Shuzo) and blunted at both ends, after which it was further digested with BamHI (produced by Takara Shuzo) to yield an about 2.8 kb DNA fragment containing the SP6 RNA polymerase gene, which fragment was mixed with the plasmid vector pUC18 (produced by Takara Shuzo), previously digested with BamHI and HincII (produced by Takara Shuzo), for ligation to construct the plasmid pUCSP. Next, the plasmid pMJR1560 [Gene, Vol. 51, pp. 225–267 (1987)] was digested with KpnI and blunted at both ends, after which it was further digested with PstI (produced by Takara Shuzo) to yield an about 1.3 kb DNA fragment containing the lacIq gene, which was then isolated. The above plasmid pUCSP was digested with HindIII and blunted at both ends, after which it was further digested with PstI to yield a DNA fragment, which was mixed with the above-described about 1.3 kb DNA fragment for ligation to construct the plasmid pUCSPlac.

Furthermore, an about 1.5 kb DNA fragment obtained by PstI digestion of pUCKm [Journal of Molecular Biology, Vol. 147, pp. 217–226 (1981)], which contains the kanamycin resistance gene, was introduced into the PstI site of the above-described plasmid pUCSPlac to construct the plasmid pUCSPlacKm. The plasmid was digested with AatII (produced by Toyobo), after which it was partially digested with NspI (produced by Takara Shuzo) to isolate an about 6.5 kb DNA fragment, which was then blunted at both ends.

On the other hand, the plasmid pXX325 [Proceedings of the National Academy of Sciences of the USA, Vol. 80, pp. 4784–47.88 (1983)] was digested with HindIII and blunted at both ends, after which it was further digested with SalI to isolate an about 6.8 kb DNA fragment containing the replication origin of the miniF plasmid, which fragment was then mixed with the above-described about 6.5 kb DNA fragment for ligation to construct the plasmid pFSP6. *Escherichia coli* HB101 was transformed with the plasmid to form *Escherichia coli* HB101/pFSP6.

(3) Construction of multicopy model expression plasmids

The $P_{SP6}$ linker, a double-stranded oligonucleotide containing the minimum region of the SP6 promoter, was prepared from the two DNA strands whose base sequences are shown by SEQ ID NO:15 and SEQ ID NO:16 in the Sequence Listing, respectively, and was mixed with the plasmid pMS434 [Gene, Vol. 57, pp. 89–99 (1987)], previously digested with XhoI (produced by Takara Shuzo) and HindIII, for ligation to construct the model expression plasmid pMSP6L inserted the above-described promoter sequence upstream of the β-galactosidase gene on the plasmid (FIG. 1).

Figure 2:
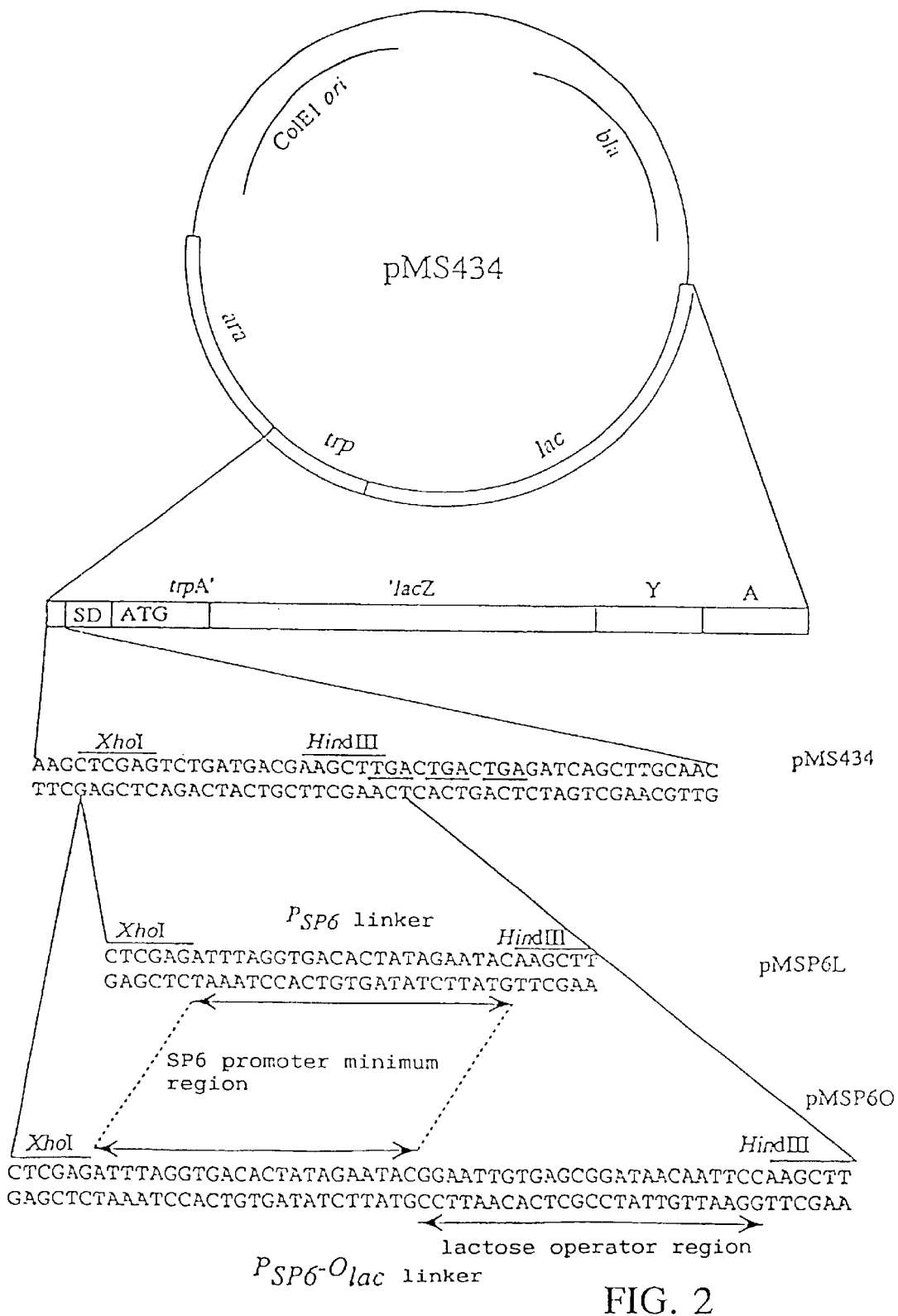
FIG. 2 shows the constitution of the model expression plasmid pMSP60. MS434 contains in part DNA having the DNA sequence identified as SEQ ID NO:31. pMS6L contains in part DNA having the DNA sequence identified as SEQ ID NO:32. pMS60 contains in part DNA having the DNA sequence identified as SEQ ID NO:33.

On the other hand, by inserting a DNA fragment containing the inherent SP6 promoter sequence, obtained by digesting pSP64 [Nucleic Acids Research, Vol. 12, pp. 7035–7056 (1984)] with AccII and HindIII, into the XhoI-HindIII site of the above-described plasmid pMS434, the model expression plasmid pMSP6F was constructed (FIG. 1). Furthermore, the $P_{SP6}$-$O_{lac}$ linker, which contains the minimum region of the SP6 promoter and the lac operator region, was prepared from the two DNA strands whose base sequences are shown by SEQ ID NO:17 and SEQ ID NO:18 in the Sequence Listing, respectively, and was inserted between the XhoI-HindIII site of the above-described plasmid pMS434 to construct the model expression plasmid pMSP60 (FIG. 2).

(4) Promoter activity of the SP6 promoter for *Escherichia coli* RNA polymerase

The plasmids pMSP6L and pMSP6F constructed in Reference Example (3) and the plasmid pMS434 as a control, which does not contain the SP6 promoter sequence, were each introduced into the *Escherichia coli* shown in Table 1. The resulting transformants were each cultured by the method described in Reference Example (1), after which each cell culture broth was harvested during the logarithmic growth phase. The $OD_{600}$ value of each culture broth collected was determined with a portion thereof, while the remaining portion was transferred to a pre-cooled test tube and supplemented with chloramphenicol to a final concentration of 100 mg/ml. With this culture broth as a sample, β-galactosidase activity was determined by the method described in Experiments in Molecular Genetics, edited by J. H. Miller, published by Cold Spring Harbor Laboratory, 1972.

As shown in Table 2, Escherichia coli MC4100 incorporating the model expression plasmid pMSP6L or pMSP6F, both harboring a sequence containing the SP6 promoter, exhibited similar level of low β-galactosidase activity, irrespective of the promoter sequence inserted. However, that incorporating the plasmid pMS434, which does not contain the SP6 promoter, exhibited only lower enzyme activity. In addition, comparing Escherichia coli MRi7 and MRi80 as the hosts revealed decreased β-galactosidase activity in MRi80, wherein the copy number of the plasmid was also decreased.

(5) Evaluation of the system plasmid pFSP6

Each transformant prepared in Reference Example (4) into which the system plasmid pFSP6 was further introduced, was cultured by the method described in Reference Example (1); β-galactosidase activity was determined both in a non-inductive condition and in an inductive condition before and after IPTG addition. The results were shown in Table 3. All transformants exhibited β-galactosidase activity in a non-inductive condition at a level similar to that obtained in the absence of the plasmid pFSP6 shown in Table 2.

On the other hand, with induction by IPTG addition, the β-galactosidase activity in the transformants incorporating the plasmids pMSP6L and pMSP6F was 18 to 32 times compared with that obtained in a non-inductive condition, while there was no increase in the activity in the transformants incorporating the plasmid pMS434.

(6) Effect of the lac operator sequence on expression control

Transformants obtained by introducing the plasmids pMSP6L, pMSP6F, pMSP60 and pMS434, respectively, into Escherichia coli MC4100 incorporating the plasmid pFSP6 were each cultured by the method described in Reference Example (1), and β-galactosidase activity in a non-inductive condition was determined. The results are shown in Table 4. The transformant incorporating the plasmid pMSP60, which contains the lac operator sequence, still showed some β-galactosidase activity, although the activity level was lower than those obtained with the plasmids pMSP6L and pMSP6F. In short, expression in a non-inductive condition could not be completely suppressed simply by introduction of the lac operator sequence.

TABLE 4

| Strain | β- Galactosidase Activity (Non-Inductive Condition) | | | |
| --- | --- | --- | --- | --- |
|  | pMSP6F | pMSP6L | pMSP60 | pMS434 |
| MC4100(pFSP6) | 221 | 234 | 30 | 25 |

Example 1

(1) Culture medium and conditions

Escherichia coli was aerobically cultured at 37° C. using LB medium (1% trypton, 0.5% yeast extract, 0.5% NaCl, pH 7.0). Antibiotics were each added to the medium at various concentrations depending on the plasmid retained by the Escherichia coli as follows: 25 μg/ml kanamycin for pFSP6, 50 μg/ml ampicillin for ampicillin-resistant ColE1 type plasmid, 100 μg/ml ampicillin for ampicillin-resistant pUC type plasmid, 30 μg/ml chloramphenicol for chloramphenicol-resistant runaway plasmid and 30 μg/ml ampicillin for ampicillin-resistant runaway plasmid. In the expression induction experiment, the culture broth obtained after cultivation until the stationary phase was inoculated to a fresh medium at 1%, then aerobically cultured at 37° C., after which isopropyl-β-D-thiogalactoside (IPTG) was added to a final concentration of 0.2 mM upon reach of an $OD_{600}$ value of 0.6 ($6\times10^8$ cells/ml), followed by further cultivation.

(2) Construction of the runaway plasmid pHS2870

Figure 3:
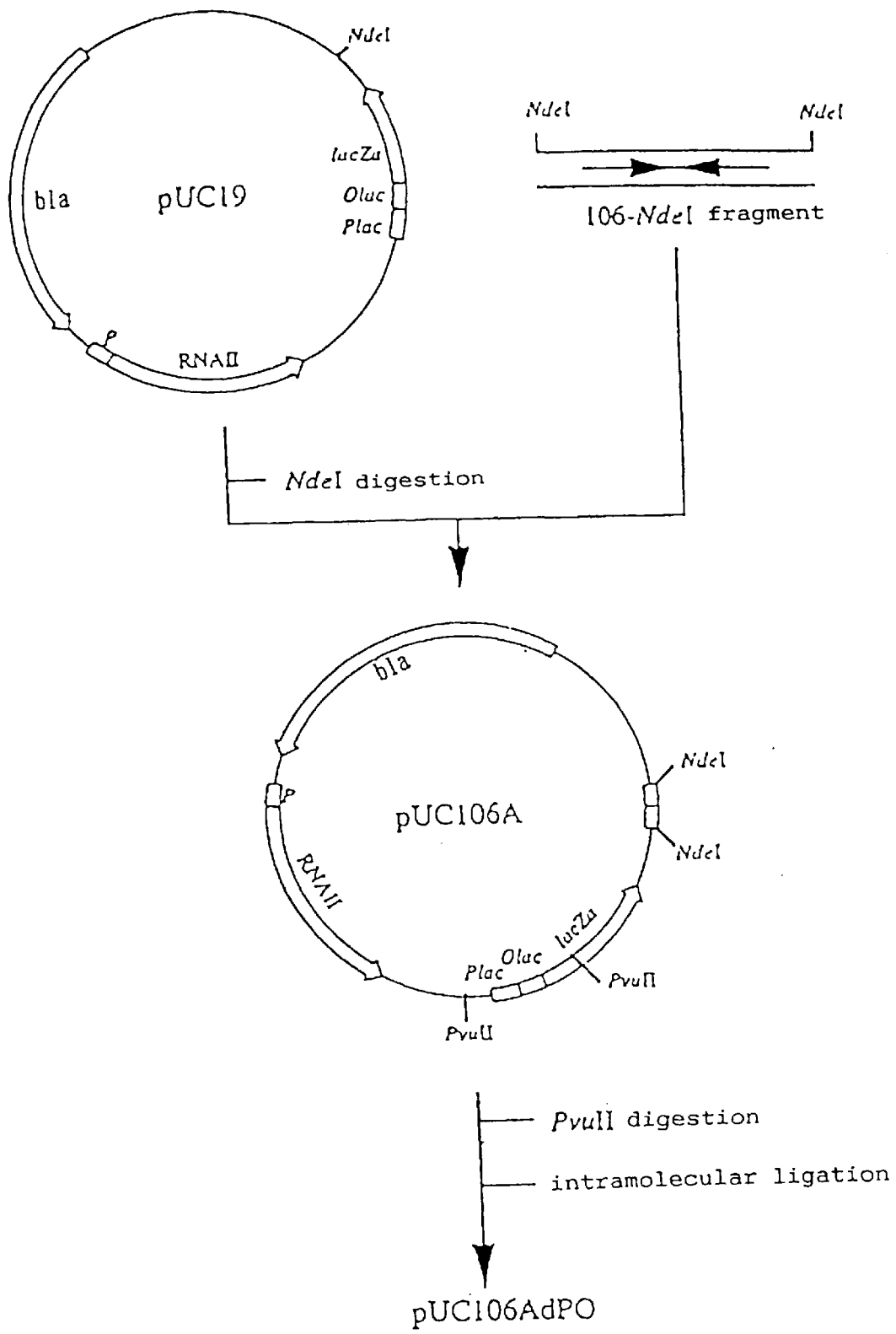
FIGS. 3(A), (B) show the procedure of the construction of the runaway plasmid pHS2870.
Figure 3:
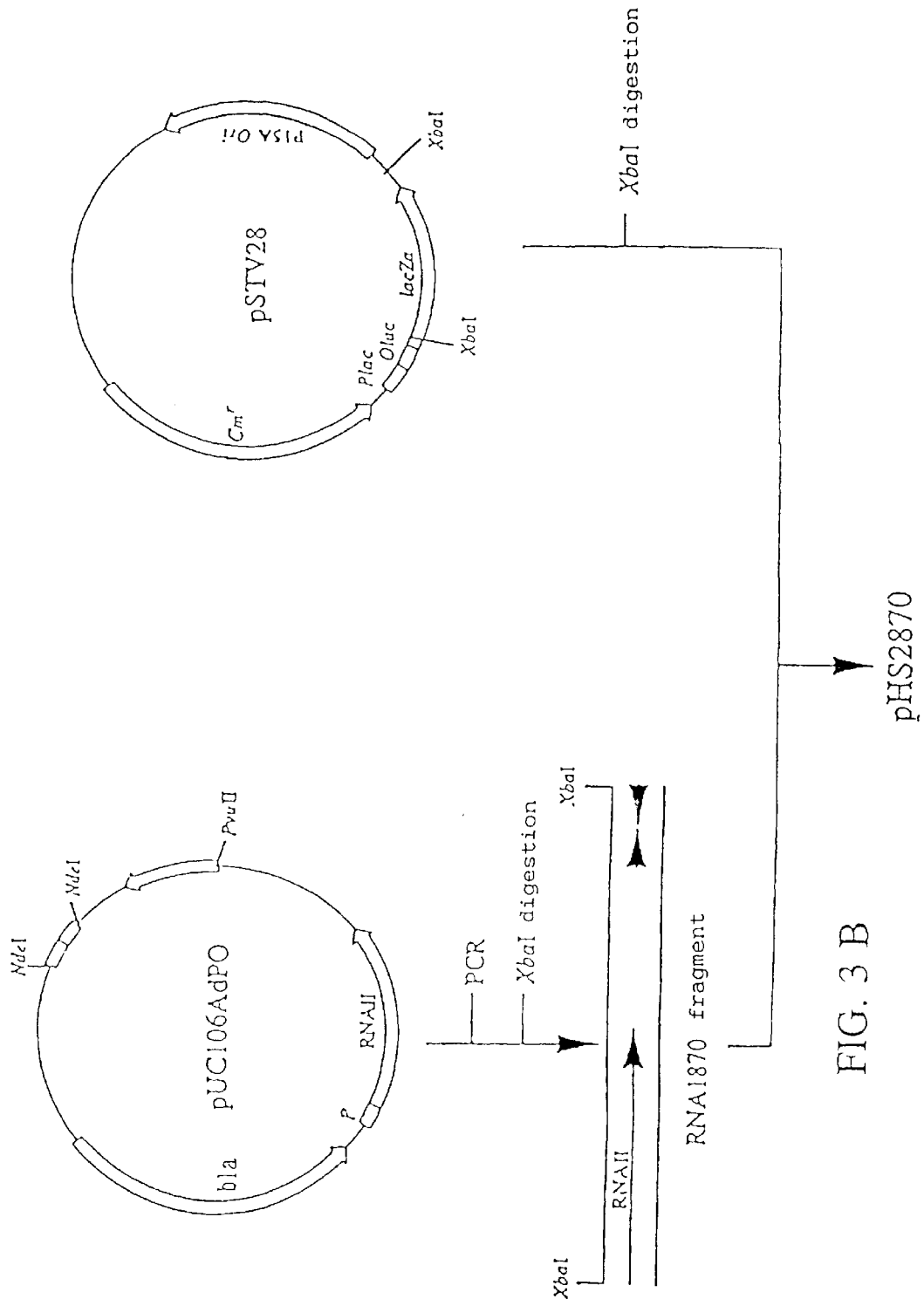

The runaway plasmid pHS2870, which provided a basis for construction of the expression plasmid, was constructed by the procedures shown in FIG. 3. The 106 NdeI DNA fragment prepared from the two DNA strands whose base sequences are shown by SEQ ID NO:3 and SEQ ID NO:4 in the Sequence Listing, respectively, was mixed with the plasmid vector pUC19, previously digested with NdeI, for ligation. The plasmid pUC106A thus obtained was digested with PvuII and subjected to self-ligation to yield the yield the plasmid pUC106AdPO. With this plasmid pUC106AdPO as a template, PCR was then conducted using the RNAIIA primer (whose base sequence shown by SEQ ID NO:5 in the Sequence Listing) and the 1870 primer (whose base sequence shown by SEQ ID NO:6 in the Sequence Listing) to yield an amplified DNA fragment, which was then digested with XbaI and mixed with the plasmid pSTV28, previously digested with XbaI, for ligation to yield the plasmid pHS2870. The construct of the plasmid pHS2870 is shown in FIG. 4.

(3) Construction of the runaway plasmid pCRS04

After digestion with AccI (produced by Takara Shuzo) and NspI, the above-described plasmid pHS2870 was blunted at both ends and subjected to self-ligation to yield the plasmid pCRS01, which lacks the P15A replication origin. The plasmid was then digested with EcoRI (produced by Takara Shuzo) and XbaI, after which it was blunted at both ends and subjected to self-ligation in the same manner as above to construct the plasmid pCRS02. After an about 1.2 kb DNA fragment obtained by digesting the plasmid pMJR1560 with KpnI (produced by Takara Shuzo) and PstI was blunted at both ends, it was mixed with the above-described plasmid pCRS02, previously digested with NspV and VspI (both produced by Takara Shuzo) and then blunted at both ends, for ligation to yield the plasmid pCRS04. The flow diagram of the construction of the plasmid pCRS04 is shown in FIG. 5, and the construct of the plasmid pCRS04 shown in FIG. 6.

(4) Construction of the runaway expression vector pACE601

Figure 9:
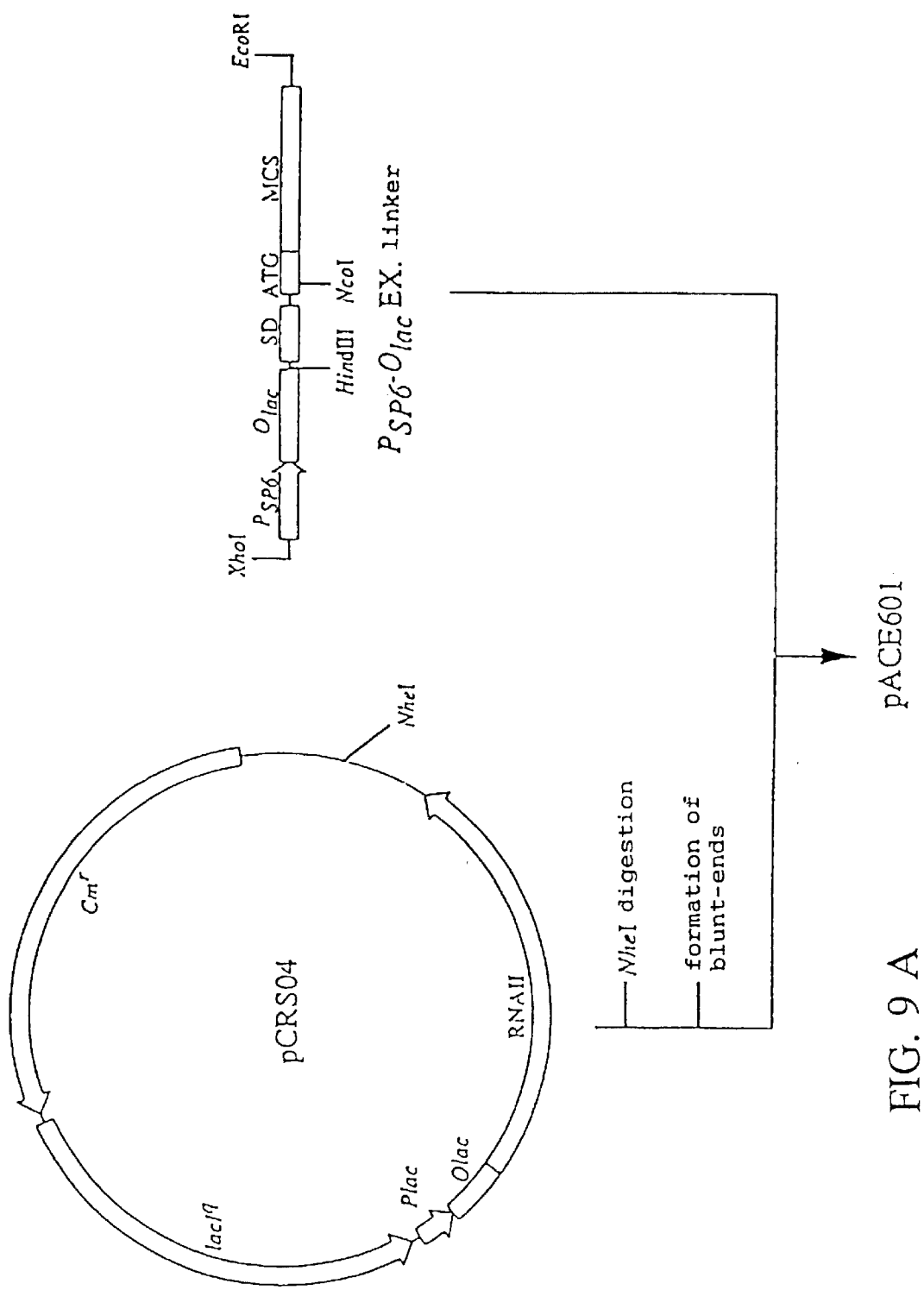
FIGS. 9(A), (B) show the procedure of the construction of the plasmid pACE601.
Figure 9:
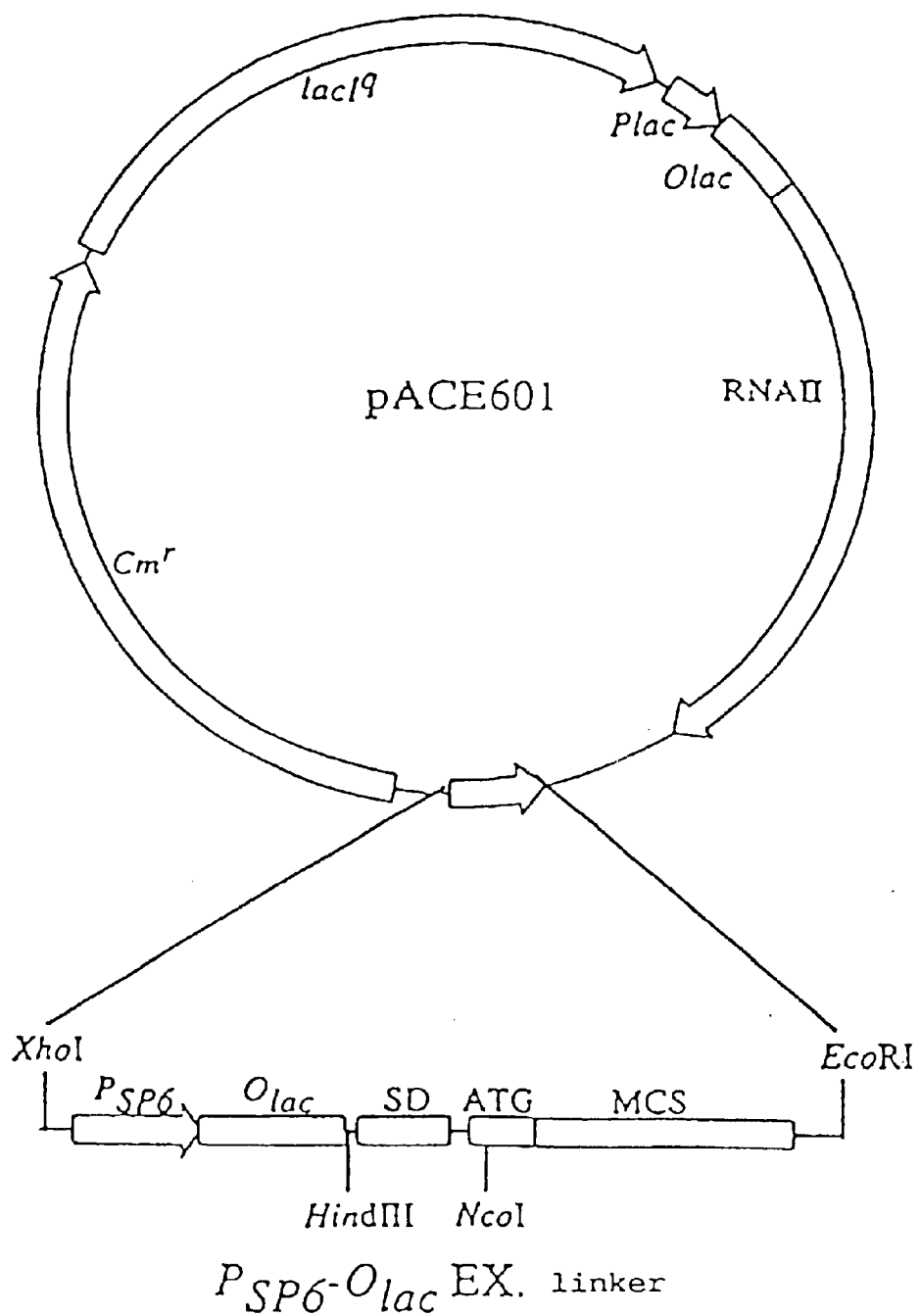

The above-described plasmid pCRS04, previously digested with NheI (produced by Takara Shuzo) and subsequently blunted at both ends, was mixed with the $P_{SP6}$-$O_{lac}$ EX linker, prepared from the two DNA strands whose base sequences are shown by SEQ ID NO:7 and SEQ ID NO:8 in the Sequence Listing, for ligation to construct the plasmid pACE601. The flow diagram of the construction of the plasmid pACE601 is shown in FIG. 9. The construction of these plasmids were conducted with Escherichia coli JM109 as a host.

(5) Construction of the runaway expression vector pACE611

Figure 10:
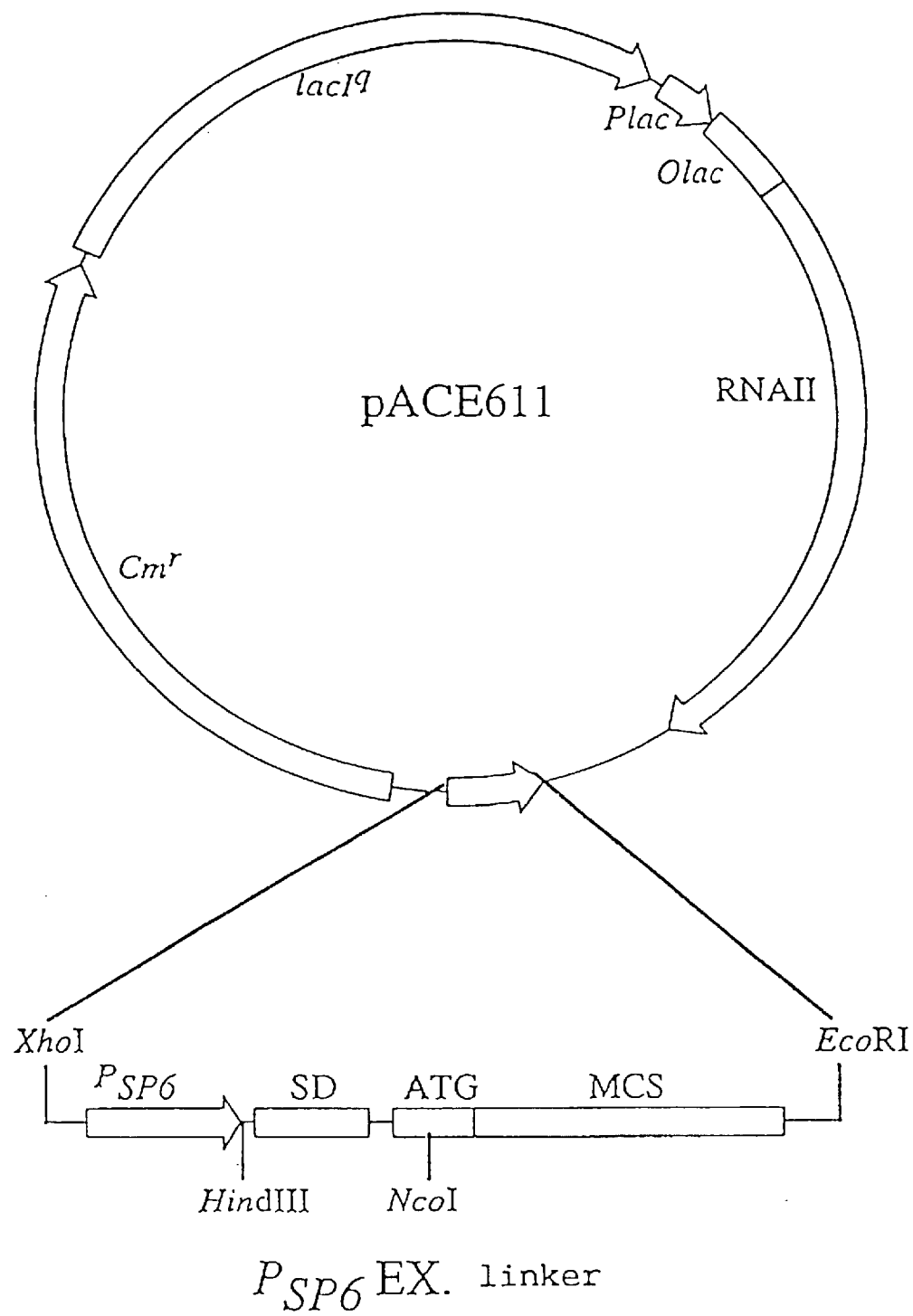
FIG. 10 shows the constitution of the plasmid pACE611.
Figure 11:
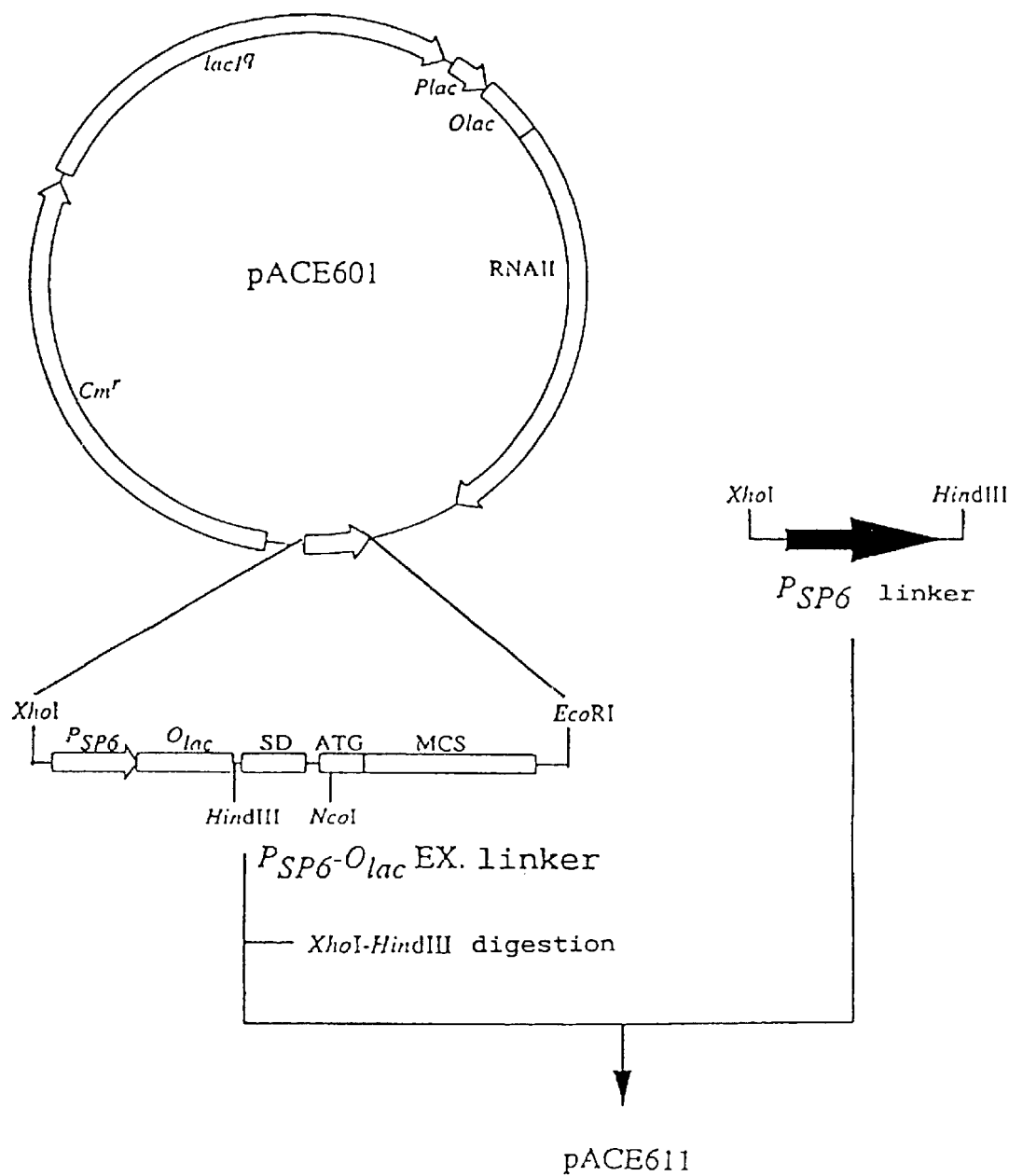
FIGS. 11(A), (B) show the procedure of the construction of the plasmid pACE611.
Figure 11:
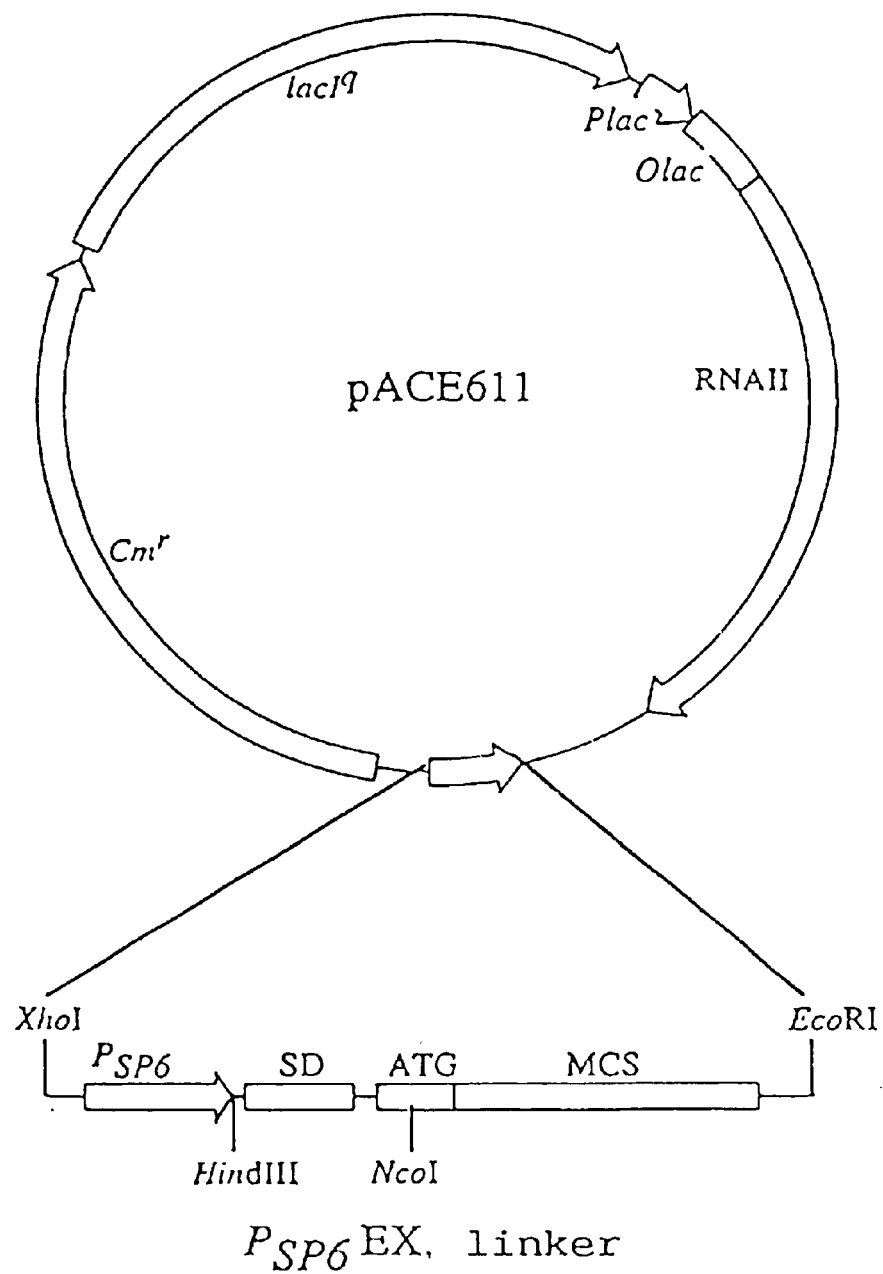

The runaway expression vector pACE601 was digested with XhoI-HindIII, and the $P_{SP6}$ linker, consisting of the synthetic oligo-DNAs shown by SEQ ID NO:15 and SEQ ID NO:16 in the Sequence Listing, was inserted into that site to construct the runaway expression vector pACE611. The construct of pACE611 is shown in FIG. 10. The flow diagram of the construction of the plasmid pACE611 is shown in FIG. 11.

(6) Construction of the runaway expression vectors pACE701 and pACE702

Figure 12:
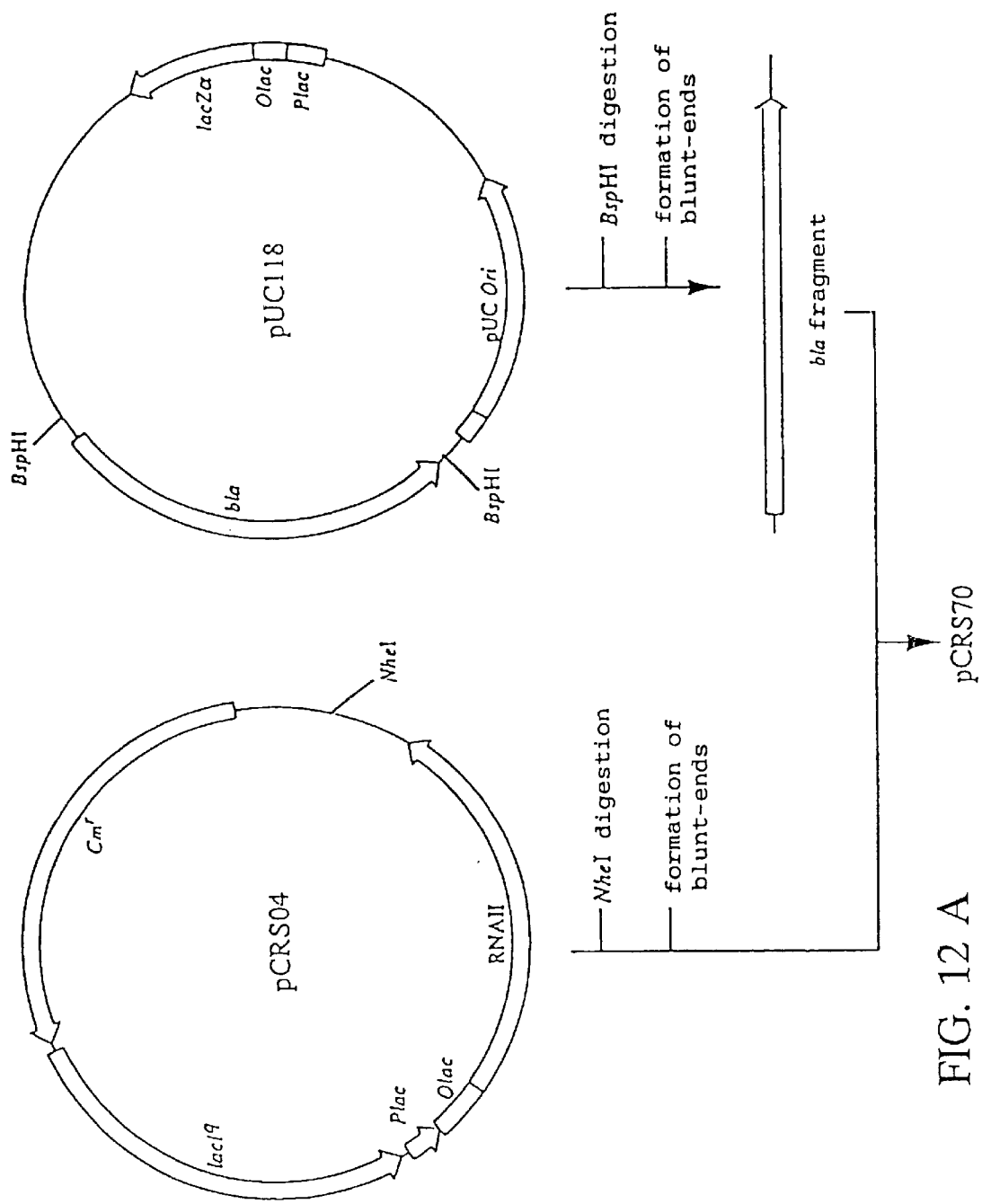
FIGS. 12(A), (B) show the procedure of the construction of the plasmid pCRS70.
Figure 12:
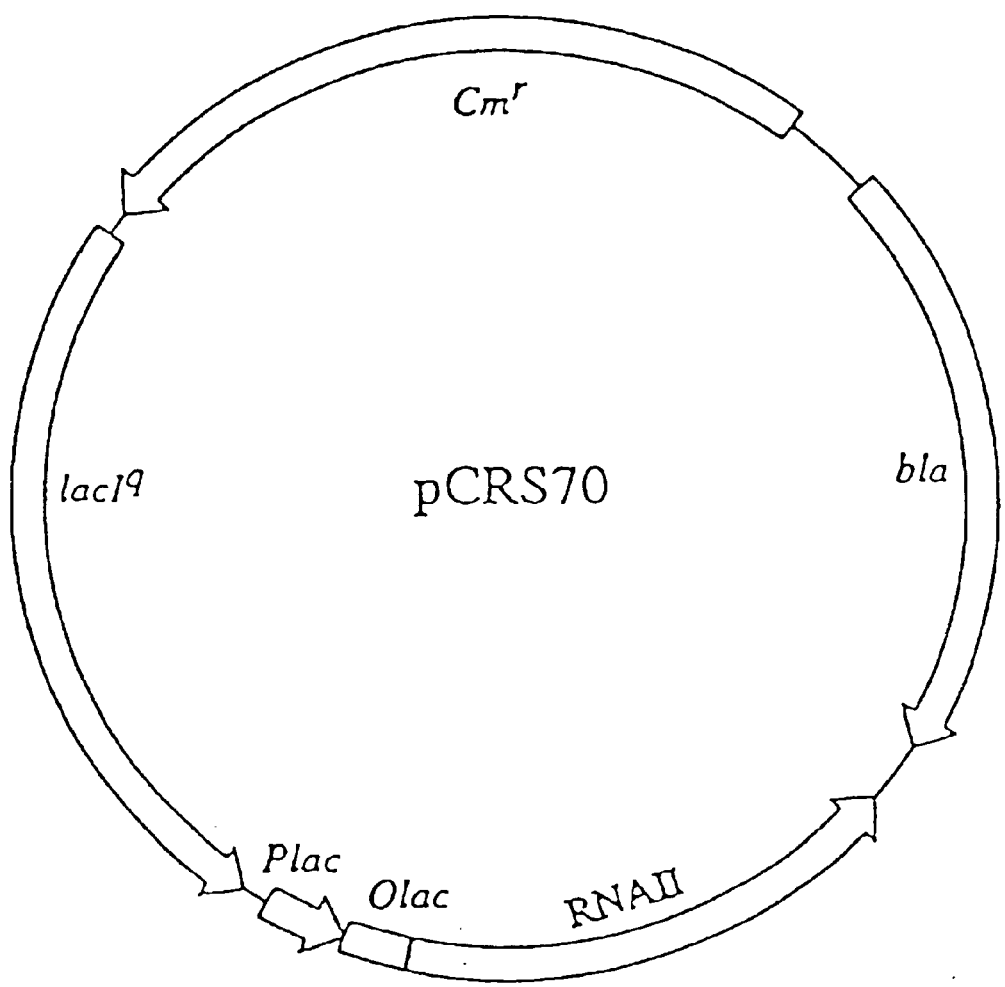
Figure 13:
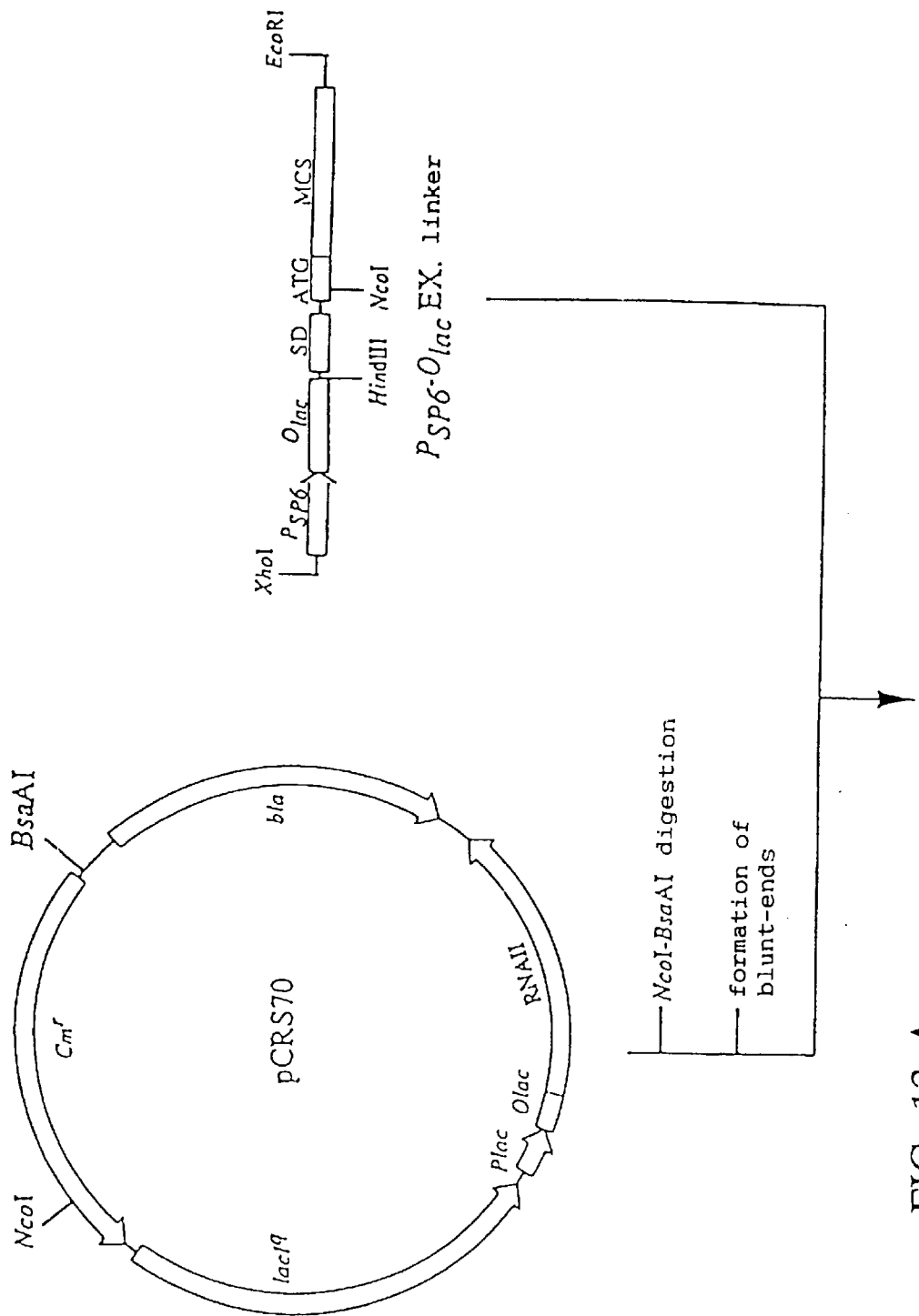
FIGS. 13(A), (B) show the procedure of the construction of the plasmids pACE701 and pACE702.
Figure 13:
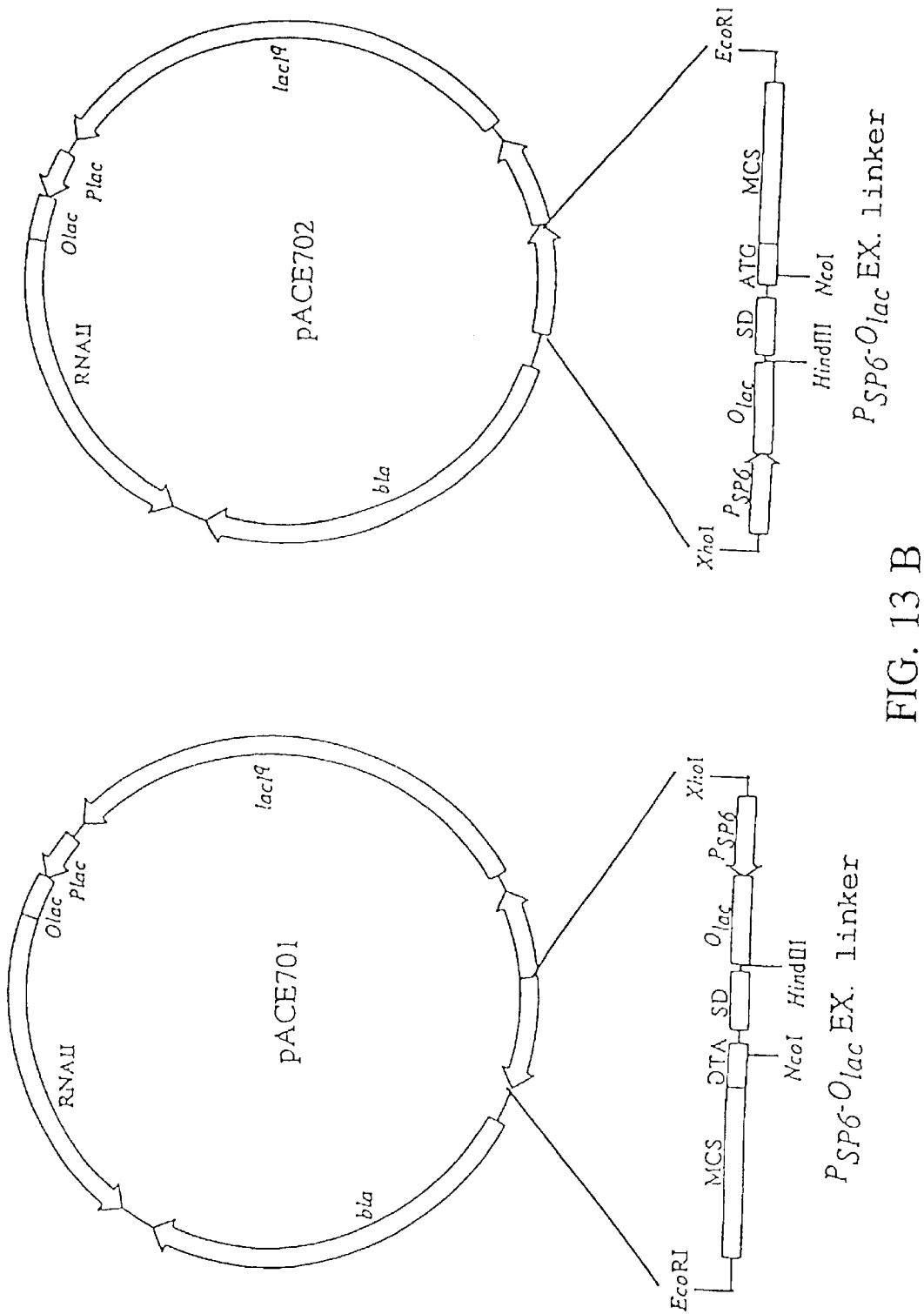

An about 1 kb DNA fragment obtained by digesting the plasmid vector pUC118 (produced by Takara Shuzo) with BspHI (produced by NER) was blunted at both ends, after which it was mixed with the above-described plasmid pCRS04, previously digested with NheI, and blunted at both ends, for ligation to construct the plasmid pCRS70. The flow diagram of the construction of the plasmid pCRS70 is shown in FIG. 12. Next, the plasmid was digested with NcoI (produced by Takara Shuzo) and BsaAI (produced by NEB), after which it was blunted at both ends and mixed with the above-described $P_{SP6}$-$O_{lac}$ EX linker for ligation to construct two plasmids pACE701 and pACE702, which incorporate the linker inserted in mutually opposite directions. The flow diagrams of the construction of the plasmids pACE701 and pACE702 are shown in FIG. 13. The construction of these plasmids were conducted with *Escherichia coli* JM109 as a host.

(7) Construction of model runaway expression plasmids

PCR was conducted using the primers trpA-N-NcoI and lacZ-C-NcoI with the above-described plasmid pMS434 as a template, to yield a DNA fragment containing the β-galactosidase gene. The base sequences of the primers trpA-N-NcoI and lacZ-C-NcoI are shown by SEQ ID NO:9 and SEQ ID NO:10 in the Sequence Listing, respectively. After digestion with NcoI, the fragment was mixed with each of the above-described plasmids pACE601, pACE701 and pACE702, all previously digested with NcoI, for ligation to yield the model runaway expression plasmids pACE601Z, pACE701Z and pACE702Z, all incorporating the β-galactosidase gene introduced downstream of the $P_{SP6}$-$)_{lac}$ sequence. The construction of these plasmids were conducted with *Escherichia coli* JM109 as a host.

(8) Evaluation of the expression levels of runaway expression plasmid in a non-inductive condition The transformants MC4100/pFSP6/pACE601Z, MC4100/pFSP6/pACE701Z and MC4100/pFSP6/pACE702Z, which were obtained after introducing the above-described model runaway expression plasmids pACE601Z, pACE701Z and pACE702Z, respectively into *Escherichia coli* MC4100 incorporating the above-described system plasmid pFSP6 (hereinafter referred to as MC4100/PFSP6), were each cultured under the conditions described in Example (1); each culture broth collected during the logarithmic growth phase was assayed for β-galactosidase activity by the method described in Reference Example (4). In all transformants examined, β-galactosidase activity was below the detection limit, demonstrating a greater expression-suppressing effect than that obtained with the multicopy plasmids shown in Reference Example (4).

(9) Construction of the Nsp7524 III restriction endonuclease gene expression plasmid The plasmid pBRN3, which contains the Nsp7524 III restriction modification system gene, was prepared from *Escherichia coli* MC1061/pBRN3 (FERM BP-5741). PCR was conducted using the primers L-ORF and NspR-ORF3 with this plasmid as a template to yield an about 1 kb DNA fragment containing the Nsp7524 III restriction endonuclease gene alone. The base sequences of the primers L-ORF and NspR-ORF3 are shown by SEQ ID NO:11 and SEQ ID NO:12 in the Sequence Listing, respectively. After digestion with NcoI, the fragment was mixed with the above-described plasmid pACE601, previously digested with NcoI, for ligation to construct the plasmid pACE601-NspIII, which incorporates the Nsp7524 III restriction enzyme gene alone introduced downstream of the $P_{SP6}$-$O_{lac}$ sequence. The plasmid was stably retained in *Escherichia coli* JM109 not containing the Nsp7524 III modification enzyme gene.

(10) Construction of Nsp7524 III restriction endonuclease gene expression system The transformants HB101/pFSP6/pACE601-NspIII and HB101/pFSP6/pACE601, which were obtained after introducing the above-described plasmid pACE601-NspIII, which contains the Nsp7524 III restriction endonuclease gene, and the control plasmid pACE601 into *Escherichia coli* HB101 incorporating the above-described system plasmid pFSP6 (hereinafter referred to as HB101/PFSP6), were each cultured in LB medium until the stationary phase; each culture broth collected was inoculated to two tubes of fresh medium at 1% and aerobically cultured at 37° C. Upon reach of an $OD_{600}$ value of 0.6, IPTG was added to one of the tubes to a final concentration of 0.2 mM, followed by further cultivation. After completion of the cultivation, cells were harvested, suspended in cell disruption buffer A (20 mM Tris-HCl, pH 7.5, 10 mM 2-mercaptoethanol), and disrupted by ultrasonication, followed by centrifugation to yield a crude extract.

Figure 14:
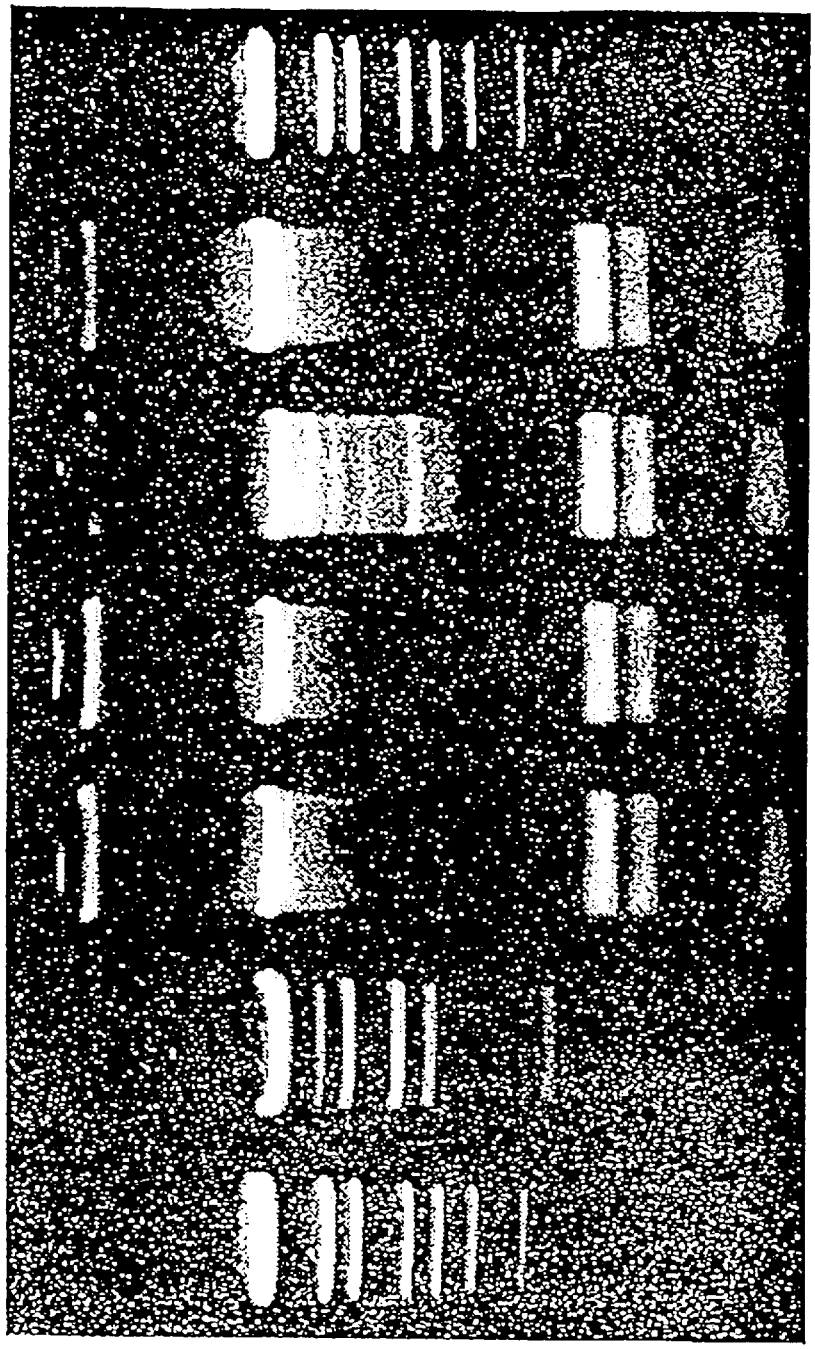
FIG. 14 shows the expression of the activity of Nsp 7524 III restriction endonuclease depending on the induction or non-induction of IPTG, by agarose gel electrophoresis of the degradation reaction solution of λ-DNA after introducing pFSP6 and pACE601 or pFSP6 and pACE601-NspIII into *Escherichia coli* HB101. In this figure, M indicates the λ-EcoT141 size marker; 1 indicates AvaI digested λ-DNA; 2 indicates HB101/pFSP6/pACE601 after induction; 3 indicates HB101/pFSP6/pACE601 before induction; 4 indicates HB101/pFSP6/pACE601-NspIII after induction; and 5 indicates HB101/pFSP6/pACE601-NspIII before induction.

A 1 μl portion of this crude extract was added to 30 μl of a reaction mixture (10 mM Tris-HCl, pH 7.5, 10 mM $MgCl_2$, 1 mM DTT, 50 mM NaCl, 1 μg λ-DNA) and reacted at 37° C. for 1 hour, after which the reaction mixture was subjected to agarose gel electrophoresis to examine for the digestion of λ-DNA and confirm restriction endonuclease activity. As shown in FIG. 14, restriction endonuclease activity was observed only in HB101/pFSP6/pACE601-NspIII with expression induced by the addition of IPTG, and its λ-DNA cleavage pattern agreed, with that of AvaI, an isoschizomer of Nsp7524 III.

Figure 15:
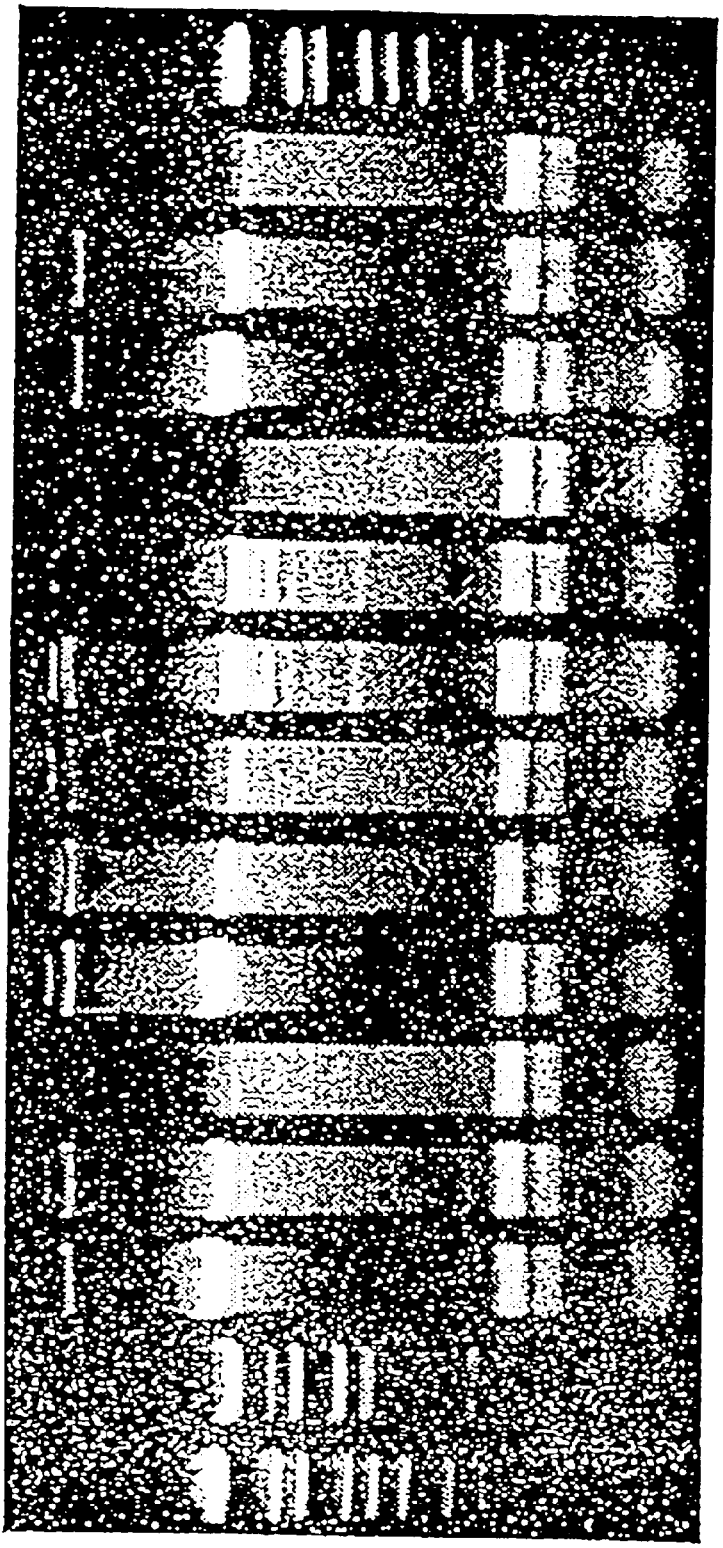
FIG. 15 shows a result of an agarose gel electrophoresis in the case of 2 and 3 hour-elongation of the degradation reaction of λ-DNA depending on the induction or non-induction of IPTG after introducing pFSP6 and pACE601 or pFSP6 and pACE601-NspIII into *Escherichia coli* HB101. In this figure, M indicates the λ-EcoT141size marker; 1 indicates AvaI digested λ-DNA; 2 indicates HB101/pFSP6/pACE601 after 1 hour (induction); 3 indicates HB101/pFSP6/pACE601 after 2 hours (induction); 4 indicates HB101/pFSP6/pACE601 after 3 hours (induction); 5 indicates HB101/pFSP6/pACE601 after 1 hour (non-induction); 6 indicates BB101/pFSP6/pACE601 after 2 hours (non-induction); 7 indicates HB101/pFSP6/pACE601 after 3 hours (non-induction); 8 indicates HB101/pFSP6/pACE601-NspIII after 1 hour (induction); 9 indicates HB101/pFSP6/pACE601-NspIII after 2 hours (induction); 10 indicates HB101/pFSP6/pACE601-NspIII after 3 hours (induction); 11 indicates HB101/pFSP6/pACE601-NspIII after 1 hour (non-induction); 12 indicates HB101/pFSP6/pACE601-NspIII after 2 hours (non-induction); and 13 indicates HB101/pFSP6/pACE601-NspIII after 3 hours (non-induction).

The results of the above-described λ-DNA digestion reaction as conducted for extended periods of 2 and 3 hours are shown in FIG. 15. In this case, because the crude extract used in the present experiment contained nuclease derived from the host *Escherichia coli*, the DNA fragment resulting from Nsp7524 III activity underwent further degradation by *Escherichia coli* nuclease, resulting in bands whose density decreased as the increase in reaction time, on lanes 8 through 10, with no bands detected on lane 10. On lanes 11 through 13, the Nsp7524 III digestion fragment was not produced because of the absence of Nsp7524 III induction even when reaction time was extended, demonstrating that the λ-DNA was made into the lower molecular weight fragments by the direct action of *Escherichia coli* nuclease. No restriction endonuclease activity was detected in the crude extract from HB101/pFSP6/pACEA601.

Example 2

Isolation and expression of the AccIII restriction endonuclease gene (1) Determination of N-terminal amino acid sequence of AccIII restriction endonuclease protein and synthesis of primer DNA corresponding to the amino acid sequence About 2 ku of a commercial product of the AccIII restriction endonuclease (produced by Takara Shuzo) was subjected to gel filtration using a column of Sephacryl S300 (produced by Pharmacia) to determine the molecular weight of the AccIII restriction endonuclease. Judging from the elution position where activity was detected, the molecular weight of the AccIII restriction endonuclease was proven to be about 70,000. Because most restriction endonuclease proteins are dimers, the AccIII restriction endonuclease protein was expected to be mobilized to a position for a molecular weight of about 35,000 in SDS polyacrylamide gel electrophoresis.

Next, to obtain a sample for N-terminal amino acid sequencing of the AccIII restriction endonuclease protein, about 2 ku of a commercial product of the AccIII restriction endonuclease, together with a protein molecular weight marker, was subjected to SDS polyacrylamide gel electrophoresis, after which the protein was transferred from the gel to a PVDF membrane and stained with bromophenol blue to confirm the protein position. After destaining with 10% acetic acid-50% methanol, the portion of the PVDF membrane where a protein of about 35,000 molecular weight was blotted was cut out and subjected to automatic Edman degradation using the protein sequencer G1000A (produced by Hewlett-Packard) to determine the N-terminal amino acid sequence shown by SEQ ID NO:19 in the Sequence Listing. On the basis of this sequence, AccIII primers 1 and 2, shown by SEQ ID NO:20 and SEQ ID NO:21 in the Sequence Listing, respectively, were then synthesized for use as a pair of cassette primers.

(2) Preparation of genomic DNA of Acc bacterium

In accordance with the method of Kita et al., described in Nucleic Acids Research, Vol. 13, pp. 8685–8694 (1985), the Acc bacterium was cultured to obtain wet cells. Two grams of the wet cells obtained was suspended in 10 ml of buffer B [25 mM Tris-HCl (pH 8.0), 50 mM glucose, 10 mM EDTA], stirred in the presence of 1 ml of a lysozyme solution prepared to 2 mg/ml in buffer B, and kept standing at 37° C. for 20 minutes. Next, 28 ml of buffer C [100 mM NaCl, 100 mM Tris-HCl (pH 8.0)] was added to this solution, followed by stirring. One milliliter of a proteinase K solution prepared to 20 mg/ml in TE [10 mM Tris-HCl, 1 mM EDTA (pH 8.0)] and 4 ml of a 10% SDS solution were further added, followed by stirring, after which the mixed solution was kept standing at 37° C. for 1 hour.

To this solution, 6 ml of a 5 M aqueous solution of NaCl and 6 ml of buffer D [10% CTAB (cetyl trimethyl ammonium bromide), 0.7 M NaCl] was added, followed by stirring, after which the mixed solution was kept standing at 60° C. for 20 minutes. This solution was treated with phenol and subsequently with chloroform, after which the water layer was separated. To the water layer, 50 μl of an RNaseA (produced by Sigma) solution prepared to 10 mg/ml in TE was added, followed by stirring, after which the mixed solution was kept standing at 37° C. for 40 minutes. After being kept standing, this solution was treated with phenol and subsequently with chloroform, after which the water layer was separated. To the water layer, an equal volume of cold ethanol was added; the DNA precipitated was recovered by winding around a glass capillary. The DNA was washed with 70% ethanol and dissolved in 3 ml of TE to yield about 200 μg of genomic DNA.

(3) Preparation of Accgenomic cassette library

The following procedures were conducted basically in accordance with the method described on pages F16–F17 in "Gene Engineering Guide" (1995–1996 edition), Takara Shuzo.

The genomic DNA obtained in (2) was completely digested with EcoRI (produced by Takara Shuzo); the DNA fragment obtained was ligated with an EcoRI cassette (produced by Takara Shuzo), having a cohesive end complementary thereto, to yield an EcoRI cassette library. Similarly, the genomic DNA was completely digested separately with the restriction endonucleases BglII, EcoT14I, EcoT22I, HindIII, PstI, SalI and XbaI (all produced by Takara Shuzo). The genomic DNA fragments obtained were each bound to each of several cassettes (produced by Takara Shuzo), having a complementary protruding end, to yield the BglII, EcoT14I, EcoT22I, HindIII, PstI, SalI and XbaI cassette libraries, respectively. These cassette libraries are generically referred to as the Accgenomic cassette library.

(4) Analysis of the AccIII restriction endonuclease gene

A PCR-based DNA amplification reaction was carried out using a primer pair of AccIII primer 1 and cassette primer C1 (produced by Takara Shuzo) with the EcoRI cassette library obtained in (3) as a template. To efficiently and specifically amplify the desired region, a second PCR-based DNA amplification reaction was carried out using a primer pair of AccIII primer 2 and cassette primer C2 (produced by Takara Shuzo) with a portion of the reaction liquid obtained, to yield an amplified DNA fragment. Similarly, with the BglII, EcoT14I, EcoT22I, HindIII, PstI, SalI and XbaI cassette libraries as a template respectively, the above two-step PCR-based DNA amplification reaction was carried out separatedly to yield amplified DNA fragments. Each amplified DNA was analyzed by agarose gel electrophoresis; the amplified DNA fragment derived from the XbaI cassette library showed a particularly high amplification efficiency.

With this in mind, a PCR-based DNA amplification reaction was again carried out using a primer pair of AccIII primer 1 and cassette primer C1 with the XbaI cassette library as a template. This reaction mixture was subjected to agarose gel electrophoresis; an about 0.5 kb amplified DNA fragment was recovered from the gel. A second PCR-based DNA amplification reaction was carried out using a primer pair of AccIII primer 2 and cassette primer C2 with the DNA fragment obtained as a template. Base sequencing of the about 0.5 kb amplified DNA fragment obtained demonstrated that the fragment encodes a portion of the protein whose N-terminal amino acid sequence was determined in (1). On the other hand, the putative molecular weight of the AccIII restriction endonuclease protein is about 35,000, and the gene encoding the protein is assumed to be about 1 kb in length. It was therefore expected that the base sequence of the AccIII restriction endonuclease gene could be determined, provided that information on the accurate base sequence of the 5'-terminal region to which AccIII-primers 1 and 2 annealed, and information on the remaining about 0.5 kb base sequence in the 3' region, were available, in addition to the above-described information on the about 0.5 kb base sequence.

With this in mind, to determine the accurate base sequence of the 5'-terminal region-of the AccIII restriction, endonuclease gene region, AccIII primer 3, shown by SEQ ID NO:22 in the Sequence Listing, and AccIII primer 4, shown by SEQ ID NO:23 in the Sequence Listing, were synthesized. Next, a PCR-based DNA amplification reaction was carried out using a primer pair of AccIII primer 4 and cassette primer C1 with the EcoRI cassette library obtained in (3) as a template. A PCR-based DNA amplification reaction was carried out using a primer pair of AccIII primer 3 and cassette primer C2 with a portion of this reaction mixture. Similarly, with the BglII, EcoT14I, EcoT22I, HindIII, PstI, SalI and XbaI cassette libraries as a template respectively, the above two-step PCR-based DNA amplification reaction was separatedly carried out. Of the DNA fragments amplified, the shortest, i.e., the about 1 kb DNA fragment was obtained with the EcoT141I cassette library as a template, the base sequence thereof was determined.

Furthermore, to determine the about 0.5 kb sequence on the 3' side of the gene region assumed to encode the AccIII restriction endonuclease protein, AccIII primer 5, shown by SEQ ID NO:24 in the Sequence Listing, and AccIII primer 6, shown by SEQ ID NO:25 in the Sequence Listing, were synthesized. A PCR-based DNA amplification reaction was carried out using a primer pair of AccIII primer 5 and cassette primer C1 with the EcoRI cassette library obtained in (3) as a template. A PCR-based DNA amplification reaction was carried out using a primer pair of AccIII primer 6 and cassette primer C2 with a portion of this reaction mixture. Similarly, with the BglII, EcoT14I, EcoT22I, HindIII, PstI, SalI and XbaI cassette libraries as a template respectively, the above two-step PCR-based DNA amplification reaction was carried out separatedly.

Of the DNA fragments amplified, the about 0.5 kb and about 0.8 kb DNA fragments each obtained with the EcoT22I and HindIII cassette libraries as a template respectively were subjected to a base sequencing. Combining the results for the three base sequences determined, the base sequence information on an about 1.6 kb DNA fragment was obtained. Its base sequence is shown by SEQ ID NO:26 in the Sequence Listing. Furthermore, searching for an open reading frame (ORF) capable of encoding the protein demonstrated the presence of ORF1 at base numbers 558 through 1442, a portion thought to be ORF2 at base numbers 1588 through 1434, and a portion thought to be ORF3 at base numbers 1 through 535. Encoding the protein whose N-terminal amino acid sequence was determined in (1), ORF1 was deemed to be the AccIII restriction endonuclease gene. The base sequence of the AccIII restriction endonuclease gene is shown by SEQ ID NO:2 in the Sequence Listing, wherein the fourth base, as counted from the 5' terminus, is C. The amino acid sequence deduced from the base sequence is shown by SEQ ID NO:1 in the Sequence Listing, wherein the second amino acid, as counted from the N terminus, is Leu. The direction of translation of ORF2 is opposite that of ORF1 and ORF3.

(5) Construction of the plasmid pCRA19

Next, a plasmid for expression of the AccIII restriction endonuclease gene was constructed. First, to obtain the gene, the primer Acc-RL, shown by SEQ ID NO:27 in the Sequence Listing, and the primer Acc-RR, shown by SEQ ID NO:28 in the Sequence Listing, were synthesized. A restriction endonuclease NcoI recognition sequence site was introduced into both primers. Using the above described primer pair, it is possible to cut out the AccIII restriction endonuclease gene from an amplified DNA fragment obtained by PCR with the genomic DNA of the Acc bacterium as a template, using the restriction endonuclease NcoI, and the translation codon frames coincide with each other under control of the SP6 promoter when the gene is inserted into the NcoI site of the pACE611 vector. On the other hand, a use of this primer pair results in replacement of the fourth base, as counted from the 5' terminus of the AccIII restriction endonuclease gene, from C to G, and of the second amino acid, as counted from the N terminus of the protein encoded by the gene, from Leu to Val. Using the above primer pair with the genomic DNA of the Acc bacterium obtained in (2) as a template, a PCR-based DNA amplification reaction was carried out. This DNA fragment was completely digested with the restriction endonuclease NcoI (produced by Takara Shuzo), after which it was subjected to agarose gel electrophoresis; a DNA fragment of about 900 bp size was recovered. Next, this DNA fragment was inserted into the NcoI site of the pACE611 vector so that it was located downstream of the SP6 promoter.

This recombinant DNA was introduced into *Escherichia coli* JM109 to yield transformants. Thirty transformants were randomly selected, and each inoculated to 5 ml of an LB medium containing 30 μg/ml chloramphenicol and cultured at 37° C. When the $OD_{600}$ value of the cell culture broth reached 0.6, IPTG was added to a final concentration of 2 mM to increase the plasmid copy number, followed by further cultivation at 37° C. for 2 hours, after which plasmid DNA was prepared from each culture. Each plasmid DNA obtained was simultaneously cleaved with the restriction endonucleases HindIII and XbaI, followed by confirmation of the length of the resulting DNA fragments by agarose gel electrophoresis; a plasmid thought to contain the gene region inserted in the right direction was detected. This plasmid, designated pCRA19, was introduced into *Escherichia coli* JM109 to yield a transformant, which was designated *Escherichia coli* JM109/pCRA19.

(6) Construction of expression system for the AccIII restriction endonuclease gene First, the SP6 RNA polymerase gene was introduced into *Escherichia coli* JM109 to construct a phage vector allowing further expression of the gene. Specifically, by inserting an SP6 RNA polymerase gene fragment obtained by BamHI-HindIII digestion of pSP6-2 into the BamHI-HindIII site within the multicloning site of a commercial product of the phage vector M13mp18 (produced by Takara Shuzo), the SP6 RNA polymerase expression phage M13sp6 was constructed.

Next, the transformant *Escherichia coli* JM109/pCRA19 was inoculated to 5 ml of an LB medium containing 30 μg/ml chloramphenicol and cultured at 37° C. When the $OD_{600}$ value of the cell culture broth reached 0.6, IPTG was added to a final concentration of 2 mM to increase the plasmid copy number, followed by further cultivation at 37° C. for 2 hours. These cells were then infected with the phage M13sp6 to express the protein encoded by the AccIII restriction endonuclease gene, followed by further cultivation at 37° C. for 16 hours. A 11 mg portion of the wet cells obtained was suspended in 180 μl of cell disruption buffer E [20 mM Tris-HCl (pH 7.5), 10 mM 2-mercaptoethanol], after which the cells were disrupted by ultrasonication, followed by centrifugation (18000 g, 10 minutes) to separate the solid and liquid.

Determining the activity of the supernatant under the activity determination conditions shown on the data sheet attached to the AccIII restriction endonuclease produced by Takara Shuzo demonstrated the production of the AccIII restriction endonuclease in an amount of about 8000 units per gram of wet cells, a level about 16 times that obtained with the Acc bacterium, per unit weight of wet cells. Neither activity of restriction endonucleases other than AccIII nor AccIII modification enzyme activity was noted in the supernatant obtained. Regarding the AccIII restriction endonuclease gene inserted into the plasmid pCRA19, it was demonstrated that the fourth base, as counted from the translation initiation base, was replaced from C to G, upon DNA amplification by PCR, resulting in the replacement of the second amino acid, as counted from the N-terminus of the translated protein, from Leu to Val, and that the protein possesses AccIII restriction endonuclease activity.

An isolation/mass production system for the AccIII restriction endonuclease gene in the absence of AccIII modification enzyme was thus developed.

(7) Isolation of the AccIII modification enzyme gene

Modification enzyme genes and restriction endonuclease genes are often closely located. With this in mind, to determine the ORF2 region deduced in (4) above, the base sequence of an about 1.4 kb DNA fragment obtained using the EcoRI cassette library as a template, out of the amplified DNA fragments prepared to determine the 3' region of the AccIII restriction endonuclease gene in (4) above, was determined. Next, to determine the ORF3 region deduced in (4) above, the base sequence of an about 2.2 kb DNA fragment obtained using the BglII cassette library as a template, out of the amplified DNA fragments prepared to determine the 5'-terminal region of the AccIII restriction endonuclease gene in (4) above, was determined. Combining these base sequences and the base sequence of the about 1.6 kb DNA fragment containing the AccIII restriction endonuclease gene region determined in (4) resulted in the information on the about 4.2 kb base sequence shown by SEQ ID NO:29 in the Sequence Listing. The AccIII restriction endonuclease gene was located at base numbers 1913 through 2797, ORF2 at base numbers 3712 through 2789, and ORF3 at base numbers 691 through 1890. Of these ORFs, ORF2 proved to contain a portion highly homologous to the conserved region among modification enzymes in a known restriction modification system.

Next, to obtain the ORF2 region, an about 1.1 kb ORF2-containing portion was cut out using EcoT22I and HpaI (produced by Takara Shuzo) from an amplified DNA fragment obtained by two-step PCR using a primer pair of Accprimer 6 and cassette primer C1 and another primer pair of Acc primer 5 and cassette primer C2 in the respective steps, with the EcoRI cassette library as a template, and was inserted into the SmaI site downstream of the lac promoter in the pUC118 vector. If this recombinant plasmid contains the AccIII modification enzyme gene, and if the AccIII modification enzyme can be expressed in *Escherichia coli*, the DNA in the culture of the transformant obtained by introducing this recombinant plasmid into *Escherichia coli*JM109 would undergo methylation by the AccIII modification enzyme and acquire resistance to cleavage by the AccIII restriction endonuclease.

Because the pUC118 vector used to construct this recombinant plasmid has no AccIII restriction endonuclease recognition sequence, however, it is inappropriate to use this recombinant plasmid by itself to confirm AccIII modification enzyme activity. On the other hand, there is an AccIII restriction endonuclease recognition sequence in the plasmid pSTV29, which can be co-present with this recombinant plasmid in *Escherichia coli* JM109. With this in mind, to utilize pSTV29 as an index of expression of the AccIII modification enzyme, the above recombinant plasmid and pSTV29 were both introduced into *Escherichia coli* JM109 to yield transformants. Three transformants were each cultured at 37° C. for 16 hours in 2 ml of an LB medium containing 100 µg/ml ampicillin, 30 µg/ml chloramphenicol and 2 mM IPTG, after which plasmid DNA was prepared from each culture.

The DNA thus prepared is available as a mixture of pSTV29 and the above-described recombinant plasmid. When each DNA sample was subjected to a digestion with the AccIII restriction endonuclease, the pSTV29 in all samples exhibited resistance to the AccIII restriction endonuclease activity, demonstrating the insertion of the AccIII modification enzyme gene into the recombinant plasmid contained in the DNA sample. Furthermore, when the DNA sample was simultaneously cleaved with the restriction endonucleases HindIII and XbaI, followed by analysis of the length of the resulting DNA fragments by agarose gel electrophoresis, the presence of ORF2 in the recombinant plasmid was confirmed. ORF2 was thus proven to be the AccIII modification enzyme gene. The base sequence of the AccIII modification enzyme gene obtained and the amino acid sequence deduced therefrom are shown by SEQ ID NO:14 and SEQ ID NO:13 in the Sequence Listing, respectively.

Figure 16:
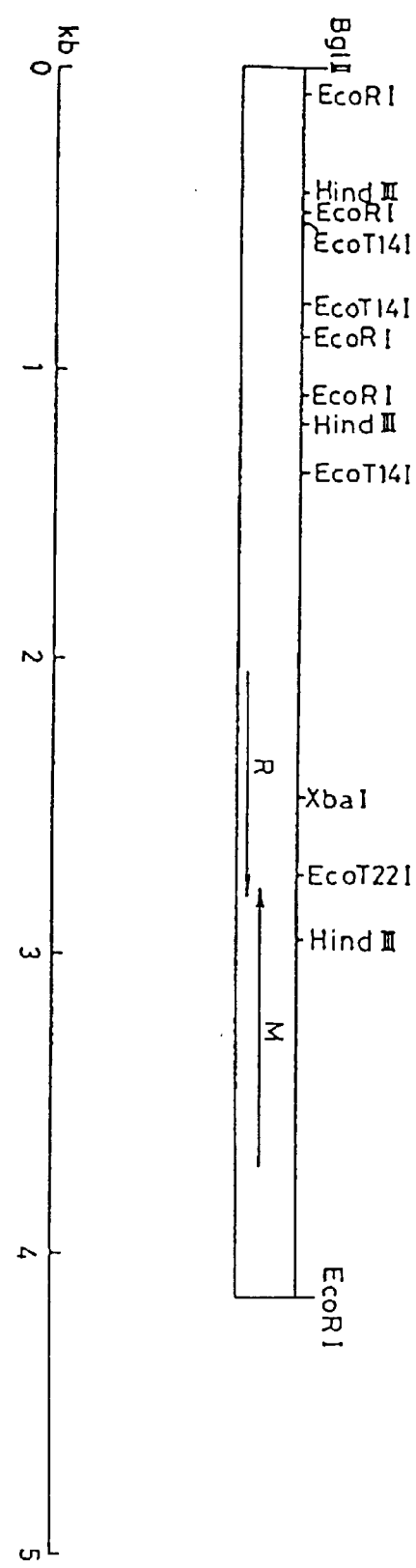
FIG. 16 shows the construction of the AccIII restriction modification system gene.

The structure of the AccIII restriction modification system gene demonstrated according to the present invention is shown in FIG. 16, wherein M, R and the arrow represent the modification enzyme gene, the restriction endonuclease gene, and the orientation of ORF, respectively.

INDUSTRIAL APPLICABILITY

The present invention provides a plasmid vector capable of introducing into a host an exogenous desired gene encoding a protein lethal or harmful to the host, and a method for being capable of efficiently expressing the protein using the plasmid vector for the first time. A method for being capable of isolating a restriction endonuclease gene which constitutes a restriction modification system without co-existence of a modification enzyme gene, which has been difficult in the prior arts, is also provided. Furthermore, an AccIII restriction endonuclease gene and an AccIII modification enzyme gene are isolated by the present invention, and, from *Escherichia coli* transformed with the plasmid containing the gene, it is possible to easily obtain an AccIII restriction endonuclease or an AccIII modification enzyme available in the genetic engineering at a desired purity of an enzyme preparation compared to the prior method for purification.

What is claimed is:

1. A method for isolating a desired gene, which comprises
   (i) inserting DNA fragments of obtained from DNA containing the desired gene into a plasmid vector(s) comprising a promoter sequence to control an expression of a desired gene, said promoter sequence being recognized by an RNA polymerase derived from SP6 phage, and a replication origin for increasing a copy number by induction with an exogenous factor, said replication origin comprising lac promoter and RNAII region, wherein said desired gene encodes a protein lethal or harmful to the host;
   (ii) transforming host cells with the resulting vector(s) of step (i)
   (iii) selecting the transformed host cells containing said desired gene.

2. The method for isolating a desired gene according to claim 1, wherein the gene encoding a protein lethal or harmful to the host is a restriction endonuclease gene.

3. The method of claim 1, wherein said DNA fragment is obtained by cleaving DNA containing the desired gene with restriction endonuclease.

4. The method of claim 1, wherein said DNA fragment is obtained by PCR using a DNA containing the desired gene.

5. The method of claim 2, wherein said plasmid vector comprises the restriction endonuclease gene but does not contain a corresponding modification enzyme.

* * * * *